(12) United States Patent
Dong et al.

(10) Patent No.: US 11,022,610 B1
(45) Date of Patent: Jun. 1, 2021

(54) INTEGRATED DUAL-MODALITY MICROFLUIDIC SENSOR FOR BIOMARKER DETECTION USING LITHOGRAPHIC PLASMONIC CRYSTAL

(71) Applicant: Iowa State University Research Foundation, Inc., Ames, IA (US)

(72) Inventors: Liang Dong, Ames, IA (US); Azahar Ali, Ames, IA (US); Shawana Tabassum, Ames, IA (US); Qiugu Wang, Ames, IA (US); Ratnesh Kumar, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 162 days.

(21) Appl. No.: 16/253,104

(22) Filed: Jan. 21, 2019

Related U.S. Application Data

(60) Provisional application No. 62/620,025, filed on Jan. 22, 2018.

(51) Int. Cl.
*G01N 21/552* (2014.01)
*G01N 27/327* (2006.01)
(Continued)

(52) U.S. Cl.
CPC .......... *G01N 33/553* (2013.01); *G01N 21/553* (2013.01); *G01N 27/3276* (2013.01);
(Continued)

(58) Field of Classification Search
CPC ..... G01N 2921/258; G01N 2921/5903; G01N 21/554; G01N 27/327;
(Continued)

(56) References Cited

U.S. PATENT DOCUMENTS 5,954,685 A  9/1999 Tierney

FOREIGN PATENT DOCUMENTS

WO  2015107339 A1  7/2015

OTHER PUBLICATIONS

Liang et al., "Measurement of Small Molecule Binding Kinetics on a Protein Microarray by Plasmon-Based Electrochemical Impedance Imaging," Anal. Chem. 2014, 86, 9860-9865 (Year: 2014).*

(Continued)

*Primary Examiner* — Alexander S Noguerola
(74) *Attorney, Agent, or Firm* — McKee, Voorhees & Sease, PLC

(57) ABSTRACT

An integrated dual-modality microfluidic sensor chip and methods for using the same. In one form, the sensor comprises a patterned periodic array of nanoposts coated with a noble metal and graphene oxide (GO) to detect target biomarker molecules in a limited sample volume. The device generates both electrochemical and surface plasmon resonance (SPR) signals from a single sensing area of the metal-GO nanoposts. The metal-GO nanoposts are functionalized with specific receptor molecules, serving as a spatially well-defined nanostructured working electrode for electrochemical sensing, as well as a nanostructured plasmonic crystal for SPR-based sensing via the excitation of surface plasmon polaritons. The integrated dual-modality sensor offers higher sensitivity (through higher surface area and diffusions from nanoposts for electrochemical measurements), as well as the dynamic measurements of antigen-antibody bindings (through the SPR measurement), while operating simultaneously in a same sensing area using a same sample volume.

Figure 1:
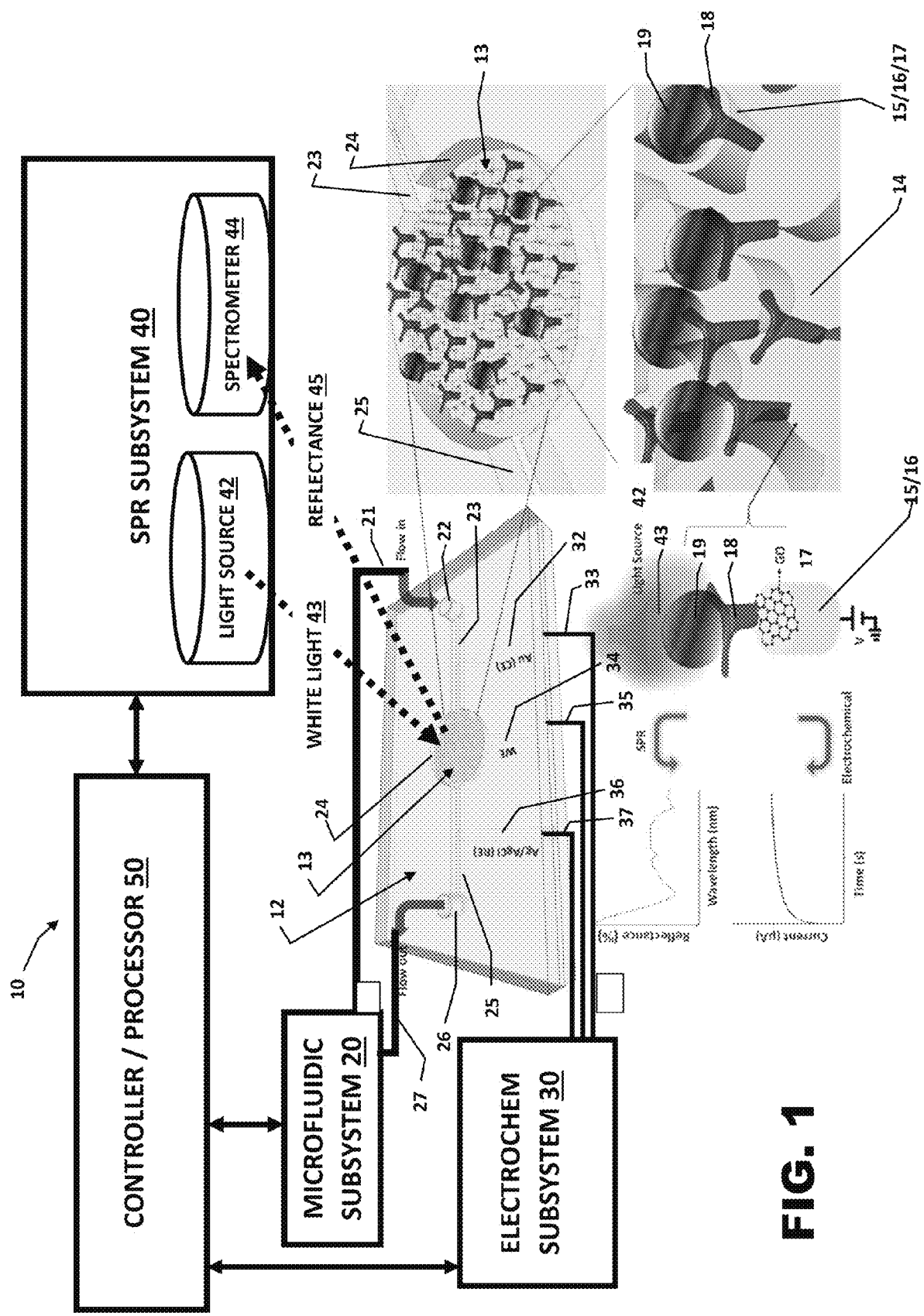

22 Claims, 50 Drawing Sheets
(40 of 50 Drawing Sheet(s) Filed in Color)

(51) Int. Cl.
G01N 33/553 (2006.01)
G01N 33/531 (2006.01)
G01N 33/574 (2006.01)
G01N 21/25 (2006.01)

(52) U.S. Cl.
CPC ....... *G01N 27/3278* (2013.01); *G01N 33/531* (2013.01); *G01N 33/5748* (2013.01); *B01L 2200/027* (2013.01); *G01N 2021/258* (2013.01)

(58) Field of Classification Search
CPC .......... G01N 27/3275–3278; G01N 2021/258; G01N 2021/5903
See application file for complete search history.

(56) References Cited

OTHER PUBLICATIONS

Zhang et al. "A Novel Graphene Oxide-Based Surface Plasmon Resonance Biosensor for Immunoassay,"small 2013, 9, No. 15, 2537-2540 plus Supplement (Year: 2013).*
BioNavis application note #143, downloaded from http://www.bionavis.com/en/publications/application-notes/143-antibody/on Sep. 17, 2020, published Dec. 24, 2017 (Year: 2017).*
Chegel et al., "Detection of biomolecules using optoelectronic biosensor based on localized surface plasmon resonance. Nanoimprint lithography approach," Semiconductor Physics, Quantum Electronics & Optoelectronics, 2009. V, 12, N 1. p. 91-97 (Year: 2009).*
National Cancer Institute definition of "antibody" downloaded from https://www.cancer.gov/publications/dictionaries/cancer-terms/def/antibody on Sep. 17, 2020 (Year: 2020).*
Lecture 32 Nanoimprint Lithography (NIL)—Overview and Thermal NIL resists, course ECE 695 Nanometer Scale Patterning and Processing, Spring 2016, Purdue University (Year: 2016).*
Gelest Safety Data Sheet for PP1-ZPUA, versin 1.0 2015 (Year: 2015).*
Garay et al., Surface plasmon resonance aided electrochemical immunosensor for CK—MB determination in undiluted serum samples, Anal Bioanal Chem. Jul. 2010 397(5): 1873-1881 (Year: 2010).*
Bei et al., "Immune responses to all ErbB family receptors detectable in serum of cancer patients," Oncogene (1999) 18, 1267-1275 (Year: 1999).*
Ali et al., "Plasmonic-Electrochemical Dual Modality Microfluidic Sensor for Cancer Biomarker Detection", MEMS Conference in Las Vegas, NV, 4 pages, Jan. 22, 2017.
Ali et al., "Integrated Dual-Modality Microfluidic Sensor for Biomarker Detection Using Lithographic Plasmonic Crystal", Lab on a Chip, 28 pages, Nov. 12, 2017.
Choi et al., "Fabrication and Characterization of a Dual-Mode SPR/SERS Sensor Based on Plasmonic Nanodome Arrays" Sensors, 4 pages, 2013.
Cinel et al., "Electron beam lithography designed silver nano-disks used as label free nano-biosensors based on localized surface plasmon resonance", Optics Espress, vol. 20, No. 3, pp. 2587-2597, Jan. 30, 2012.
Das et al., "Large-Scale Plasmonic nanoCones Array for Spectroscopy Detection", Applied Materials & Interfaces, vol. 7, pp. 23597-23604, 2015.
Eftekhari et al., "Nanoholes as Nanochannels: Flow-through Plasmonic Sensing", Anal. Chem, vol. 81, pp. 4308-4311, Jun. 1, 2009.
Escobedo, Carlos, "On-chip nanohole array based sensing: a review", Lab on a Chip, vol. 13, pp. 2445-2463, Mar. 6, 2013.
Forster, Robert, "Microelectrodes: New Dimensions in Electrochemistry", Royal Society of Chemistry, Issue 4, pp. 289-297 Jan. 1, 1994.
Fredriksson et al., "Hole-Mask Colloidal Lithography", Adv. Mater., vol. 19, pp. 4297-4302, 2007.

Gauchez et al., "Evaluation of a Manual ELISA Kit for Determination of HER2/neu in Serum of Breast Cancer Patients", Anticancer Research, vol. 28, pp. 3067-3074, 2008.
Haske et al., "65 nm feature sizes using visible wavelength 3-D multiphoton lithography", Optics Express, vol. 15, No. 6, pp. 3426-3436, Mar. 19, 2007.
Heinze, Jürgen, "Ultramicroelectrodes in Electrochemistry", Angew. Chem. Int. Ed Engl., vol. 32, pp. 1268-1288, 1993.
Heller et al., "Multimodal optical sensing and analyte specificity using single-walled carbon nanotubes", Nature Nanotechnology, vol. 4, pp. 114-120 Feb. 2009.
Hu et al., "Nanodevices in diagnostics", Wiley Interdiscip Rev Nanomed Nanobiotechnol., vol. 3(1), 35 pages, Jan. 2011.
Hu et al., "Ultrasensitive, Multiplexed Detection of Cancer Biomarkers Directly in Serum by Using a Quantum Dot-Based Microfluidic Protein Chip" ACS NANO, vol. 4, No. 1, pp. 488-494, Dec. 30, 2009.
Qbal et al., "Human Epidermal Growth Factor Receptor 2 (HER2) in Cancers: Overexpression and Therapeutic Implications", Molecular Biology International, vol. 2014, Article ID 852748, 9 pages, Sep. 7, 2014.
Jemal et al., "Cancer Statistics, 2008", CA Cancer J Clin., vol. 58, pp. 71-96, Mar. 2008.
Kim et al., "Localized surface plasmon resonance detection of layered biointeractions on metallic subwavelength nanogratings", Nanotechnology, vol. 20, 6 pages, Jul. 13, 2009.
Kondrashina et al., "A Phosphorescent Nanoparticle-Based Probe for Sensing and Imaging of (intra)Cellular Oxygen in Multiple Detection Modalities", Adv. Funct. Mater., vol. 22, pp. 4931-4939, 2012.
Li et al., "Monitoring the electrochemical responses of neurotransmitters through localized surface plasmon resonance using nanohole array", Biosensors and Bioelectronics, vol. 93, pp. 241-249, Aug. 30, 2016.
Li et al., "A paper-based microfluidic biosensor integrating zinc oxide nanowires for electrochemical glucose detection", Microsystems & Nanoengineering, vol. 1, 7 pages, Jul. 8, 2015.
Lu et al., "In situ synthesis of palladium nanoparticle-graphene nanohybrids and their application in nonenzymatic glucose biosensors", Biosensors and Bioelectronics, vol., 26, pp. 3500-3504, Feb. 2, 2011.
Malhotra et al., "Ultrasensitive Detection of Cancer Biomarkers in the Clinic using a nanostructured Microfluidic Array", Anal. Chem., vol. 84(14), pp. 6249-6255, Jul. 17, 2012.
Marinakos et al., "Plasmonic Detection of a Model Analyte in Serum by a Gold Nanorod Sensor", Anal. Chem., vol. 79, pp. 5278-5283, Jul. 15, 2007.
Mondal et al., "Highly Sensitive Biofunctionalized Mesoporous Electrspun TiO2 Nanofiber Based Interface for Biosensing", ACS Appl. Mater. Interfaces, vol. 6, 2516-2527, Jan. 21, 2014.
Nyberg, Morgan, "Dual-Modality Probe for Prostate Cancer Detection by Combining Raman Spectroscopy and Tactile Resonance Technology", Lulea Univ. of Tech, Graphic Production, 132 pages, 2013.
Oh et al., "Carbon Nanotube-Based Dual-Mode Biosensor for Electrical and Surface Plasmon Resonance Measurements", Nano Lett., vol. 10, pp. 2756-2760, Jul. 6, 2010.
Pan et al., "An electrochemical biosensor to simultaneously detect VEGF and PSA for early prostate cancer diagnosis based on grahene oxide/ssDNA/PLLA nanoparticles", Biosensors & Bioelectronics, vol. 89, pp. 598-605, 2017.
Powers et al., "Protein analytical assays for diagnosing, monitoring, and choosing treatment for cancer patients", J Healthc Eng., vol. 3(4), pp. 503-534, Dec. 2012.
Sainsbury et al., "Epidermal-Growth-Factor Receptor Status as Predictor of Early Recurrence of and Death from Breast Cancer", The Lancet, 5 pages, Jun. 20, 1987.
Sainsbury et al., "Epidermal-Growth-Factor Receptor Status as Predictor of Early Recurrence of and Death from Breast Cancer", The Lancet, 3 pages, Feb. 16, 1985.
Sandison et al., "Nanofabrication of electrode arrays by electron-beam and nanoimprint lithographies", Lab on a Chip, vol. 6, pp. 1020-1025, Jun. 21, 2006.

(56) References Cited

OTHER PUBLICATIONS

Scholder et al., "Helium focused ion beam fabricated plasmonic antennas with sub-5 nm gaps", Nanotechnology, vol. 24, 7 pages, Sep. 6, 2013.
Smolensky et al., "Magnetoluminescent Light Switches—Dual Modality in DNA Detection", JACS, vol. 135, pp. 8966-8972, May 21, 2013.
Stern et al., "Label-free biomarker detection from whole blood", Nat. Nanotechnol., vol. 5(2), pp. 138-142, Feb. 2010.
Stewart et al., "Nanostructured Plasmonic Sensors", Chem Rev., vol. 108, pp. 494-521, Jun. 2, 2007.
Tabassum et al., "Plasmonic Crystal-Based Gas Sensor Toward an Optical Nose Design", IEEE Sensors Journal, vol. 17, No 19, pp. 6210-6223, Oct. 1, 2017.
Truong et al., "Nanopost plasmonic crystals", Nanotechnology, vol. 20, 15 pages, Oct. 2, 2009.
Venkatesan et al., "Nanopore sensors for nucleic acid analysis", Nature Nanotechnology, 10 pages, Sep. 18, 2011.
Vilela et al., "Carbon Nanotubes Press-Transferred on PMMA Substrates as Exclusive Transducers for Electrochemical Microfluidic Sensing", Analytical Chemistry, vol., 84, pp. 10838-10844, Nov. 21, 2012.
Wang et al., "Electrically Tunable Quasi-3-D Mushroom Plasmonic Crystal", Journal of Lightwave Technology, vol., 34, No. 9, pp. 2175-2181, May 1, 2016.
Xia et al., "Label-free Dual-Analyte Electrochemical Biosensors: A New Class of Molecular-Electronic Logic Gates", JACS, vol. 132, pp. 8557-8559, Feb. 16, 2010.
Yang et al., "Selective Nanofiber Deposition Using a Microfluidic Confinement Approach", Langmuir, vol. 26(3), pp. 1539-1543, Dec. 17, 2009.
Yu et al., "Multiplex Biosensor Using Gold Nanorods", Analytical Chemistry, vol. 79, No. 2, pp. 572-579, Jan. 15, 2007.
Zhang et al., "ErbB receptors: from oncogenes to targeted cancer therapies", The Journal of Clinical Investigation, vol. 117, No. 8, pp. 2051-2058, Aug. 2007.
Zheng et al., "Multiplexed electrical detection of cancer markers with nanowire sensor arrays", Nature Biotechnology, vol. 23, No. 10, pp. 1294-1301, Oct. 2005.

* cited by examiner

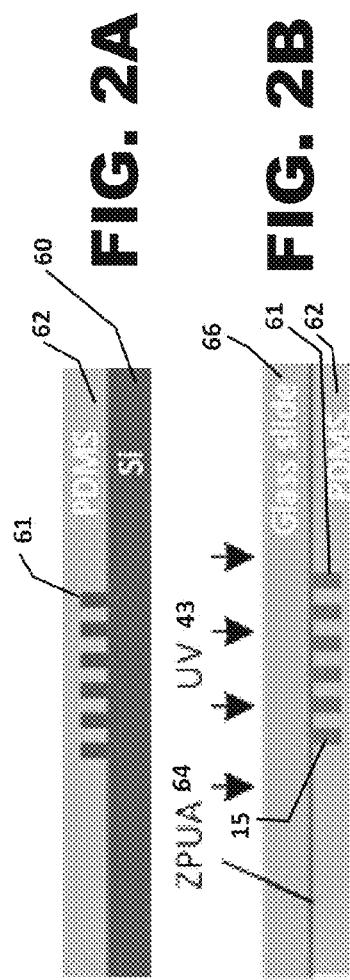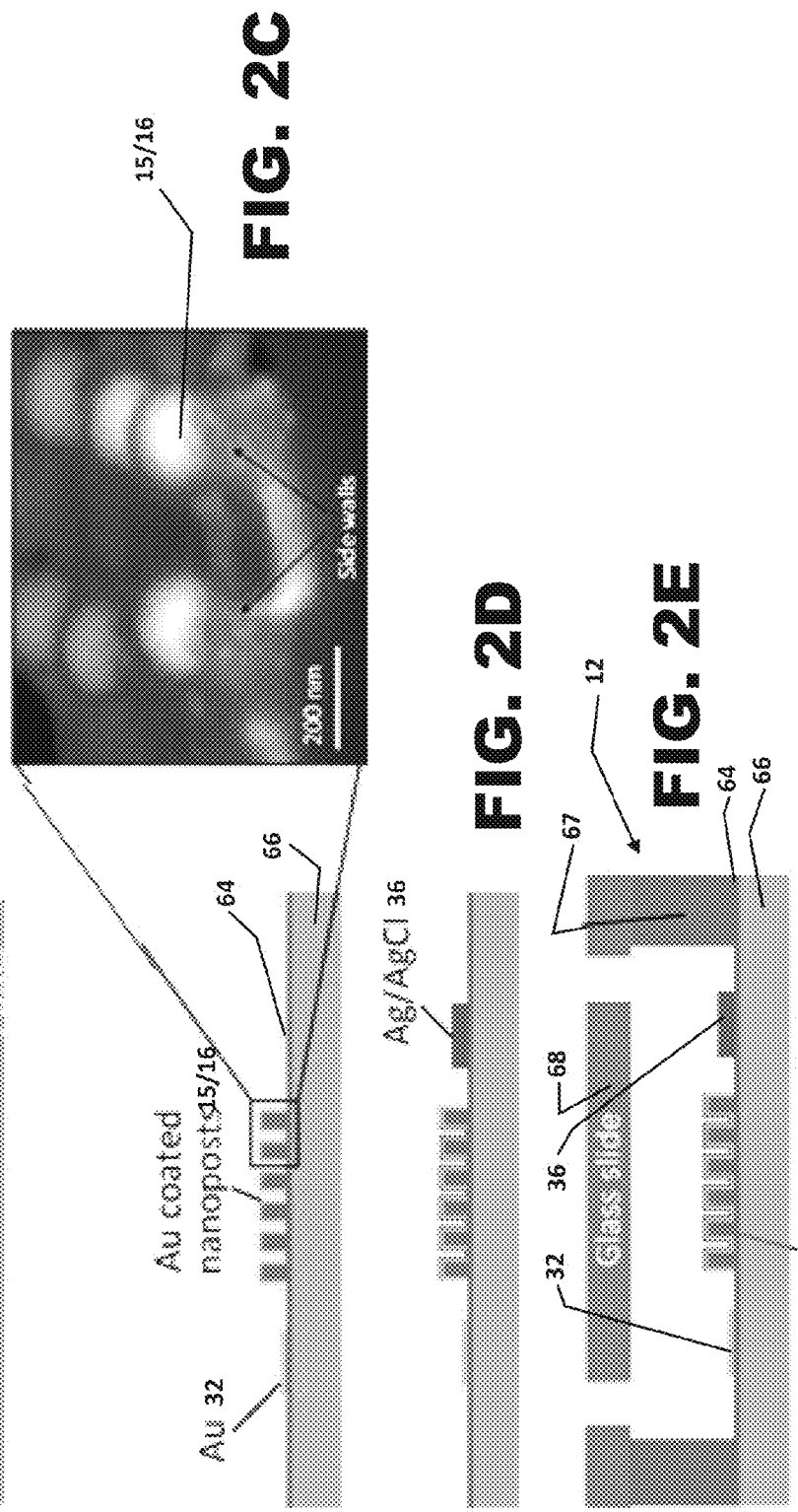

(SENSOR RESPONSES FOR DIFFERENT ErbB2 CONCENTRATIONS FOR SENSOR WITH NANOPOSTS ACCORDING TO THE INVENTION)

(SENSOR RESPONSES FOR DIFFERENT ErbB2 CONCENTRATIONS FOR SENSOR WITHOUT NANOPOSTS OF THE INVENTION)

INTEGRATED DUAL-MODALITY MICROFLUIDIC SENSOR FOR BIOMARKER DETECTION USING LITHOGRAPHIC PLASMONIC CRYSTAL

CROSS-REFERENCE TO RELATED APPLICATIONS

This application claims the benefit of Provisional Application U.S. Ser. No. 62/620,025, filed on Jan. 22, 2018, all of which is herein incorporated by reference herein in its entirety.

GRANT REFERENCE

This invention was made with government support under NSF Contract No. CCF1331390. The Government has certain rights in this invention.

I. BACKGROUND OF THE INVENTION

A. Field of the Invention

The present invention relates to biosensors and, in particular, to small scale yet sensitive sensors.

B. Problems in the State of the Art

Much work is occurring in this technological area. The ability for accurate detection and quantification of biological species has much promise. However, the variety of factors involved in biosensing can be extremely complicated and unpredictable.

There is a need in the art for relatively small scale biosensors that are accurate and provide multiple modalities, but do not require relatively large sample volumes.

For example, attempts to detect such things a DNA hybridization, anti-body-antigen interactions, and other biological interactions have added receptors to the surface of carbon nanotubes. Monitoring the carbon nanotubes for conductance changes can be indicative of target analytes binding to the receptors. While some of these attempts have reported label-free detection, real-time monitoring, and high sensitivity, practical applications have been limited because of issues of sensor-to-sensor variation and unspecific binding.

One attempt to overcome the foregoing problems proposed not only measuring electrical conductance changes but simultaneously also optically measuring changes in surface plasmon resonance (SPR). The different measurement techniques are complimentary. SPR sensors have relatively low sensitivity but relatively high reliability. Thus, acquisition of both measurements simultaneously can provide higher reliability than nanotube conductance alone but take advantage of its high sensitivity. See, for example, Oh, et al., *Carbon Nanotube-Based Dual-Mode Biosensor for Electrical and Surface Plasmon Resonance Measurements.* Nano Lett. 2010, 10, 2756-2760 which is incorporated by reference herein in its entirety, which grows or deposits a layer of carbon nanotubes (CNT) on a transparent substrate (e.g. quartz). This allows electrical measurements because of the electrical characteristics of the CNT but also optical measurements because of the transparency of the quartz.

Despite the foregoing, the inventors have recognized there is room for improvement in this area. For example, biofunctionalizing a grown or deposited layer of CNT has limitations regarding the uniformity and reproducibility of such sensing surfaces.

II. SUMMARY OF THE INVENTION

A. Objects, Features, Advantages

It is therefore an object, feature or advantage of the present invention to provide methods, systems, and apparatus of biosensing which address the problems in the state-of-the-art.

Other objects, features, or advantages of the invention relate to methods, systems, and apparatus which:

(a) Provide for relatively inexpensive fabrication of high uniformity 3D nanostructures for presentation of increased surface area and radial diffusion of analyte across the bio-functionalized sensing area as compared to other dual-mode techniques such as CNT grown or deposited on a transparent substrate for improved performance by high uniformity in size, shape, and distribution.

(b) Provide for improved reproducibility performance of such sensing surfaces, including in mass production.

(c) Allow for simultaneous acquisition of dual modality measurements from a smaller footprint, shared sensing area with lower sample consumption.

(d) Allow for improved detection reliability.

(e) Leverages high sensitivity of detection with dynamic tracking of antigen-antibody interactions, enzymatic reactions, or aptamer-based reactions (e.g., aptamer-cleavage reactions) at the sensing surfaces.

Other objects, features, and advantages of the invention will become apparent with reference to the accompanying specification.

B. Aspects of the Invention

In one aspect of the invention, essentially a lab-on-a-chip presents a sensing area of micro scale. A periodic array of nanoposts are coated with a noble metal and graphene oxide (GO) and are biofunctionalized with an anti-body for a target biological marker. Utilization of a precise fabricated array of nanoposts with those coatings is combined with taking simultaneous electrochemical and surface plasmon resonance (SPR) measurements once a sample volume is conveyed to the sensing surface. This can be by microfluidics.

The biofunctionalization binds the target biomarkers to the nanoposts. Having both electrochemical and SPR measurements from the same minute sensing area allows comparison and quantification of both detection and concentration of the biomarker of interest.

The relatively inexpensive fabrication of nanoposts by known MEMS processes also produces highly reproducible uniformity of the nanoposts. This provides high reproducibility in addition to increased surface area, good radial diffusion of liquid phase analyte during measurement, and effective simultaneous electrochemical and SPR signals with relatively small sample volumes.

In one aspect, the biomarker of interest relates to cancer. The invention is not limited to such. Other examples include, but are not limited to, biomarkers for diseases such as chronic leukemias, some lymphomas, etc., and also biomarkers for drug screening.

III. BRIEF DESCRIPTION OF THE DRAWINGS

Examples of some forms the invention can take will be described with reference to the appended drawings, which are incorporated by reference to this description and are summarized below.

The patent or application file contains at least one drawing executed in color. Copies of this patent or patent application publication with color drawing(s) will be provided by the Office upon request and payment of the necessary fee.

FIG. 1 is a schematic representation of an integrated dual modality microfluidic sensor chip for the detection of cancer biomarkers. Zoomed-in images in (a) shows the antibody immobilization at plasmonic nanoposts via covalent interactions wherein —COOH groups are present at the GO-Au nanoposts that can facilitate immobilization of anti-ErbB2 via forming amide bonds with —$NH_2$ groups of anti-ErbB2. (b) Integrated dual-modality sensor operation showing coupling of light and voltage sources in a single nanopost to generate SPR and electrochemical signals.

FIGS. 2A-E are a step-wise representation for the fabrication of integrated dual modality sensor. Inset of (c) shows the SEM image for the Au coating on the sidewalls of nanoposts.

Figure 2F:
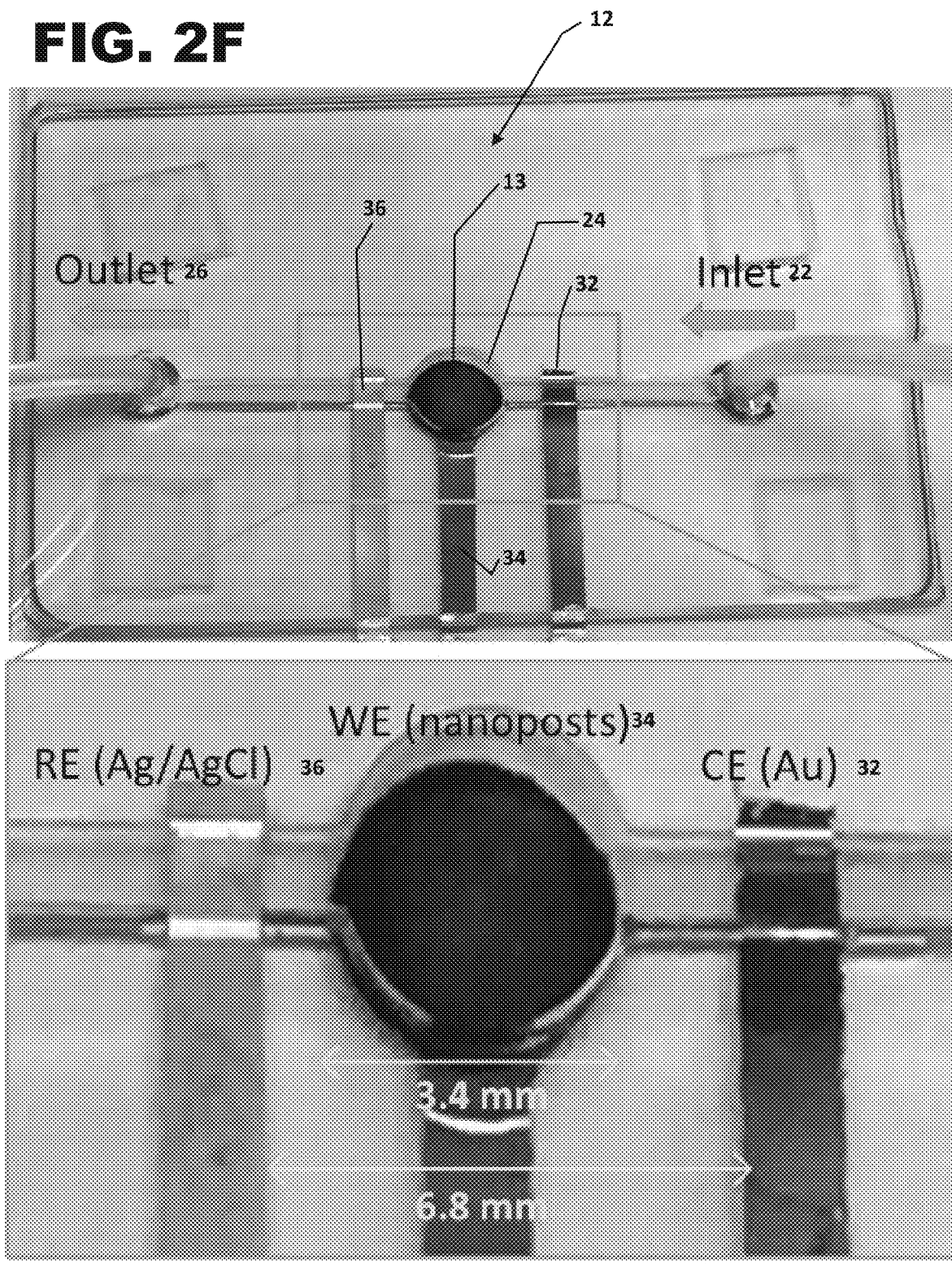
Figure 2G:
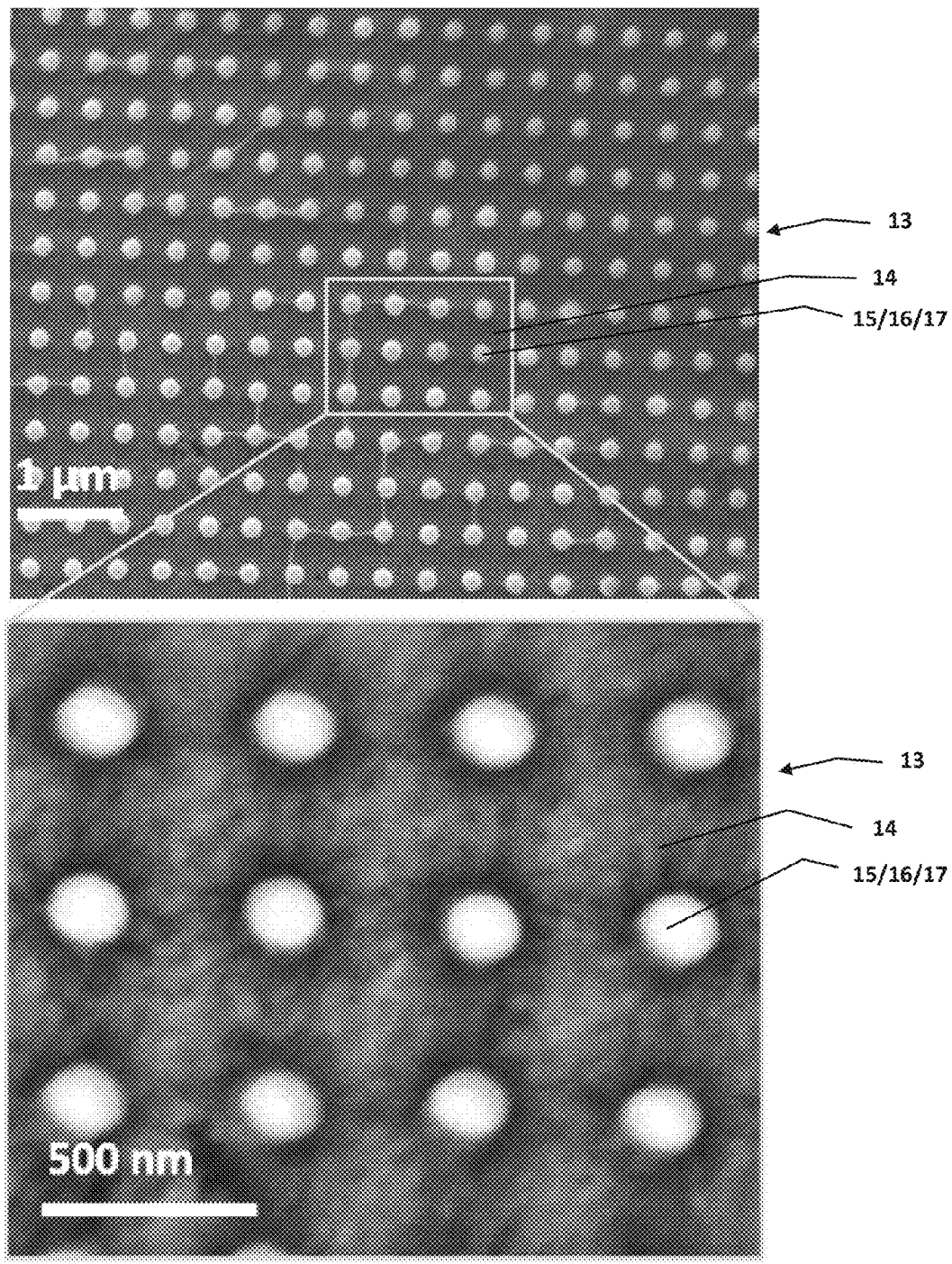
Figure 2H:
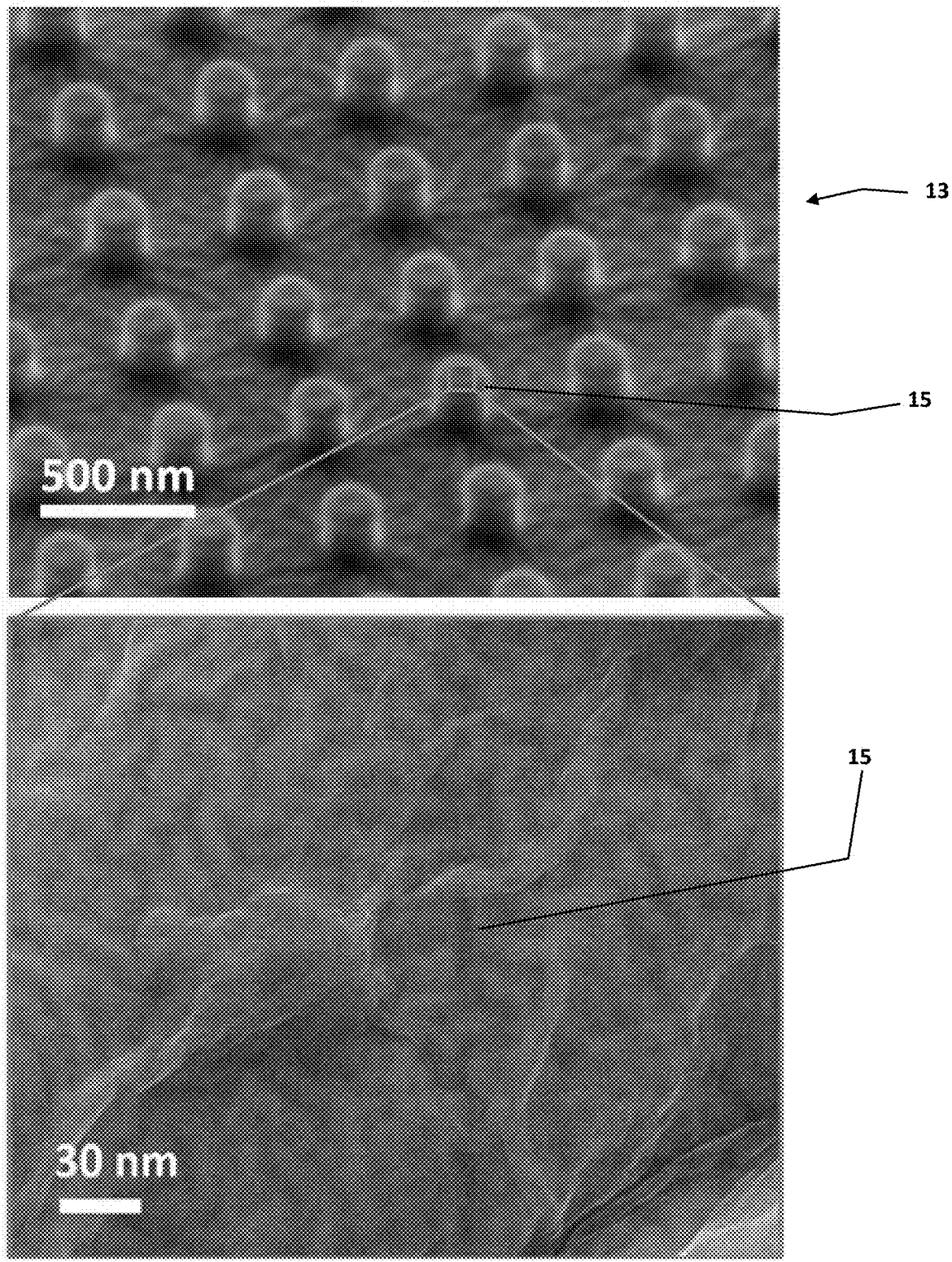

FIGS. 2F-H include a photograph of the fabricated integrated dual-modality sensor chip of FIGS. 2A-E. Inset shows a zoomed-in image. FIG. 2G is a top-view SEM image of the GO-Au nanoposts electrode on a glass substrate. Inset shows a zoomed-in image. FIG. 2H is a SEM image of fabricated 3D GO/Au plasmonic nanoposts array. Inset shows the zoomed-in top-view SEM image of a single GO/Au nanopost.

Figure 3A:
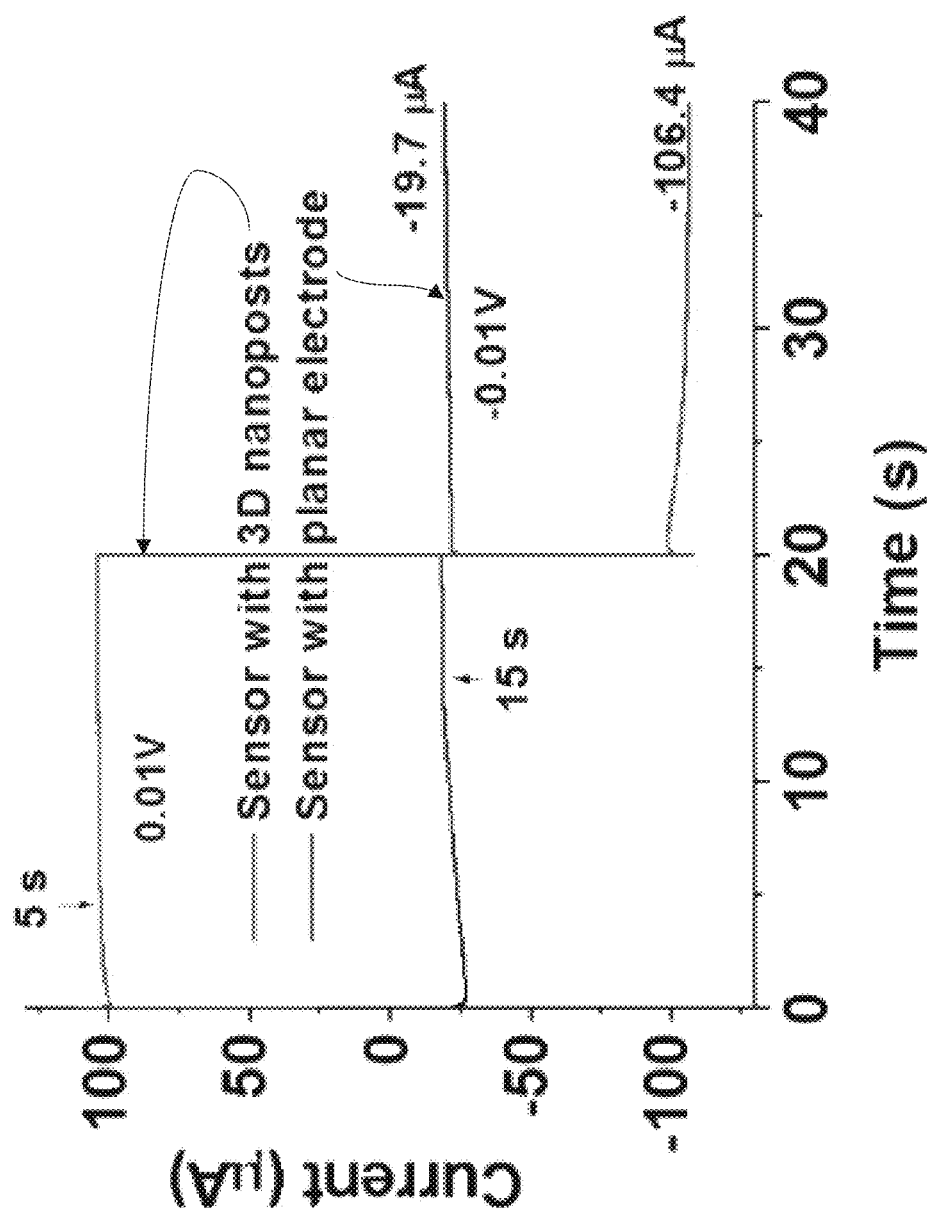
Figure 3B:
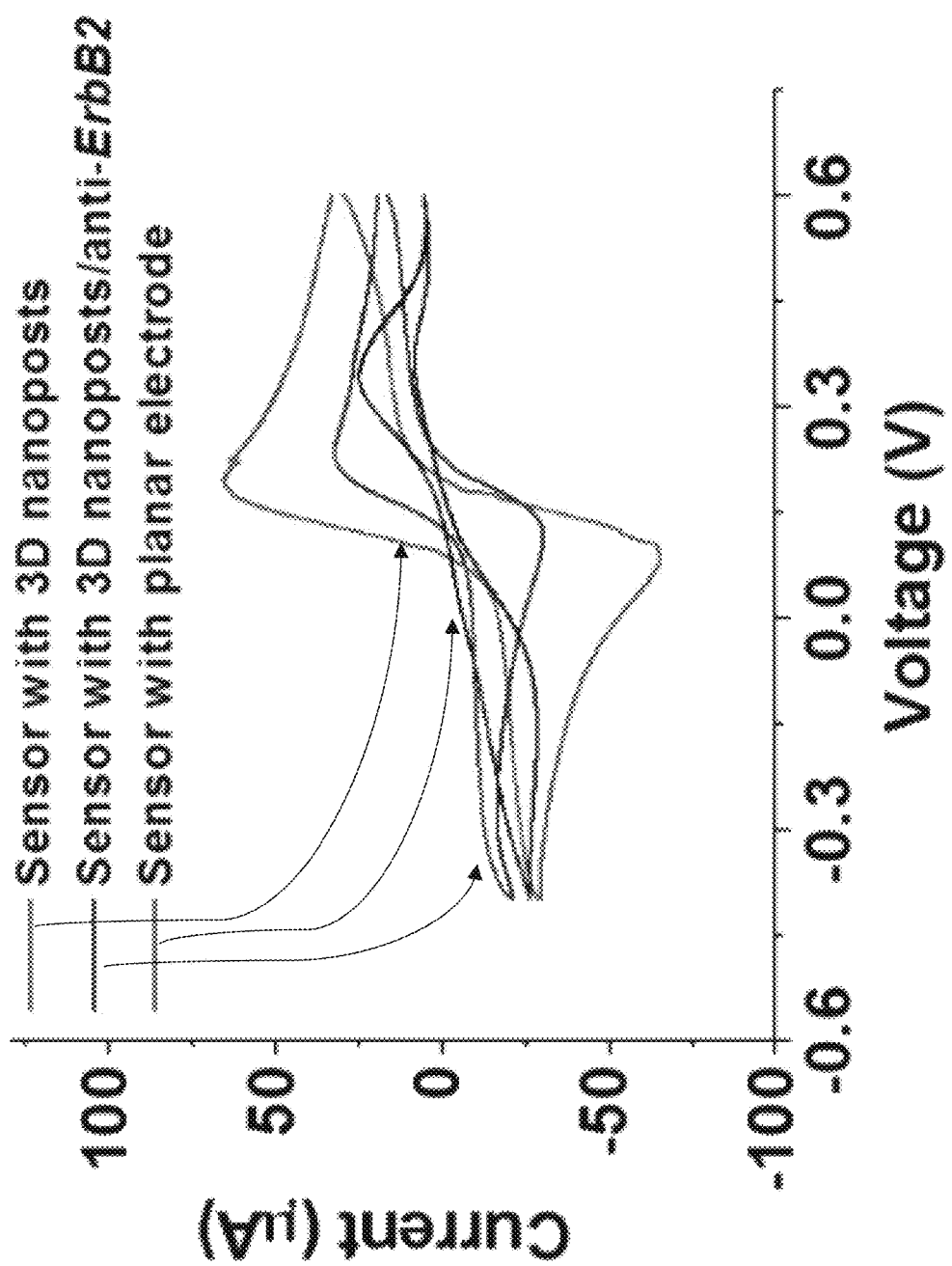
Figure 3C:
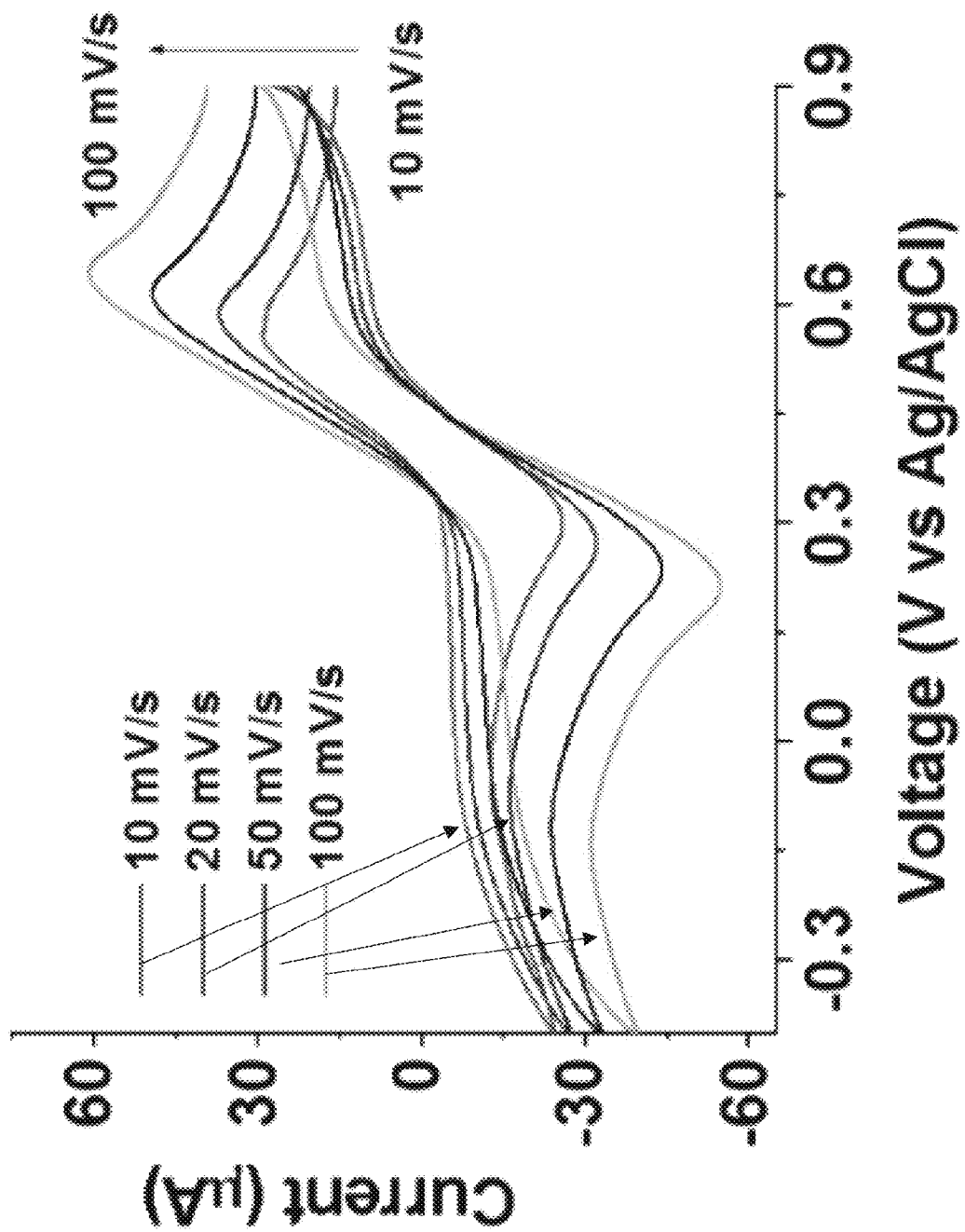
Figure 3D:
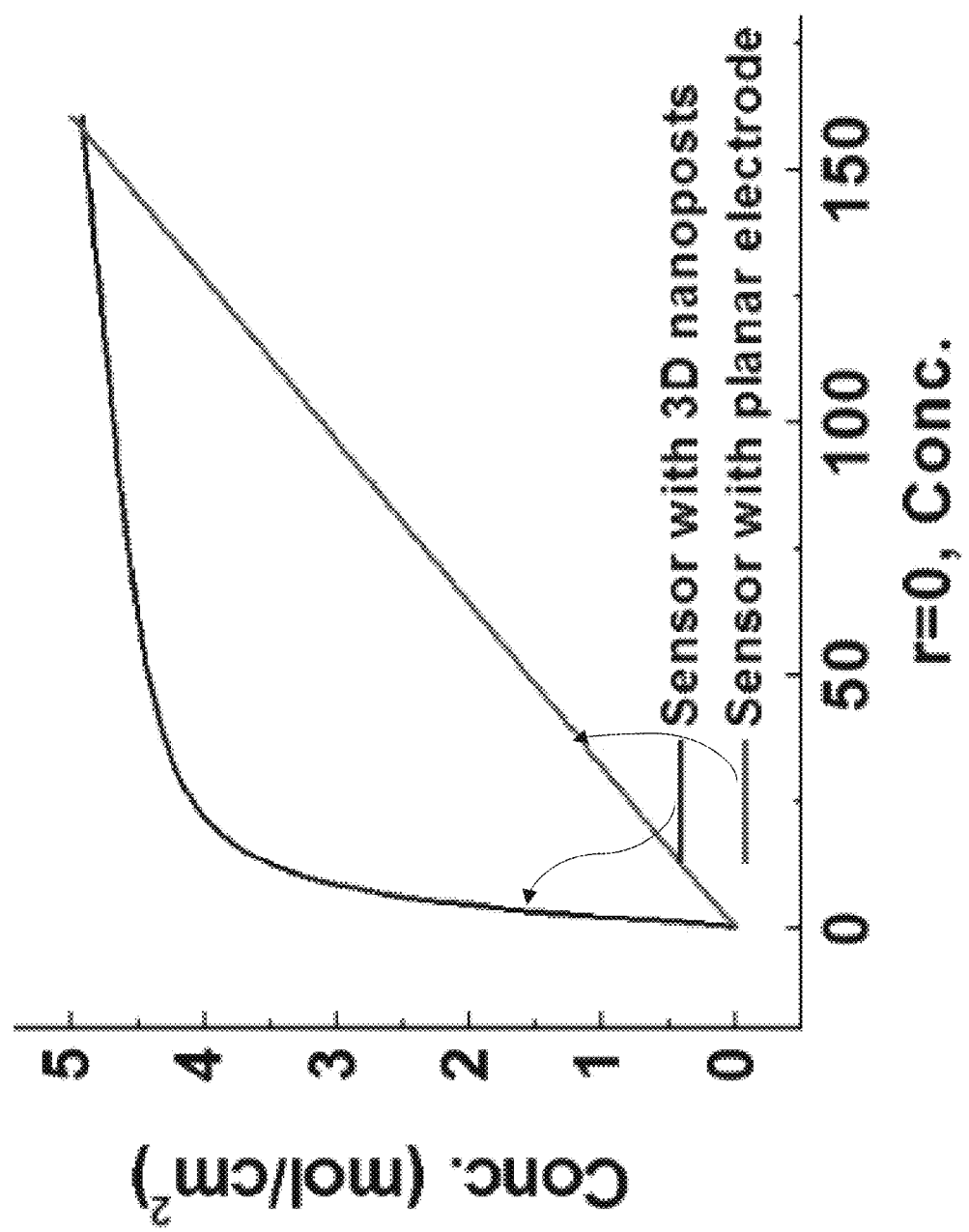
Figure 3E:
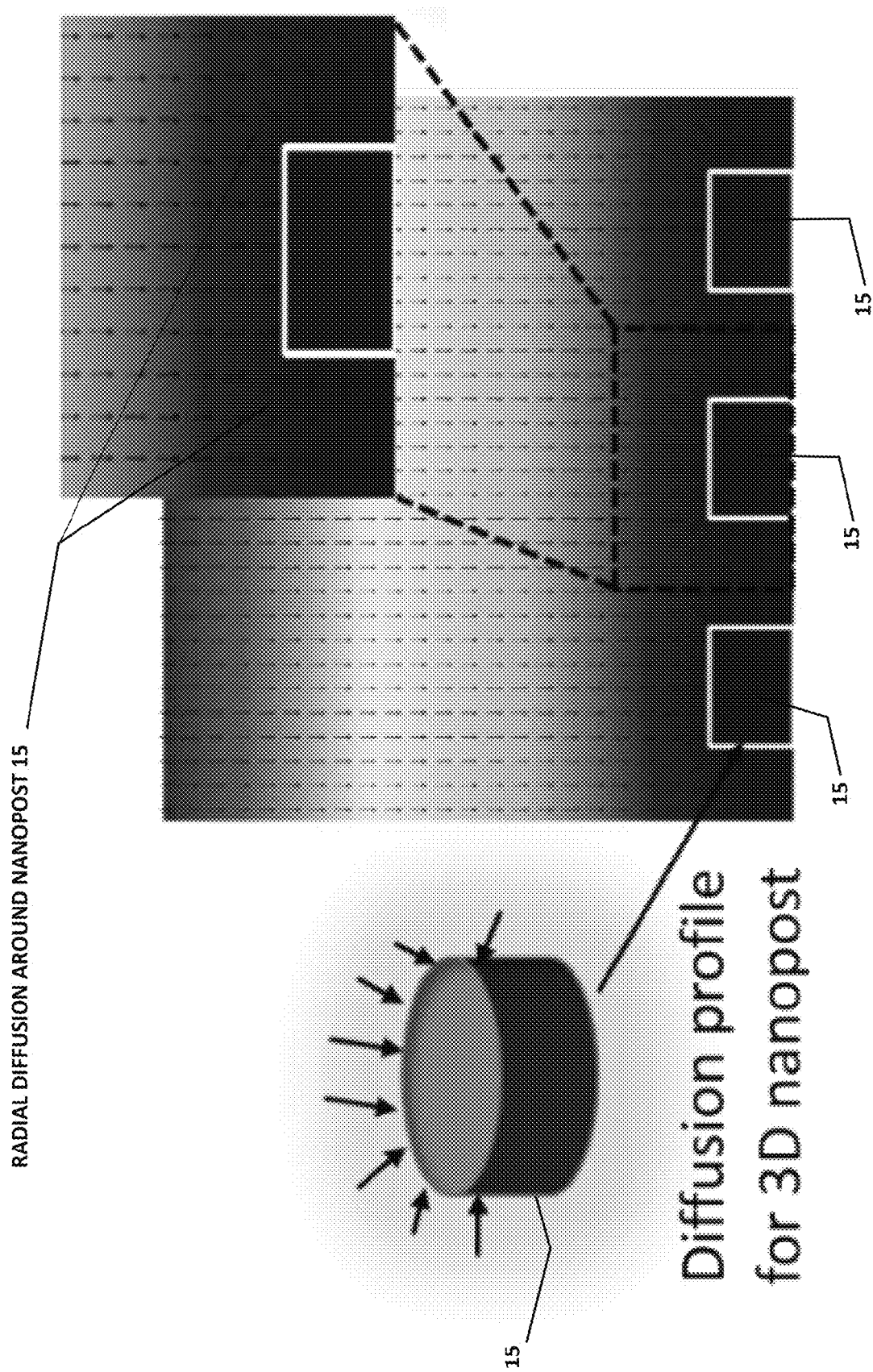
Figure 3F:
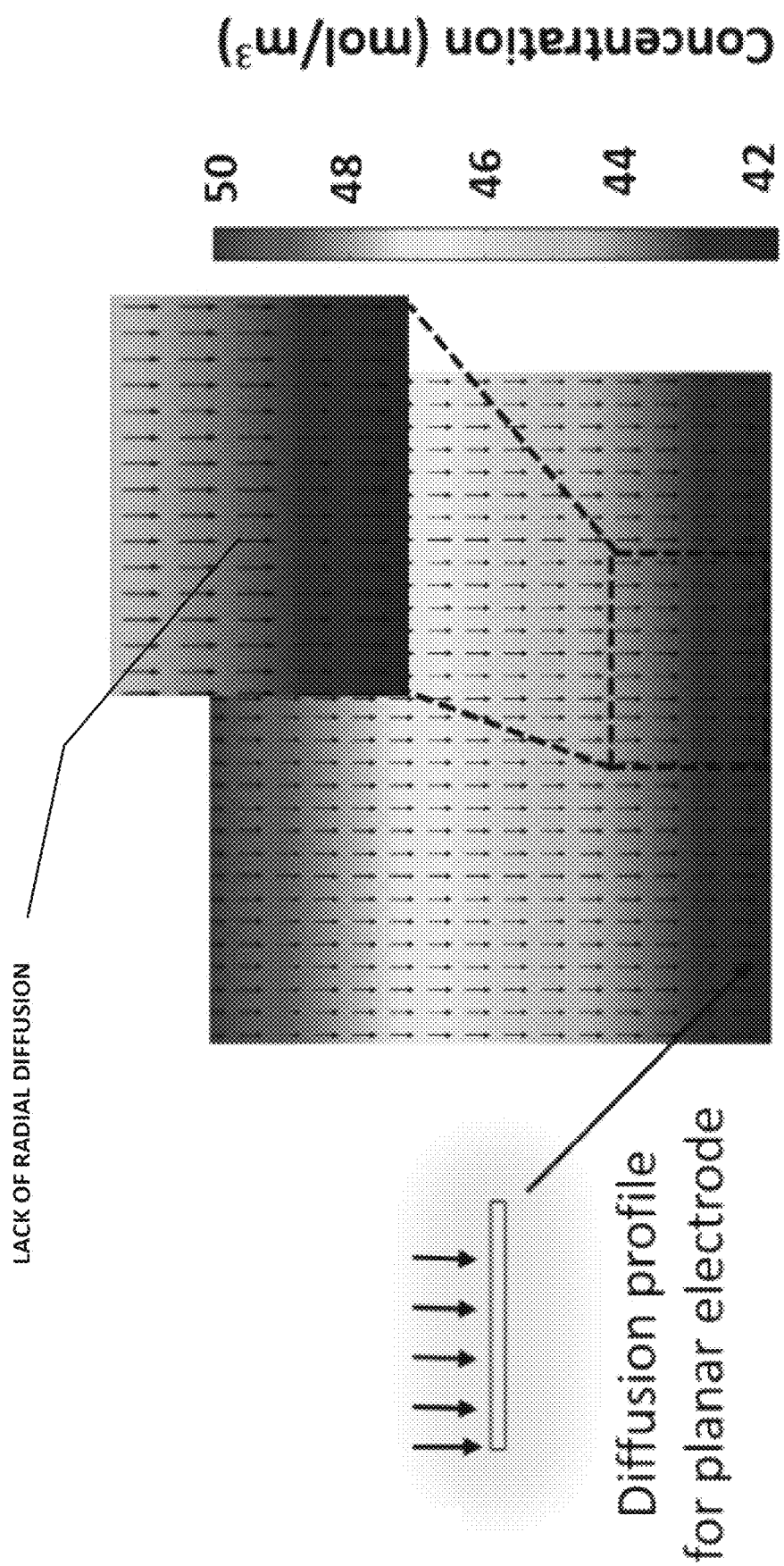

FIGS. 3A-F include: At FIG. 3A CA responses of the sensor with the nanoposts (GO-Au electrode) and without nanoposts (planar electrode) in PBS containing a 5 mM equimolar concentration of $[Fe(CN)_6]^{3-/4-}$ redox mediator. At FIG. 3B CV responses for the planar electrode, and the nanoposts-based electrode without and with antibody. At FIG. 3C CV responses of the nanoposts-based sensor (anti-ErbB2/GO-Au) as a function of scan rate. At FIG. 3D Concentration profiles of redox species diffusion near the 3D and planar electrodes. At FIGS. 3E and 3F Simulated diffusion profiles of redox species to the nanoposts-based electrode (FIG. 3E) and the planar electrode (FIG. 3F).

Figure 4A:
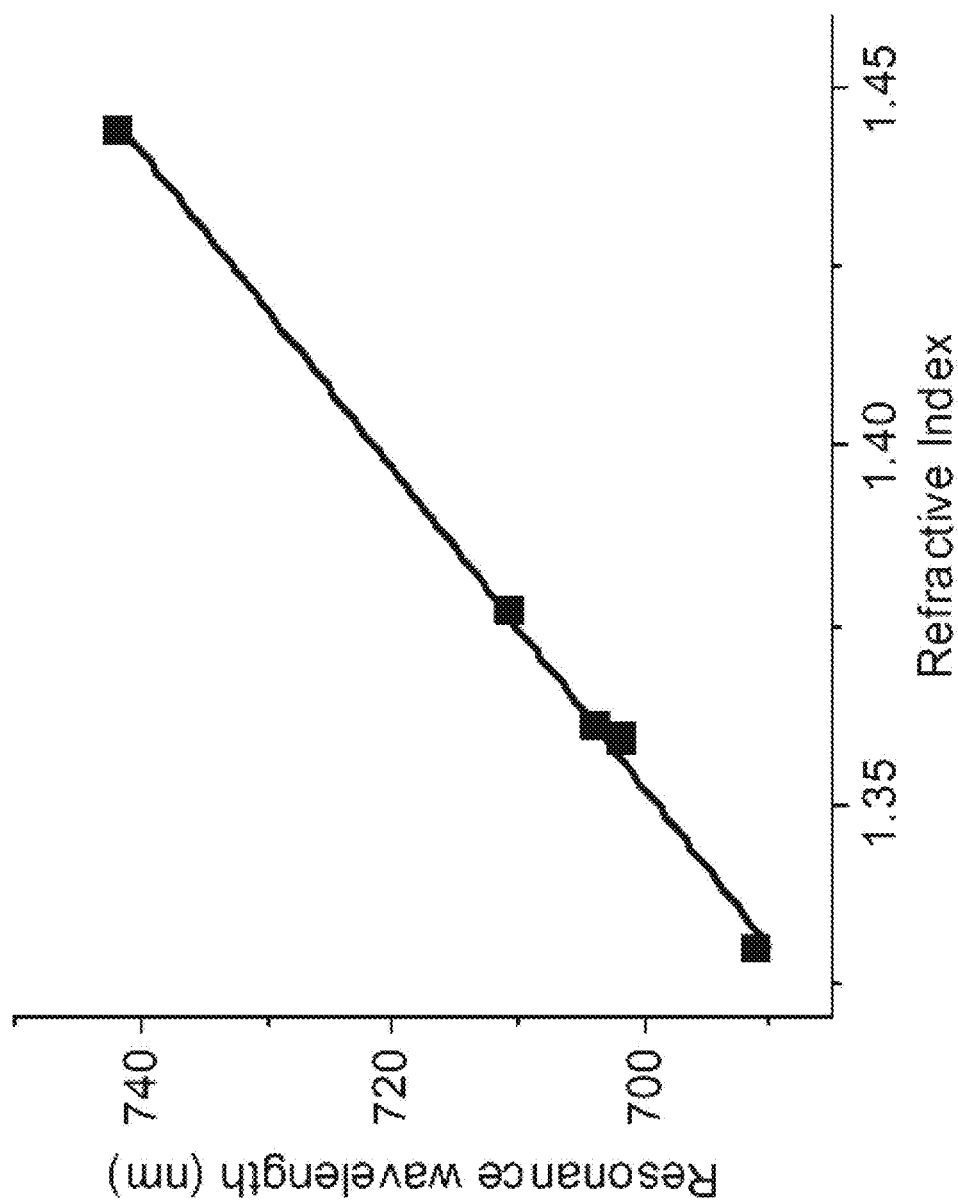
Figure 4B:
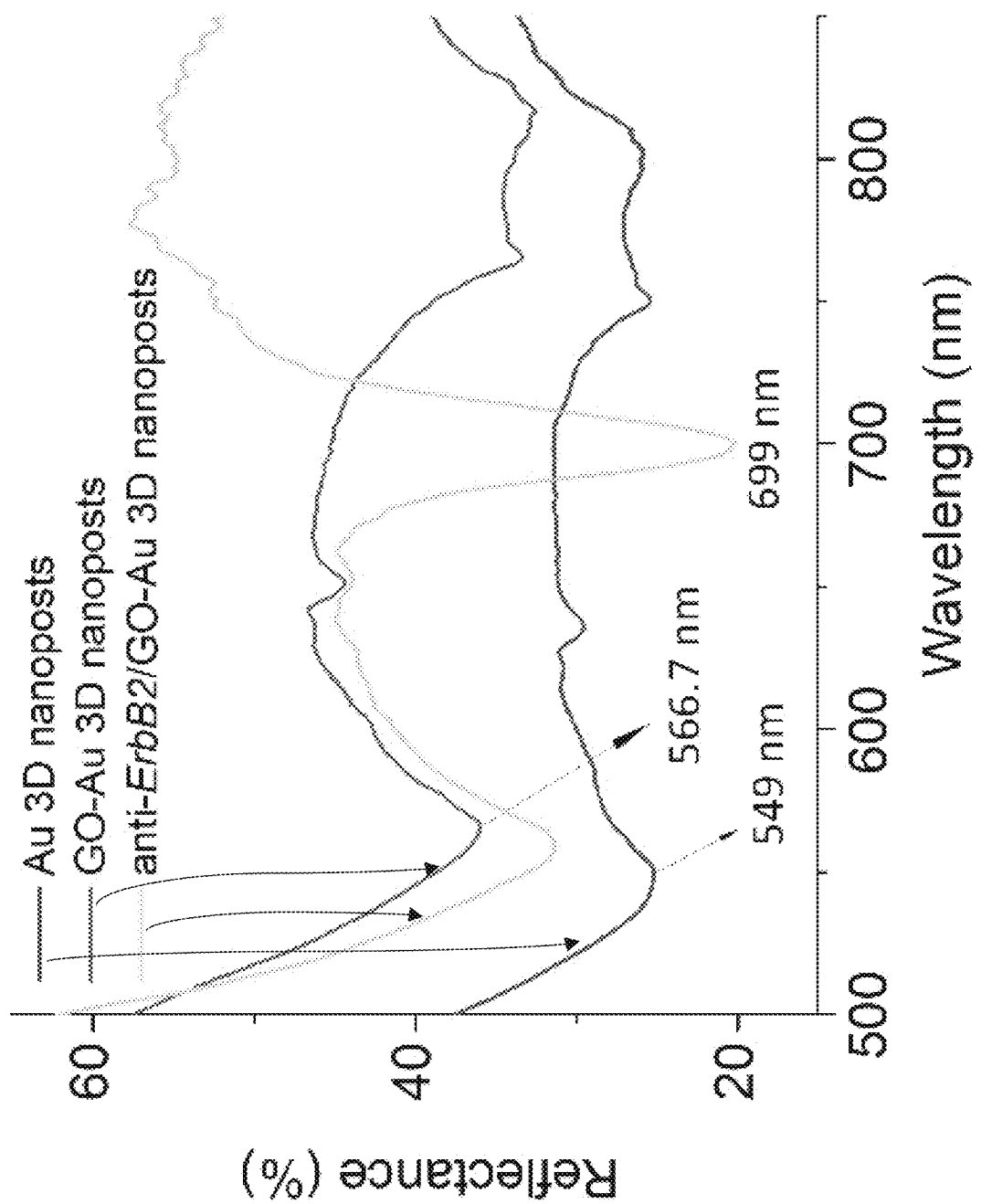
Figure 4C:
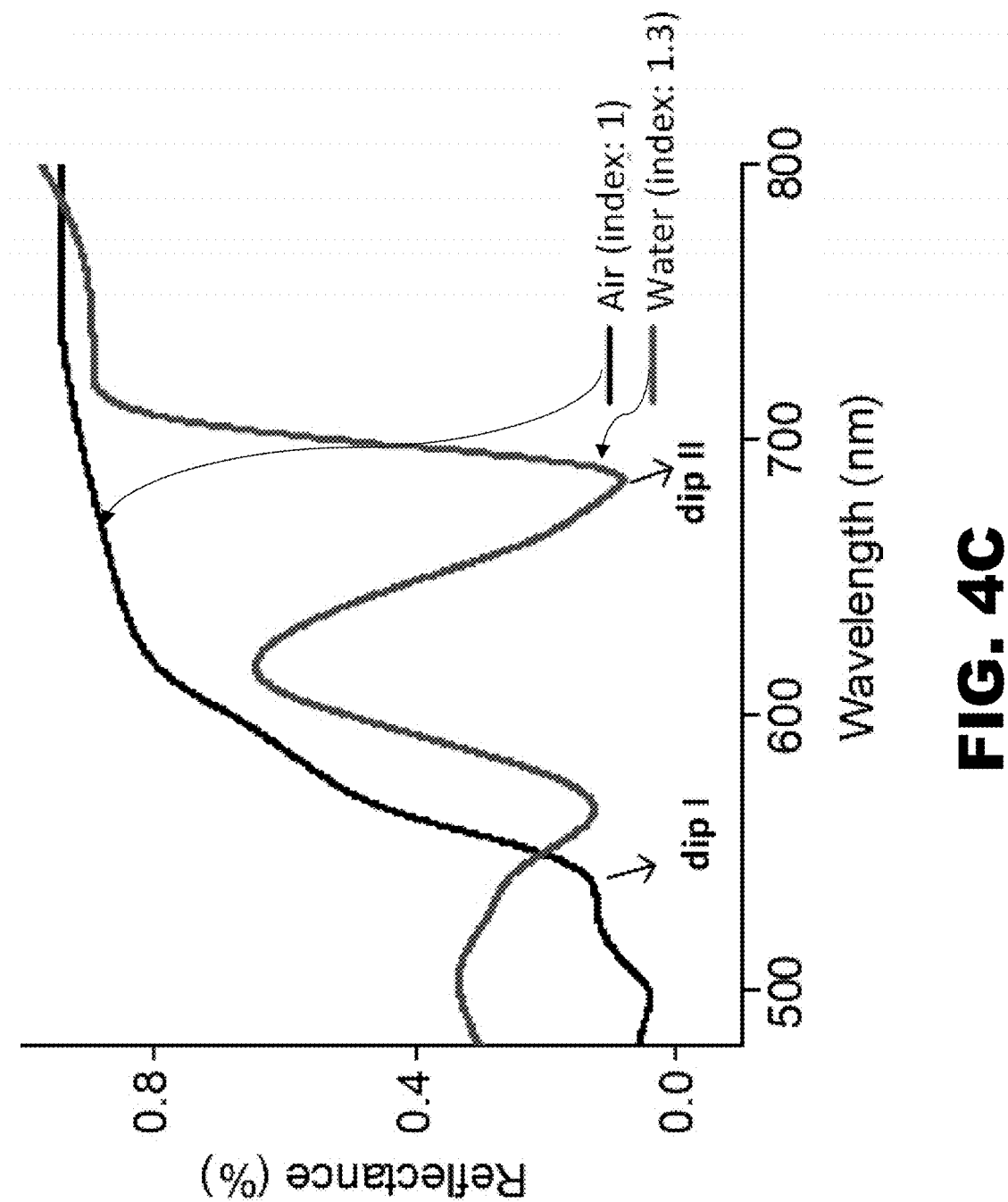

FIGS. 4A-D include: At FIG. 4A, bulk refractive index sensitivity of the plasmonic crystal in presence of various index materials. At FIG. 4B, SPR responses showing a redshift of 17.7 nm in air after coating the Au nanoposts with GO. After anti-ErbB2 immobilization on GO-Au nanoposts, the resonance is redshifted to 699 nm. At FIG. 4C, simulated reflectance spectra of the plasmonic nanostructures without GO in air (refractive index: 1) and water (refractive index: 1.3). The SPR resonances are denoted as dip I and II. At FIG. 4D, simulated cross-sectional electric field distributions at the resonances (dip I and II) in (FIG. 4C).

Figure 5A:
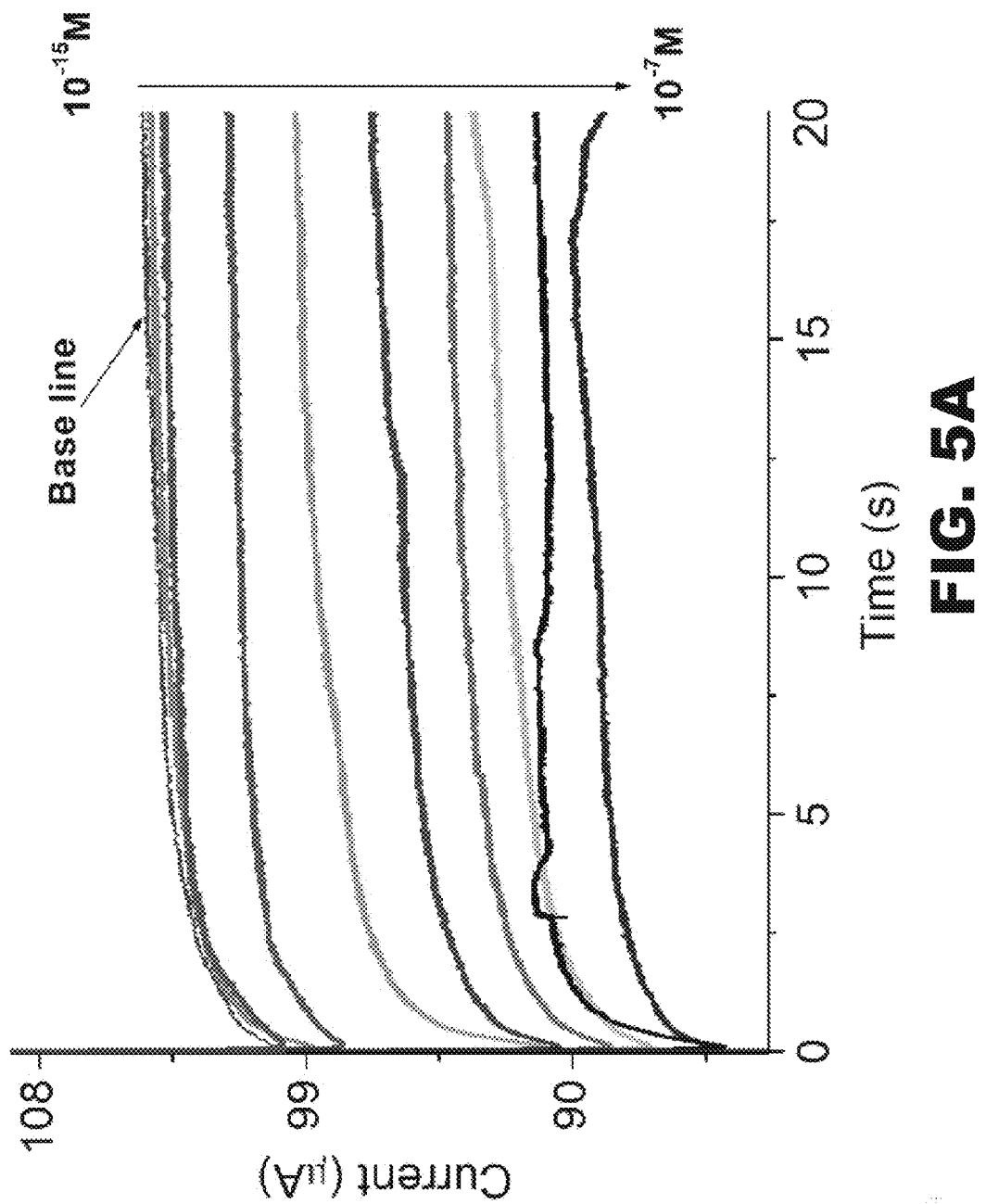
Figure 5B:
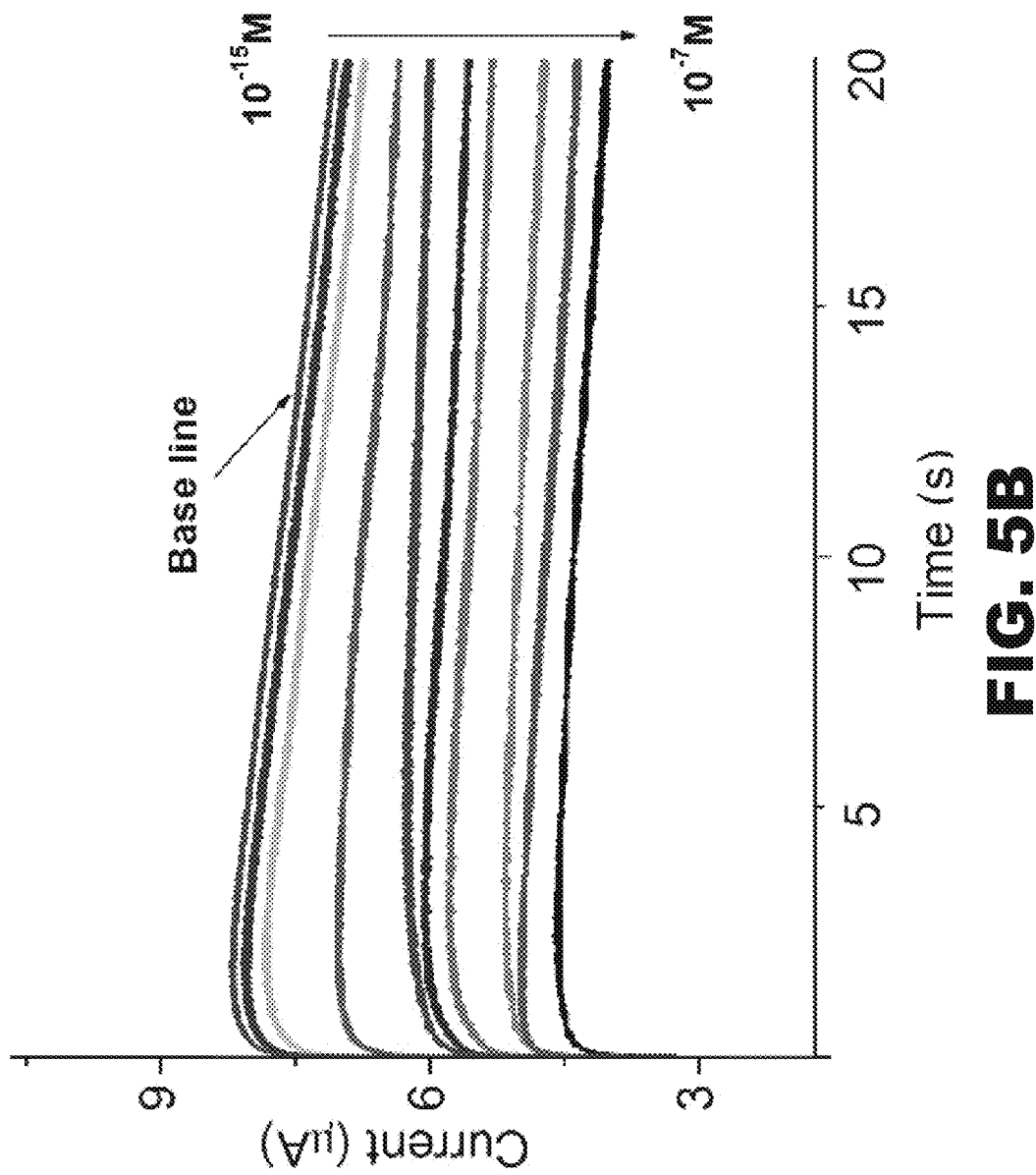

FIGS. 5A-F include: AT Sensing responses for the sensors with and without incorporating nanoposts. The measurements were conducted as a function of ErbB2 concentration at a constant sensing potential of 0.01 V in presence of PBS (pH 7.4) containing 5 mM $[Fe(CN)_6]^{3-/4-}$. At FIG. 5A, CA responses for the sensor with the nanoposts. At FIG. 5B, CA responses for the sensor with the planar Au electrode. At FIG. 5C, calibration plots for both the sensor responses in (FIG. 5A) and (FIG. 5B). Error bars represent three repeated measurements of the sensor. At FIG. 5D, selectivity test of the sensor in presence of specific ErbB2 (0.1 μM) and nonspecific ErbB3 (0.1 μM) and ErbB4 (0.1 μM). Inset shows the current responses versus several interferents. At FIG. 5E, reproducibility test of the sensor conducted.

FIGS. 6A-D include: At FIG. 6A, full SPR spectra of the GO coated Au nanopost array by varying the ErbB2 concentration from $1 \times 10^{-11}$ M to $1 \times 10^{-7}$ M. At FIG. 6B, SPR resonance wavelengths as a function of ErbB2 concentrations. The error bars represent the standard deviations obtained using five independent measurements. At FIG. 6C, stability test of the sensor at 1 nM ErbB2 concentration over four weeks, showing the resonance wavelength of the sensor as a function of time. Error bars represent the standard deviations obtained using four identical sensors that respond to 1 nM concentration of ErbB2 biomarker once a week over a four-week period. At FIG. 6D, transient response for detection of ErbB2 at the concentrations 10 pM, 0.1 nM, 1 nM, 10 nM and 0.1 μM showing association and dissociation phases for antigen-antibody interactions in the PBS (pH=7.4) solution.

Figure 7A:
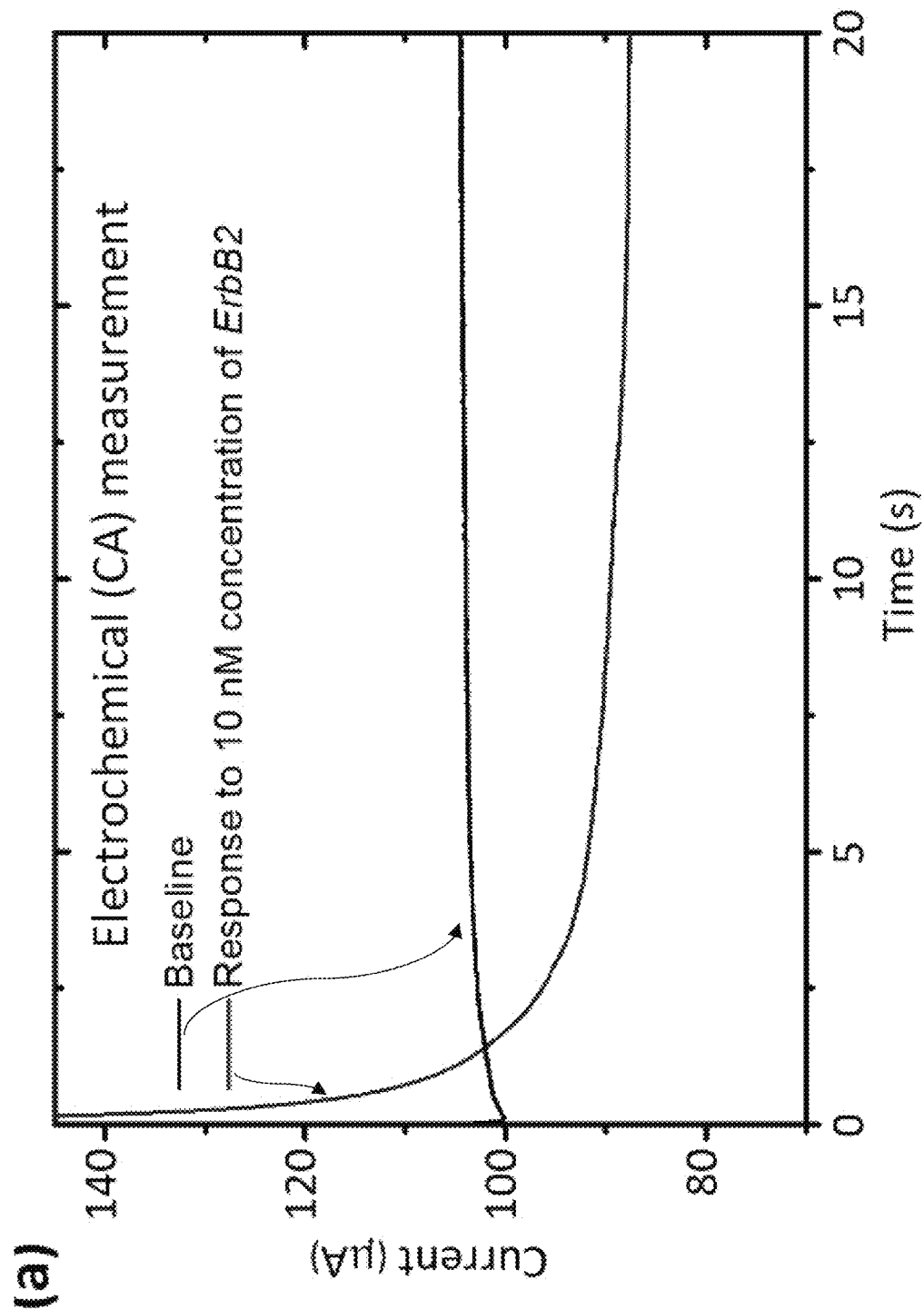

FIGS. 7A and B. Simultaneous measurements using the CA-based electrochemical (FIG. 7A) and SPR-based optical (FIG. 7B) methods on the single dual-modality sensor. The sensor was exposed to 10 nM concentration of ErbB2 molecules.

FIGS. 8A-E. Schematic representations of the main steps for 3D GO-Au nanoposts, Ag/AgCl and Au electrodes into a microfluidic channel using in-situ liquid phase polymerization process. (At FIG. 8E) Photograph of the fabricated sensor with microfluidic channel and tubes for liquid flow.

Figure 9:
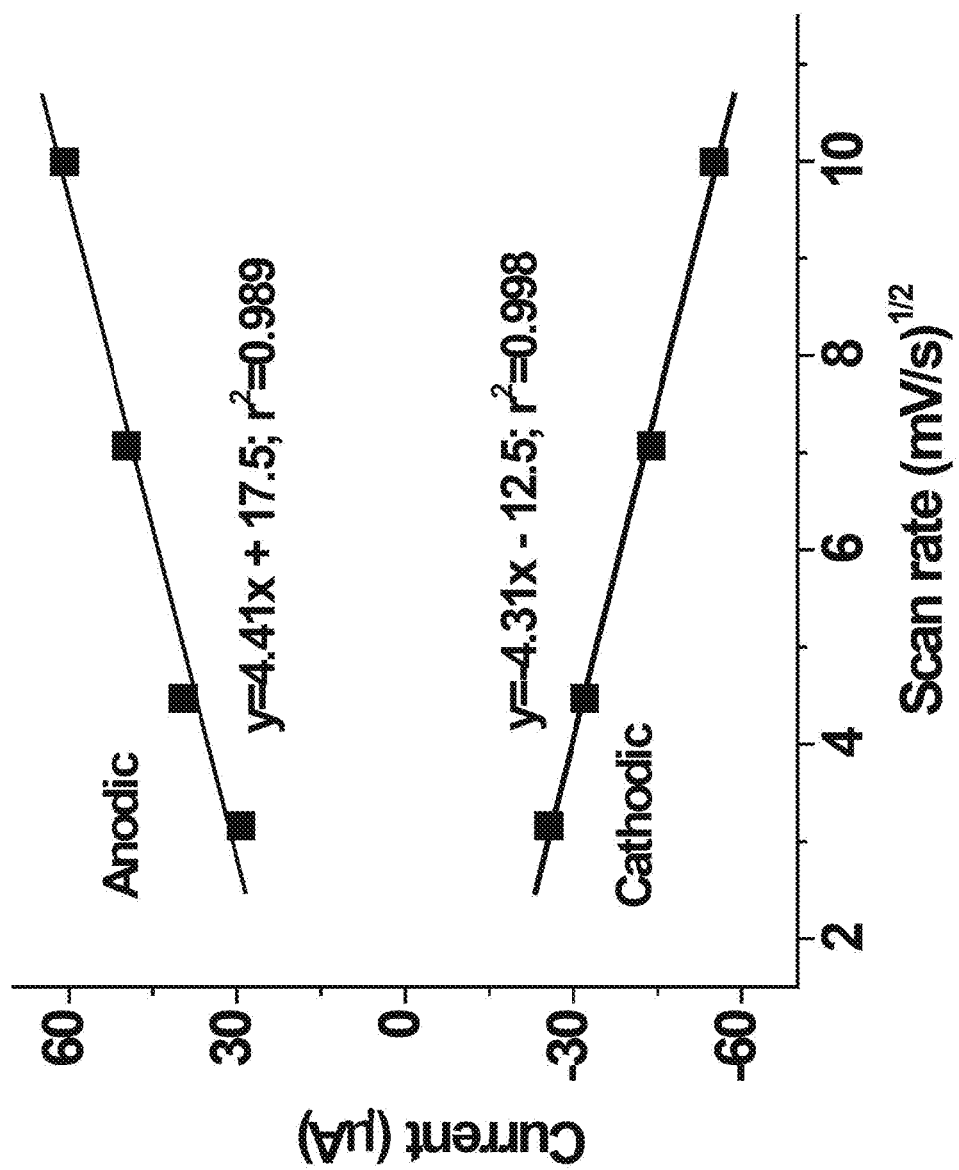

FIG. 9. The plot showing the current vs root square of scan rate (10-100 mV/s) for anodic and cathodic peak currents.

Figure 10:
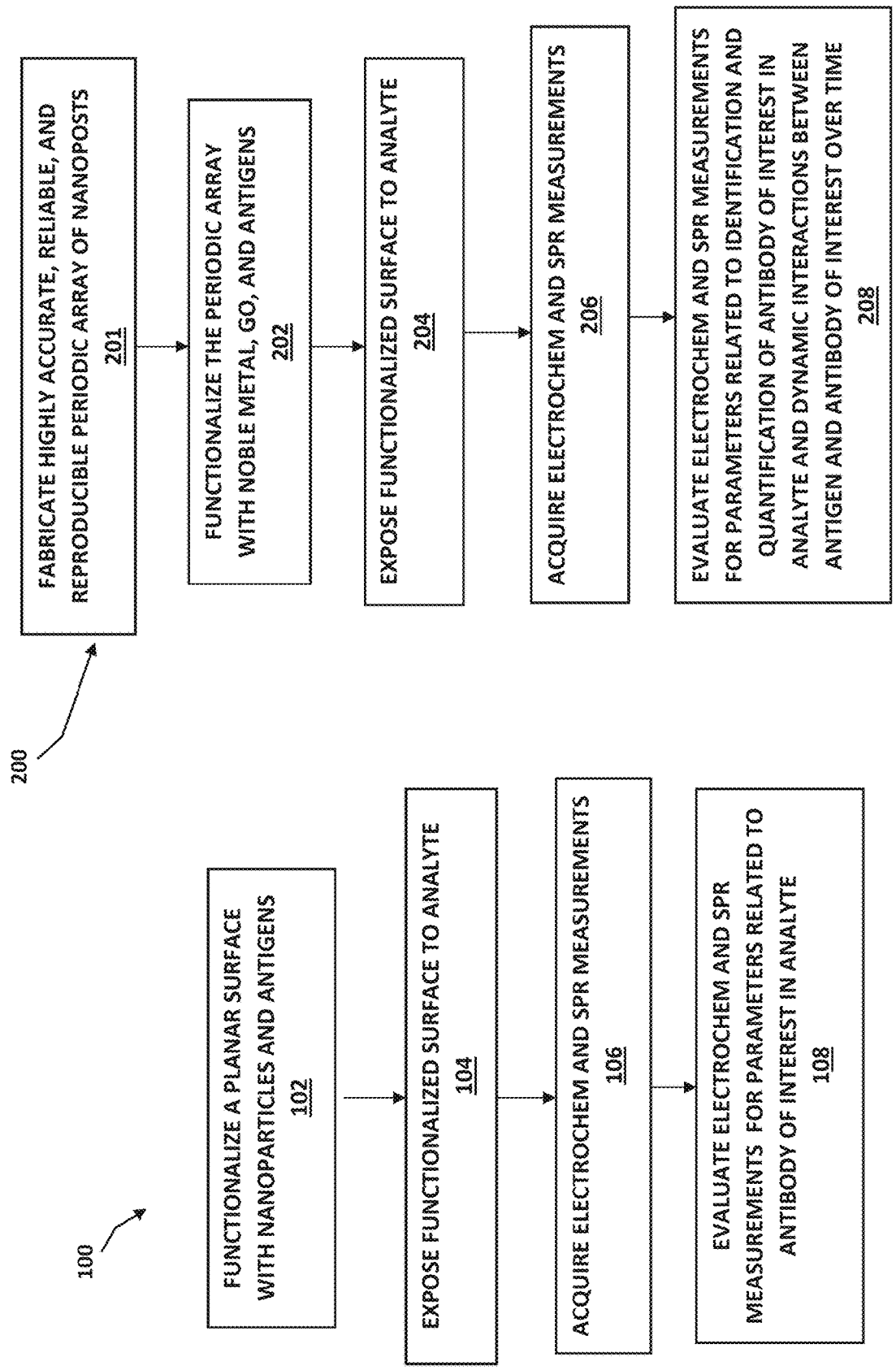

FIGS. 10A and B are simplified flow charts of one prior art method of dual mode sensing (FIG. 10A) versus aspects of the invention (FIG. 10B).

Figure 11:
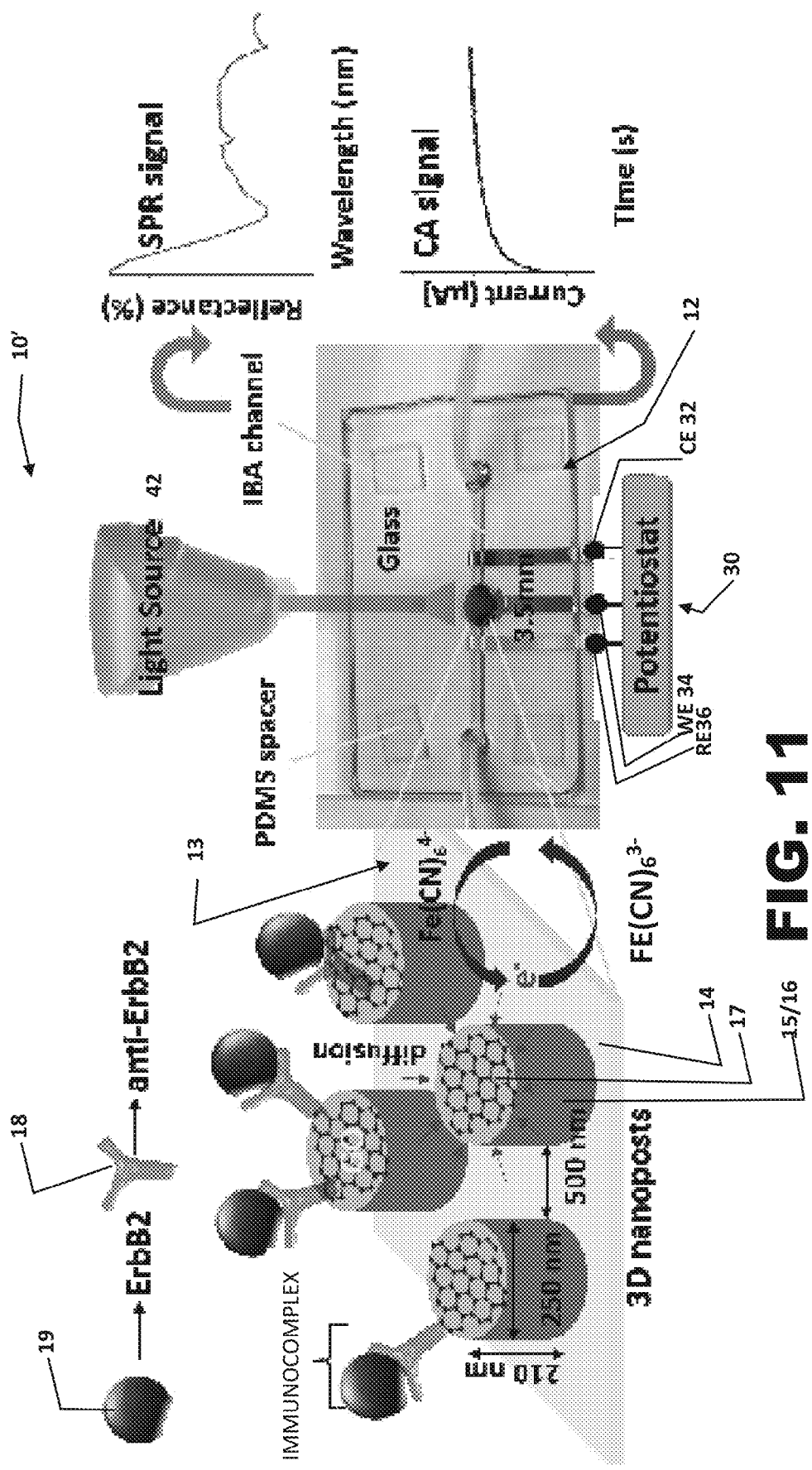

FIG. 11: A pictorial image of a dual-modality microfluidic immunosensor for the detection of cancer biomarkers. —COOH groups are present at GO sheets that can facilitate in-situ immobilization of anti-ErbB2 via forming amide bonds with —$NH_2$ groups of anti-ErbB2.

Figure 12A:
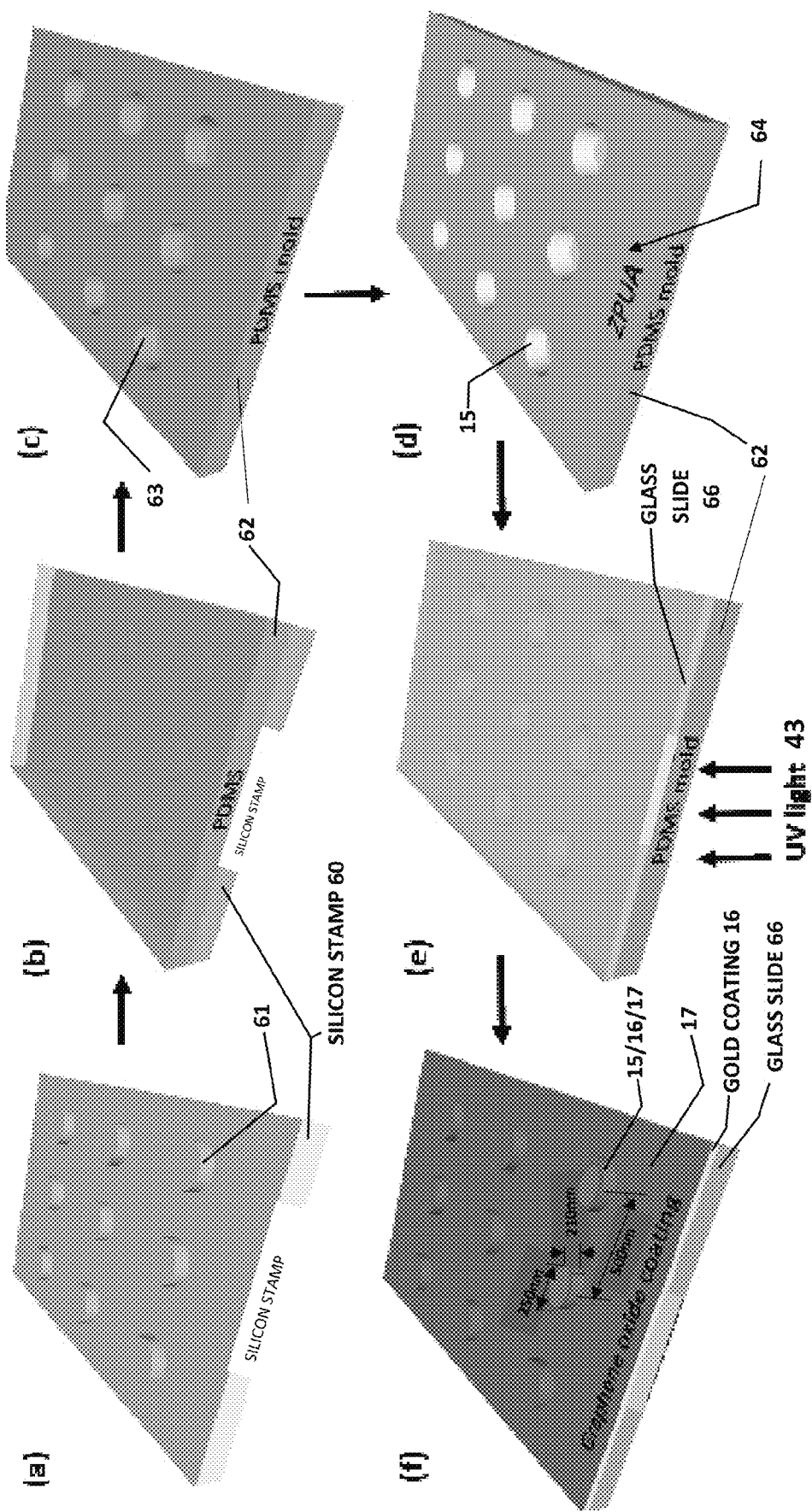
Figure 12B:
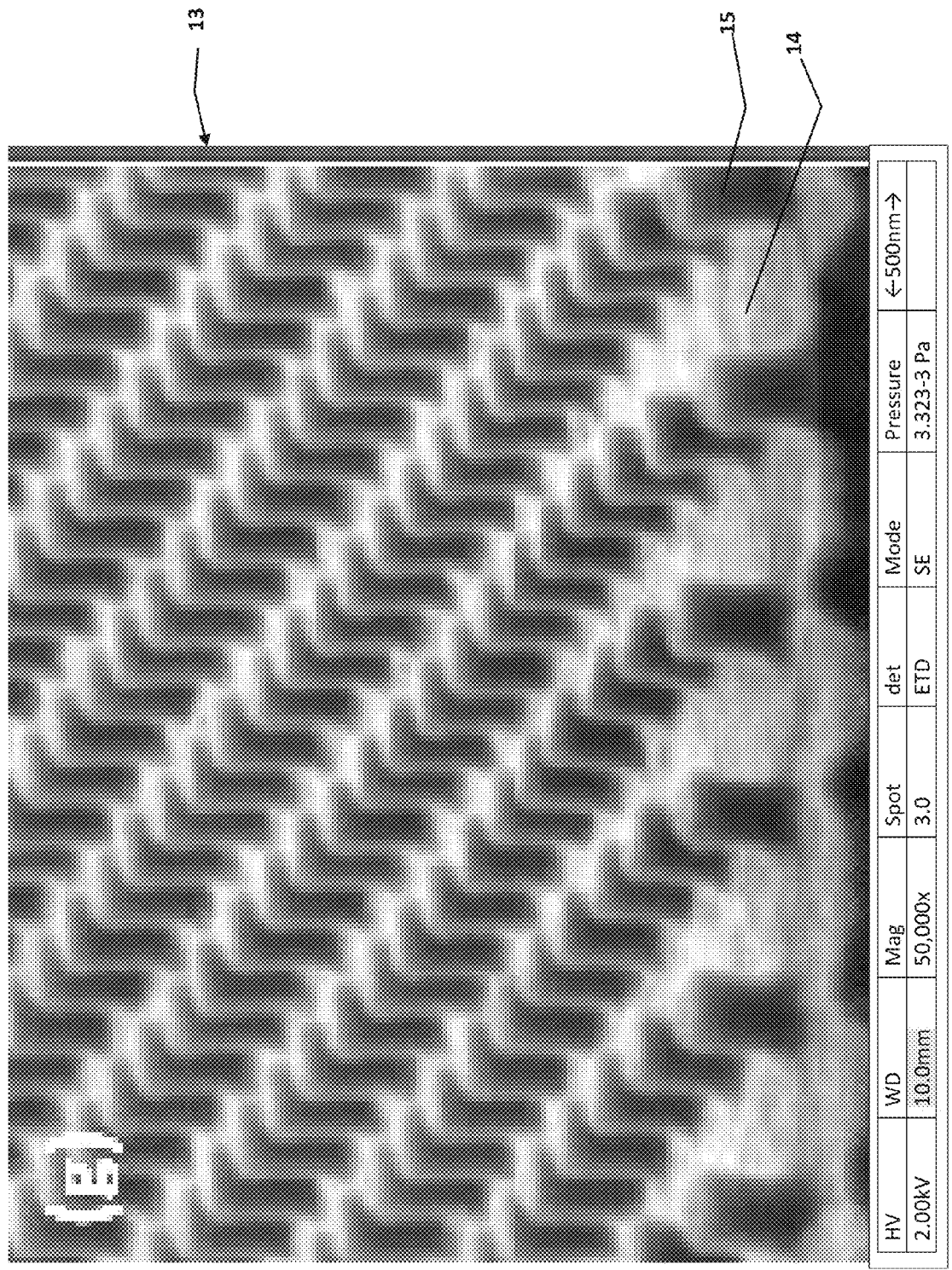
Figure 12C:
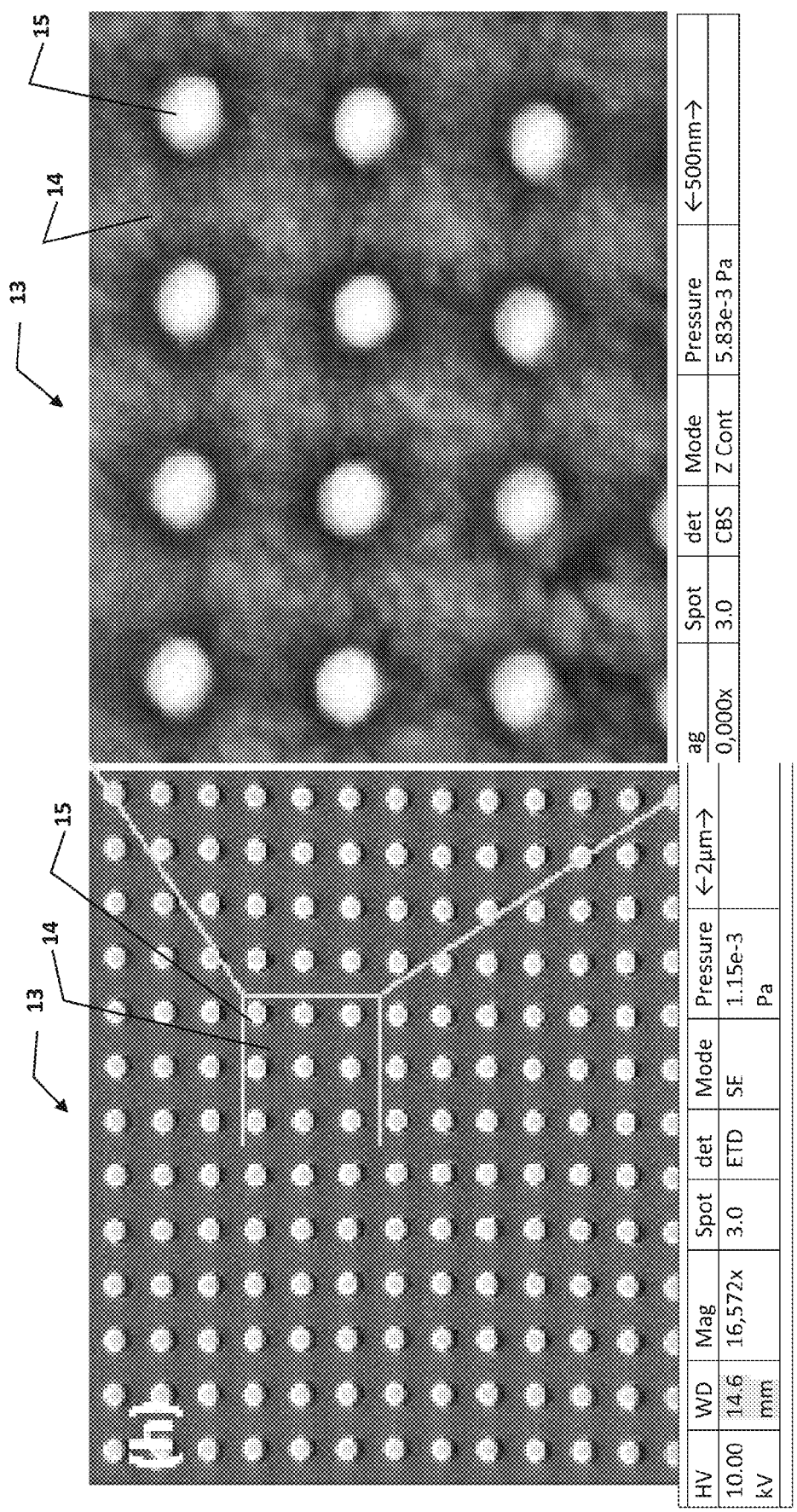

FIGS. 12A-C include: (At FIG. 12A) Step-wise representation for the fabrication of 3D ZPUA nanoposts array using soft lithography-based replica molding process. (At FIGS. 12B-C) SEM images of the Au-coated nanoposts on a glass substrate.

FIGS. 13A-D include: (At FIG. 13A) Transient responses of the sensor with and without Au nanoposts. (At FIGS. 13B-C) CA responses for the sensors with (FIG. 13B) and without (FIG. 13C) nanoposts as a function of ErbB2 concentration ($10^{-15}$ to $10^{-7}$ M) at a constant sensing potential of 0.01 V in presence of PBS containing 5 mM of $[Fe(CN)6]^{3-4-}$. (At FIG. 13D) Calibration plots for the immunosensors.

FIGS. 14A-D include: (At FIG. 14A) Refractive index sensitivity of the sensor. (At FIG. 14B) SPR response showing a redshift of 17.7 nm after coating GO on Au nanoposts. With anti-ErbB2 on GO-Au nanoposts, the resonance is redshifted to 716.6 nm. (At FIG. 14C) Transient response for detection of ErbB2. The inset shows the hill spectra dependence of ErbB2 concentration ($10^{-15}$ to $10^{-9}$ M). (At FIG. 14D) SPR resonance wavelengths as a function of ErbB2 concentration.

FIGS. 15A-D include: (At FIG. 15A) Transient response for selectivity test of the sensor in presence of nonspecific (ErbB receptor tyrosine kinase family) interferents such as ErbB3 (1.0 nM) and ErbB4 (1.0 nM). Concentration of ErbB2 was set to 1 fM during the selectivity test. (At FIG. 15B) Current versus interferents. (At FIG. 15C) Reproducibility test of the sensor conducted with four identical immunoelectrodes with 1.0 fM concentration of ErbB2. (At FIG. 15D) Stability test of this sensor performed for 4 weeks at an interval of seven days.

IV. DETAILED DESCRIPTION OF EXEMPLARY EMBODIMENTS OF THE INVENTION

A. Overview

For a better understanding of the invention, a generalized overview followed by specific non-limiting examples are presented below. It is to be understood that they are neither inclusive nor exclusive of all possible forms and embodiments. Variations obvious to those skilled in the art will be included within the invention.

B. Generalized Embodiment

At a general level, a sensing surface of nanoposts with noble metal/GO layers and biofunctionalized with anti-biomarker molecules allows simultaneous dual modality measurements based on electrochemical techniques and SPR techniques.

One aspect of the invention can be understood by reference to FIGS. 10A and B. As mentioned above, attempts have been made at dual modality electrochemical/SPR biosensing measurements according to the methodology of FIG. 10A.

In FIG. 10A the method (generally at ref. no. 100) prepares a planar surface coated or deposited with nanoparticles (e.g. nanotubes or nanowires) biofunctionalized to attach and bind in place molecules of a target biomarker (Step 102). An analyte is exposed to the coated biofunctionalized nanoparticles (Step 104). Electrochemical and SPR measurements are taken and analyzed (Steps 106 and 108).

In contrast, a method 200 according to the invention is illustrated in FIG. 10B. Instead of coating or otherwise applying a layer of nanoparticles to a planar substrate, an array of nanoscale structures (e.g. nanoposts) are fabricated with precision across a sensing area for a biosensor (for example, with soft lithography and appropriate process controls) (step 201). Upon this 3-D base or framework, noble metal/GO layers are added, along with biofunctionalization to attach and bind in place molecules of a target biomarker (step 202). Analyte is exposed to this biofunctionalized 3-D nanopost array arrangement (step 204), the dual modality measurements acquired (step 206), and those measurements become available for use (step 208). As discussed in the context of the Specific Examples below, the different paradigm of method 200 compared to method 100 goes in a counter-intuitive direction. It first forms a pre-determined 3-D structural array and then adds layers that follow that precise 3-D structural array form factor. This has been demonstrated to produce a number of beneficial results for both modes of measurement.

It has been found that the nanoposts present increased surface area to and beneficial radial diffusion of the sample volume, and other benefits including those described regarding the specific exemplary embodiments below.

C. Specific Embodiment 1

The following is a more specific statement of one form the invention can take, including proof of concept.

From Md. Azahar Ali, Shawana Tabassum, Qiugu Wang, Yifei Wang, Ratnesh Kumar, and Liang Dong, Integrated Dual-Modality Microfluidic Sensor for Biomarker Detection Using Lithographic Plasmonic Crystal, Lab Chip, 2018, 18, 803-817, including Supplemental information from www.rsc.org/suppdate/c7/1c/c71c01211j/c71c01211j/c71c001211j1.pdf (both incorporated by reference in their entireties).

Overview

This reports an integrated dual-modality microfluidic sensor chip, consisting of a patterned periodic array of nanoposts coated with gold (Au) and graphene oxide (GO), to detect target biomarker molecules in a limited sample volume. The device generates both electrochemical and surface plasmon resonance (SPR) signals from a single sensing area of Au-GO nanoposts. The Au-GO nanoposts are functionalized with specific receptor molecules, serving as a spatially well-defined nanostructured working electrode for electrochemical sensing, as well as a nanostructured plasmonic crystal for SPR-based sensing via the excitation of surface plasmon polaritons. High sensitivity of the electrochemical measurement originates from the presence of the nanoposts on the surface of the working electrode where radial diffusion of redox species occurs. Complementarily, the SPR detection allows convenient tracking of dynamic antigen-antibody interactions, to describe the association and dissociation phases occurring at the sensor surface. The soft-lithographically formed nanoposts provide high reproducibility of the sensor response to epidermal growth factor receptor (ErbB2) molecules even at a femtomolar level. Sensitivities of the electrochemical measurements to ErbB2 are found to be 20.47 $\mu A/\mu M/cm^2$ in a range from 1 fM to 0.1 µM, and those of the SPR measurements to be 1.35 nm/µM in a range from 10 pM to 1 nM, and 0.80 nm/µM in a range from 1 nM to 0.1 µM. The integrated dual-modality sensor offers higher sensitivity (through higher surface area and diffusions from nanoposts for electrochemical measurements), as well as the dynamic measurements of antigen-antibody bindings (through the SPR measurement), while operating simultaneously in a same sensing area using a same sample volume.

1. Introduction

Conventional tools for diagnosis of cancerous tissues include X-ray mammography, magnetic resonance imaging (MRI), enzyme-linked immunosorbent assay (ELISA), and immunohistochemistry.[1-4] However, ~80% of most breast cancers may not be detected by the mammographic screening method due to highly dense and proliferative cells.[2] The MRI method is relatively expensive, and cancerous features may not be detected until they are large enough to be imaged. The ELISA and immunohistochemistiy methods require large volumes of samples and tagging molecules.[3-4] In this context, high-performance miniaturized sensors with minute sample consumptions are highly desirable. Recently, many reported microfluidic sensors have demonstrated their ability to detect cancer biomarkers with high sensitivity.[5-6] An example of a cancer biomarker is the epidermal growth factor receptor (ErbB), a cell-surface receptor in humans that regulates cell proliferation, migration, apoptosis, and motility via different signaling pathways.[7-8] Excessive signaling of ErbB is associated with the malignancy of tumors and neurodegenerative diseases. Among ErbB genes, the amplification (~30%) of ErbB2 gene, which encodes a transmembrane glycoprotein, is responsible for breast cancer metastasis.[9] Breast cancers can have up to 25-50 copies of the ErbB2 gene and up to 40-100-fold increase in ErbB2 protein, leading to 2 million receptors expressed at the tumor cell surface.[10]

Most of the cancer biomarker-based sensors provide a single modality of electrical, mechanical, electrochemical, or optical signal. With the continuing trend of minimizing sample consumptions, there is an issue with reliability and accuracy of the miniaturized sensors for biomarker detection associated with using limited sample volumes. Therefore, several efforts have been made to tackle this problem, including creating nanofluidic structures to handle reduced volumes of sample, agent and reagent,[11] developing new receptor molecules with improved detection specificity,[12] enhancing surface areas of sensing materials,[13] and tracking spectral shifts of multiple resonance peaks of optical sensors.[14]

Generation and monitoring of different sensing modalities from a single sensor has also been demonstrated to improve detection reliability and reduce false reads of the sensor.[15,16] In this work, we report a dual-modality sensor that integrates the electrochemical and surface plasmon resonance (SPR) modalities in a novel way, on the same sensing surface, offering the opportunity to work with same sample volume for both the modalities.

Notably, electrochemical sensors allow high-sensitivity detection of cancer biomarkers,[17] and many micro/nanostructured conducting materials are incorporated into electrochemical sensors for improving the surface area to volume ratio, electron transport rate, and electrochemical reactivity of the working electrodes.[18] These improved electrodes enable more efficient radial or spherical diffusions of redox species from surrounding bulk solutions to electrode surfaces, compared to the linear diffusion occurring at a planar or macroscale electrode.[19-21] Consequently, nanomaterials with different shapes (e.g., disk, cylindrical, band, ring, etc.)[19-21] have been developed using various methods, such as nanoparticles by in situ chemical synthesis,[22] nanowires by hydrothermal synthesis,[23] nanotubes by chemical vapor deposition,[24] and patterned nanofibers by electrospinning.[25,26]

Similarly, plasmonic biosensors have also been extensively reported to detect cancer biomarkers,[27] and study bimolecular interactions of receptor-ligand,[28] avidin-biotin,[29] protein-DNA,[30] and protein-protein.[31] Essentially, this type of optical sensor detects subtle changes in refractive index caused by the immobilization and binding of biomolecules at the surface of noble metal-based nanostructures. It should be noted that, although many metallic nanostructures have been applied to plasmonic biosensors, they are often realized using non-lithographical approaches with a relatively low spatial uniformity in size, shape and distribution. This has influenced the performance reproducibility of these sensors.[32,33] To obtain high uniformity, advanced nanofabrication techniques, such as electron-beam lithography,[34] focused ion beam lithography,[35] nanoimprinting,[36] multiphoton lithography,[37] and hole mask lithography,[38] have been adopted to realize well-defined nanostructures (e.g., nanogratings,[39] nanoholes,[40] nanocones[41], and nanoposts[36,42]) for plasmonic biosensors.

Here we report our integrated dual-modality microfluidic sensor combining the two aforementioned sensing modalities, namely, electrochemical and plasmonic measurements, on a single nanostructured substrate to detect cancer biomarker in a small sample volume (FIGS. 1a and b). The periodically arranged nanoposts coated with a gold-graphene oxide (Au-GO) layer serve as the working electrode of an electrochemical sensor, as well as the nanopatterned substrate of a plasmonic sensor. Because the nanoposts are manufactured using a soft lithography based nanomolding process, they are inexpensive and have high structural uniformity and thus provide improved performance reproducibility of the sensors. Further, due to the presence of the nanoposts on the working electrode that provides a larger surface area, the electrochemical signal produced from the sensor is greater than its counterpart using a planar electrode.

While electrochemical sensors offer high sensitivity, they are generally limited in the dynamic tracking of binding kinetics (e.g., equilibrium association and dissociation phases) of biomolecular interactions at the sensor surface[43,44] This limitation is overcome by our plasmonic sensing performed on the same nanopost area that excels in tracking dynamic antigen-antibody interactions. Such an ability allows quantifying of protein-protein binding affinity for studying binding kinetics, which, in general, is crucial to help understand molecular recognition of the biological system, and thus help design and implement a better target antibody for antigen.[45] Therefore, the combination of the electrochemical and plasmonic sensing modalities together in the same area on a single nanostructured substrate offer both sensitivity and quantitative information of biomolecular interactions, in addition to other advantages such as small footprint area, low sample consumption, and improved detection reliability.

This example builds on our earlier work of Ref. 46, which is included infra as Specific Example 2. Compared to ref 46, the contributions of this work include follows:

a. Additional details of a fabrication process for the integrated dual-modality sensor.

b. Electrochemical simulation to illustrate the importance of using Au-coated nanoposts, chronoamperometry (CA) and cyclic voltammetry (CV) studies of the sensor, and demonstration of detection for the breast cancer biomarker ErbB2.

c. additional characterization of sensitivity, selectivity, reproducibility, and stability for electrochemical measurement d. Simulation and analysis of SPR mode of the sensor, and estimation of sensitivity to changes in surrounding refractive index.

e. SPR measurement for ErbB2 with sensitivity, reproducibility, and stability, and demonstration of using the SPR mode to monitor binding kinetics at the sensor surface continuously.

f. Additional demonstration of simultaneously using both the electrochemical and SPR measurement methods on a single dual-modality sensor to detect ErbB2.

g. Performance comparisons of the sensor with existing sensors reported in the literature for the detection of ErbB2.

2. Sensor Structure and Fabrication

As shown in FIG. 1, a sensor system 10 includes a lab-on-a-chip scale sensor element (generally at ref. no. 12). Chip 12 includes a sensing area 13 of biofonctionalized 3D nanostructures. As will be discussed with specific examples below, the 3D nanostructures here are is a base layer 14 with an array of soft lithography fabricated nanoposts 15 extending from one side. Those nanoposts are coated with a noble metal (here Au 16) and graphene oxide (GO) 17. Therefore, in this description the final nanoposts will be referred to as nanoposts 15/16/17 to indicate the combination of the 3D structures and the coatings of Au and GO. As such, nanoposts 15/16/17 present electrically conductive properties from Au and GO that can be presented to the analyte samples for purposes of electrochemical systems based on changes in conductivity, but also for surface plasmon resonant optical measurements.

As will be appreciated, an appropriate receptor molecule can be chosen and also added to nanoposts 15/16/17 relative to the biomarker molecule of interest in the analyte. In this example, the receptor molecules 18 are the anti-ErbB2 molecules for the ErbB2 protein as the target molecules 19.

Analyte samples comprising a viscous fluid are controllable provided to sensing area 13 by a microfluidic subsystem 20. Sensing area 13 with nanoposts 15/1/17 is positioned in a chamber 24 along microfluidic input and output channels and ports 21/22/23 and 25/26/27 respectively. By well-known microfluidic techniques (e.g. pumping, valving, exhausting to waste), a flowable analyte can be metered into chamber 25 for the dual mode measurements.

Electrochemical measurements can be obtained by electrochemical subsystem 30. It includes the working, counter, and reference electrodes 32,34, and 36, each operably connected to supply electrical current and measure changes in conductivity when a sample analyte is at nanoposts 15/16/17 in sensing area 13. Such electrochemical electrode-based sensing is well-known in the art.

SPR measurements can be obtained by an appropriate SPR subsystem 40. It can include an excitation source (here white light source 42) which is configured to direct focused light energy 43 onto the sample at nanoposts 15/16/17, as well as a spectrometer 44 configured to collect reflectance 45 as a result of the excitation of light source 42 and detect SPR-related spectral changes. This technique is well-known in the art.

A controller/processor 50 (one or more) can be operably connected to subsystems 20,30, and 40 to at least semi-automatically control by programming such things as metering of analyte to sensing area 13, direction of light to the sample, and collection and processing of both electrical and optical measurements. As will be appreciated by those skilled in the art, controller/processor can take the form of digital processors, digital computers, and networks of the same, including digital storage and communication both by LAN or WAN.

2.1. Structure. The periodically arranged Au-GO nanoposts 15/16/17 serve as the working electrode for the electrochemical sensor, and also enable SPR modulation[42,47] during kinetic binding with the target molecules. To complete the electrochemical sensor (generally ref. no. 10 in FIG. 1), Au counter electrode 32 and silver/silver chloride (Ag/AgCl) reference electrode 36 are placed on two sides of the nanoposts area (generally at ref. no. 13) (see also FIG. 2F). The electrochemical measurement monitors the amperometric current flow from the nanoposts 15/16/17 to the counter electrode 32 under an excitation potential applied between the working 34 and reference electrodes 36. In the SPR-based measurement mode, coupling of normal incident light 43 into the nanoposts 15/16/17 provides a reflection dip owing to the excitation of (1,0) surface plasmon polaritons (SPPs) at the interface between the nanoposts 15/16/17 and surrounding environment.[47] This integrated dual-modality sensor 10 relies on specific immuno-interactions between target breast cancer biomarker (ErbB2) 19 and anti-ErbB2 molecules 18 on the surface of nanoposts 15/16/17. When the nanoposts capture ErbB2 protein 19, the surface density of ErbB2 antigen 18 is altered. As the concentration of ErbB2 protein 19 varies, both the SPR wavelength and electrochemical current from the same sensing area 13 will change, thus providing two different signatures of the specific antigen-antibody reactions.

In a typical design, the pitch, diameter, and depth of the polymer nanoposts IS are 500 nm, 250 nm, and 210 nm, respectively. The nanoposts 15 are sequentially coated with an 80 nm-thick Au film 16 and a 20 nm-thick GO layer 17, resulting in an optical resonance at the wavelength near 699 nm when immersed in water (described later). The diameter of the round-shaped sensing area 13 of working electrode 34 is 3.4 mm, allowing easy alignment of the normal incident light to the sensing area 13. The strip-shaped Au counter 32 and Ag/AgCl reference 36 electrodes are 1.5 mm wide. The channels 23 and 24 connecting to the sensing area 13 chamber 24 are 400 µm deep and 1.5 mm wide, allowing delivery of liquid samples to the sensing area.

2.2. Fabrication. Fabrication of the integrated dual-modality sensor 12 involved creation of an array of polymeric nanoposts, formation of Au working and counter electrodes, formation of Ag/AgCl electrode, functionalization of GO nanosheets, covalent immobilization of anti-ErbB2, and formation of microfluidic channels (FIGS. 2A-E).

Specifically, to form a periodic array of Au nanoposts, a silicon nanostamp was first manufactured using standard e-beam lithography and subsequent reactive ion etching, and then was salinized for 20 min using (tridecafluoro-1,1,2,2-tetrahydrooctyl)-1-trichlorosilane. Subsequently, a hard-PDMS (h-PDMS) precursor solution was prepared by mixing poly (7-8% vinylmethyl-siloxane)-(dimethylsiloxane), (1,3,5,7-tetravinyl-1,3,5,7-tetramethylcyclotetrasiloxane), platinum catalyst xylene and poly (25-30% methylhydrosiloxane)-(dimethylsiloxane) at the weight ratio of 3.4:0.1:0.05:1. Air bubbles were then removed from the mixture by degassing for 10 min. Next, the h-PDMS solution was spin-coated on the surface of the nanostamp at 1000 rpm for 40 s, and cured at 70° C. for 10 min. Following that, a soft-PDMS (s-PDMS) pre-polymer solution was prepared by mixing Sylgard 184 monomer and its curing agent (Dow Corning, Midland, Mich., USA) at the weight ratio of 10:1. After degassed for 30 min, the s-PDMS solution was poured onto the surface of the h-PDMS and cured on a hotplate at 65° C. for 2 hrs. (FIG. 2A). Then, a PDMS mold, including both the s-PDMS and h-PDMS layers, was peeled off from the silicon mold. The obtained PDMS mold contains the nanoholes. It should be noted the s-PDMS pre-polymer solution was not directly poured over the silicon mold to form an s-PDMS mold since the s-PDMS pre-polymer solution has a high viscosity that makes it difficult to fully enter the nanowells of the silicon mold. Although increasing the weight ratio of the monomer to its curing agent can decrease viscosity, the cured s-PDMS are difficult to detach from the silicon mold without breaking. Compared to the s-PDMS precursor solution, the h-PDMS precursor solution has a lower viscosity and thus can conform to the nanostructured surface of the silicon mold. The formation of the additional s-PDMS layer on top of the cured h-PDMS helps when peeling the PDMS structure from the silicon mold. After the PDMS mold was formed, a drop of ultra-violet (UV) curable ZPUA precursor solution (Gelest, Inc., Morrisville, Pa., USA) was dropped on the surface of the PDMS mold, and then the mold was placed on top of a glass slide. To cure ZPUA, the glass slide was exposed to an ultraviolet light (intensity: 3.3 mW/cm$^2$) for 5 min (FIG. 2B). After the exposure, a periodic array of ZPUA nanoposts was formed.

Next, a 5-nm-thick Ti layer and an 80-nm-thick Au layer were sequentially deposited onto the glass slide containing the ZPUA nanoposts array by e-beam evaporation (FIG. 2C). The samples were mounted on a tilting and rotating substrate holder to improve the sidewall Au coverage of nanoposts. The scanning electron microscopic (SEM) image (inset of FIG. 2C) shows that the sidewalls of nanoposts were covered by Au. The round-shaped working and strip-shaped counter electrodes were patterned using a shadow mask. Similarly, a 1 μm-thick Ag electrode was then fabricated on the same glass slide by e-beam evaporation. To form an Ag/AgCl electrode, a solution of KCl (0.1 M) was used to treat the surface of Ag electrode (FIG. 2D).

Further, the Au nanopost array was drop-coated with a 20 nm-thick layer of GO nanosheets to enable covalent conjugation of anti-ErbB2 (FIGS. 2D, G, and H). In this step, a well dispersed colloidal solution of single-layer GO nanosheets (0.1 mg mL$^{-1}$) was prepared in DI water via thorough sonication. The Au nanopost surface was next treated by oxygen plasma. As a result, the hydrophobic nature of the Au surface became hydrophilic. 20 μL of the prepared GO suspension solution was drop cast onto the treated Au nanopost surface and dried in air at room temperature for 2 h (FIG. 2H, inset). The GO layer conformed to the shape of the nanoposts beneath it Due to the presence of abundant functional groups (e.g., —CHO, —COOH, etc.) at GO nanosheets, the GO layer served as an immobilization surface for covalent binding of mf-ErbB2 molecules.

To integrate the three-electrode sensor into a microfluidic channel of photopatternable polymer[48], in-situ liquid phase polymerization (LP$^3$) process[49] was performed (FIGS. 2A-E, and FIGS. 8A-E, Supporting Information). In this step, 400 μm-thick adhesive spacers were positioned between a 1 mm-thick glass slide and the device substrate containing all the electrodes, to form an air cavity. The glass slide contained two 1 mm-diameter through-holes (i.e., the inlet and outlet of a channel) pre-drilled using a conventional milling machine with an attached 1 mm-diameter diamond drill bit. Subsequently, a photopatternable polymer solution consisting of isobornyl acrylate, crosslinker-tetraethylene glycol dimethacrylate, and photoinitiator-2,2-dimethoxy-2-phenylacetophenone at a weight ratio of 31.66:1.66:1.0 was injected into the air cavity using a plastic pipette (FIGS. 8A-E, Supporting Information). A photomask printed on a transparent film (6400 dpi; Fineline Imaging; Colorado Springs, CO, USA) was positioned on top of the glass slide. Next, an ultraviolet light of 12 mW cm$^{-2}$ intensity was used to expose the device for 60 s. To remove the unpolymerized polymer solution, the channel was washed with ethanol for 4 min. Therefore, the channel was formed and integrated with the sensor (FIGS. 8A-E, Supporting Information). For comparison, a control device was also manufactured and tested, which had a planar Au electrode with the same diameter as the sensor except for having no nanoposts.

23. Surface biofunctionalization. The periodic GO-Au nanoposts were functionalized with anti-ErbB2 molecules via EDC-NHS coupling chemistry.[50] For immobilization, a solution of anti-ErbB2 (1 mg/mL) and EDC-NHS (EDC 0.2 M; NHS: 0.05 M) was prepared at a 1:1 volume ratio. A 200 μL of this solution was injected into the channel to cover the surface of the GO-Au nanoposts. The sensor was then kept inside a humid chamber for 12 h at 4° C. The EDC reacted covalently with —COOH groups present at the GO nanosheets to form an intermediate O-acylisourea, while the NHS produced an intermediate amine-reactive stable NHS ester to allow the conjugation with primary amines of mM-ErbB2 via the formation of covalent C—N bonds. A bovine serum albumin (BSA; 2 mg/mL) solution was injected into the channel, followed by washing the sensor surface with the phosphate-buffered saline (PBS) solution (pH=7.4) to block the non-specific sites of the sensor.[51]

3. Experimental Setup and Simulation 3.1. Chemicals. Lyophilized powder of ErbB2 antigen (human CellExp™, fused with polyhistidine tag at the C-terminus; source: HEK293 cells and molecular weight: 72.4 kDa), ErbB3 antigen (molecular weight: 71.5 kDa), and ErbB4 antigen (molecular weight: 70.6 kDa, fused with 6×histidine tag at the C-terminus) were procured from BioVision, Milpitas, Calif., USA. Stock solutions of ErbB2, ErbB3, and ErbB4 antigens were prepared using PBS (pH=7.4) and diluted serially to form 0.1 μM to 1.0 fM solutions. A specific polyclonal antibody of ErbB2 was obtained from BioVision, Milpitas, Calif., USA, and prepared with PBS (pH=7.4) solution containing 1% bovine serum albumin (BSA), 30% glycerol, and 0.02% thimerosal. N-ethyl-NO-(3-dimethylaminopropyl carbodiimide) (EDC) and N-hydroxysuccinimide (NHS) were procured from Sigma Aldrich, Mo., USA. Single layer GO nanosheets were purchased from ACS Material, Pasadena, Calif., USA, wherein the elemental compositions in GO are 40.78% and 51.26% for O (wt %) and C (wt %), respectively, and the atomic ratio of C to O is 1.67. Deionized (DI) water with the resistivity of 18.2 MΩ cm was produced using a purification system from Millipore, Billerica, Mass., USA, and utilized for all experiments.

3.2. Instruments. For electrochemical measurements, a constant potential (−0.01 V) was applied to the nanoposts-based working electrode with respect to the reference electrode. The sensor was subject to various concentrations of ErbB2 solution in the PBS (pH=7.4) solution mixed with an equimolar (5.0 mM) concentration of ferro/ferricyanide ([Fe(CN)$_6$]$^{3-/4-}$). All electrochemical measurements were performed using an electrochemical workstation (DY2100; Digi-Ivy, Austin, Tex., US). The ferro/ferricyanide redox probe was chosen to investigate the redox activity such as radial or planar diffusion on the working electrode.

For optical measurements, a bifurcated optical fiber (BIF 400-VIS-NIR, Ocean Optics) was connected to a white light source (150 watt quartz halogen lamp; Luxtec Fiber Optics, Plainsboro NJ). A normal incident light from the source was used to illuminate the nanoposts area inside the channel through a collimator (F220SMA-A; Thorlabs, Newton, N.J.). The reflected light from the sensor was collected and measured by a UV/VIS spectrometer (USB-4000, Ocean Optics) on the other end of the bifurcated fiber.

4. Results and Discussion 4.1. Electrochemical characterization. The integrated dual-modality sensor was characterized both electrochemically and optically. First, CA technique was employed to investigate electrochemical redox reactivity of the sensor. The electrochemical measurement was conducted in the PBS solution (pH=7.4) containing a 5 mM equimolar concentration of ferro and ferricyanide ([Fe(CN)$_6$]$^{3-/4-}$) redox mediator. FIG. 3A shows that the sensor with the Au nanoposts exhibits a 5.4-fold enhancement in output current (~106.4 μA) and a 3-fold reduction in response time (~5 s), compared to those (~19.7 μA and ~15 s) of the control device with the planar Au electrode.

To assess the benefit from using the nanoposts on the sensor surface, the finite-element method (FEM) based software COMSOL Multiphysics was used to study the diffusion of redox species to the nanoposts-based and planar electrodes under an applied potential. An electroanalysis model was used,[52] where the geometric parameters were obtained from the SEM images of the fabricated device (FIG. 2H). The simulated concentration profile of the generated redox species near the 3D electrode indicates that the nanoposts enable more efficient and faster diffusion of the redox species to the electrode surface, compared to the planar electrode (FIG. 3D). Therefore, the current enhancement observed in FIG. 3A is attributed to the nanoposts that serve as vertically arranged 3D nanoelectrodes to allow the radial diffusion (FIG. 3E).[19-21] In contrast, the reaction at the planar electrode is controlled by linear diffusion, yielding a low redox current (FIG. 3F).

Next, the sensor was characterized using cyclic voltammetry (CV) technique in the same PBS solution (pH=7.4) with the same redox mediator. FIG. 3B shows well-defined CV curves wherein the nanoposts-based sensor exhibits a higher redox current than that with the planar electrode. The peak-to-peak potential difference (ΔE) is calculated as 0.099 V for the nanoposts-based electrode, whereas ΔE is found as 0.452 V for the planar electrode, indicating faster electron transfer for the nanoposts.

With the immobilization of anti-ErbB2, the redox current of the Au nanoposts decreases due to the inherent insulating property of the antibody that slows down the electron transfer. As the scan rate increases from 10 to 100 mV/s, the anodic and cathodic currents increase towards positive and negative potentials, respectively, hence, a surface-controlled diffusion process occurs on the sensor surface (FIGS. 3C and 9, Supporting Information). According to Rendles-Sevcick equation,[53] the diffusion coefficient is given as:

$$D^{1/2} = \frac{i_p}{268,600 \times n^{3/2} A C v^{1/2}} \quad (1)$$

where $v^{1/2}$ is the root mean square of scan rate, and A is the area of electrode. Table 1 shows the electrochemical parameters obtained for various fabricated electrodes, including the planar electrode, and the nanoposts-based electrode with and without antibody molecules. It is found that the Au nanoposts-based electrode provides an enhanced diffusion coefficient of $D=3.65\times10^{-9}$ cm$^2$/s, due to the radial diffusion of redox species, while the planar counterpart electrode provides a lower value of $D=0.51\times10^{-9}$ cm$^2$/s. The heterogeneous electron transfer rate constant ($k_s$) is obtained based on Laviron's theory[52]. The Au nanoposts-based electrode provides $k_s$=0.79 cm/s, which is about 3.3 times of magnitude greater than the planar electrode ($k_s$=0.24 cm/s).

TABLE 1

Electrochemical parameters for various working electrodes.

| Electrodes | Peak current (μA) | Peak-to-peak potential difference (V) | Diffusion coefficient (cm$^2$/s) | Heterogeneous electron transfer rate constant (ks; cm/s) |
|---|---|---|---|---|
| Planar Au-GO electrode | 24.6 | 0.452 | 0.51 × 10$^{-9}$ | 0.24 |
| Nanoposts-based Au-GO electrode | 65.2 | 0.099 | 3.65 × 10$^{-9}$ | 0.79 |
| Nanoposts-based Au-GO electrode with anti-ErbB2 | 32.5 | 0.104 | 0.88 × 10$^{-9}$ | 0.51 |

Figure 4D:
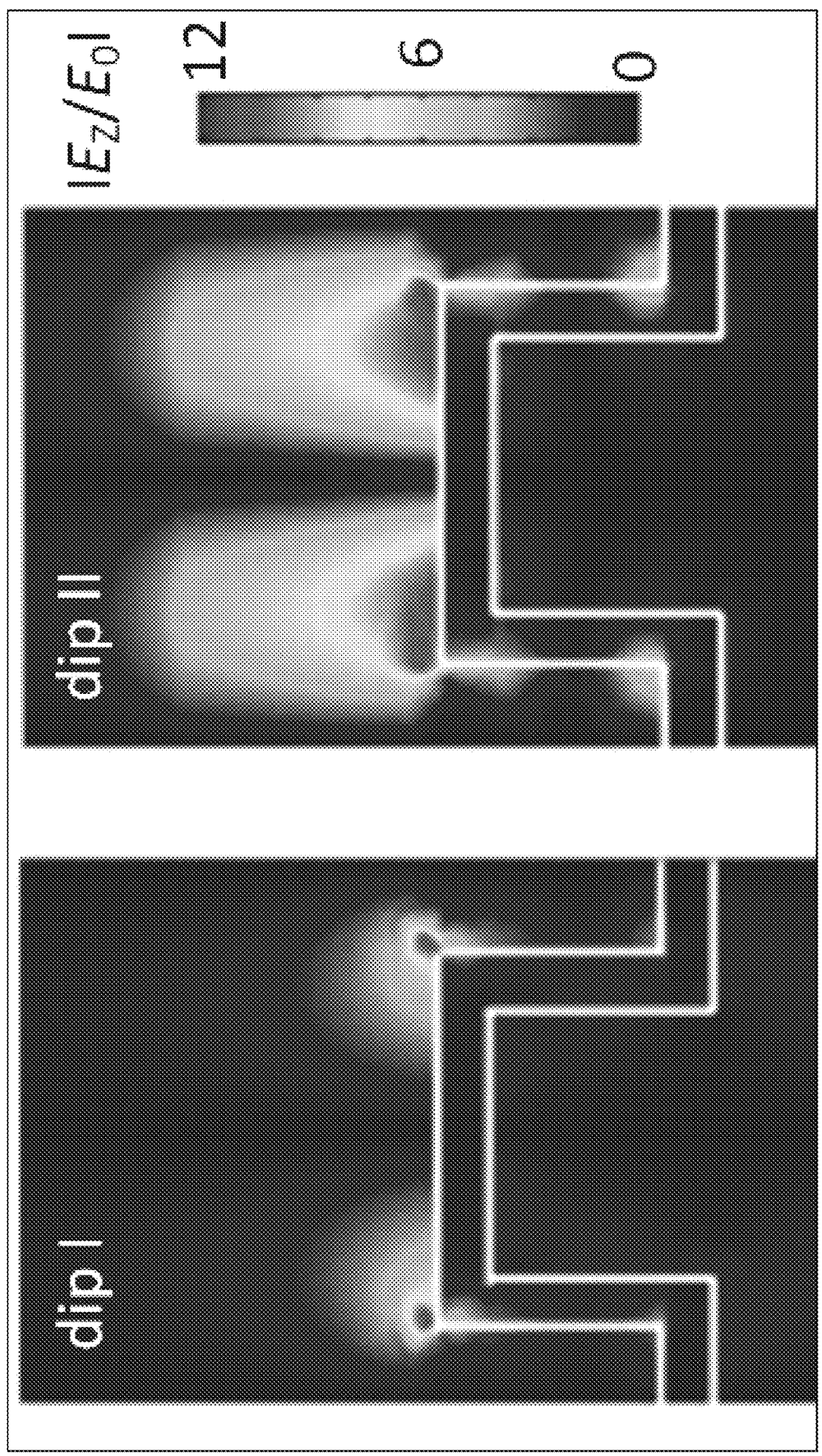

4.2. SPR characterization. Under a normal incident light, SPR is generated at the interface between the Au nanoposts and surrounding environment. For a two-dimensional structure with square lattice,[47] the free-space wavelength of incident light to excite SPPs is given as:

$$\lambda = \frac{\Lambda}{\sqrt{i^2+j^2}} \sqrt{\frac{\varepsilon_{Au}\varepsilon_d}{\varepsilon_{Au}+\varepsilon_d}} \quad (2)$$

where $\varepsilon_d$ and $\varepsilon_{Au}$ are the dielectric constants of the surrounding medium and Au, respectively, $\Lambda$ is the lattice constant, and (i,j) corresponds to the order of SPPs. The bulk index sensitivity of this Au nanoposts array was measured to be 449.6 nm per refractive index unit (nm/RIU) by introducing water (refractive index: 1.33), acetone (1.363), ethanol (1.365), isopropyl alcohol (1.377), and chloroform (1.44) onto the sensor surface (FIG. 4A). FIG. 4B compares the changes in reflectance spectra for the Au nanoposts with and without GO coating, and after anti-ErbB2 immobilized on the GO-Au surface. Before the GO coating, the spectrum exhibits a reflection dip associated with (1, 0) SPP at 549 nm in air, as confirmed from the simulated spectrum (denoted as dip I in FIG. 4C) and electric field distributions (dip I in FIG. 4D), where the standing wave feature above the Au nanoposts indicates the excitation of SPPs. A redshift of 17.7 nm in air was observed with the GO coating on the Au nanoposts due to the increase in local refractive index (FIG. 4B). When the Au/GO nanoposts are exposed to the PBS solution with anti-ErbB2 molecules, a narrow resonance dip appears at 699 nm. To better understand the resonance mode used in the SPR measurement, we conducted the FEM simulation using the COMSOL multiphysics software. In this simulation, periodic boundary conditions were applied at the boundaries in parallel with the light propagation direction. The top and bottom of the computation regions were placed with two perfectly matched layers (PMLs) so that all the scattered electromagnetic waves from the nanopost arrays were absorbed at the PMLs.[47] In addition, the refractive index of the PMLs was set to the same value of neighbouring media to simulate an infinitely thick substrate.[47] The simulated spectrum for the Au nanoposts without GO in water presents a new resonance dip (denoted as dip II in FIG. 4C) near 700 nm wherein the electric field distribution confirms the excitation of SPPs at the interface between water and the Au nanoposts (FIG. 4D).

Figure 5C:
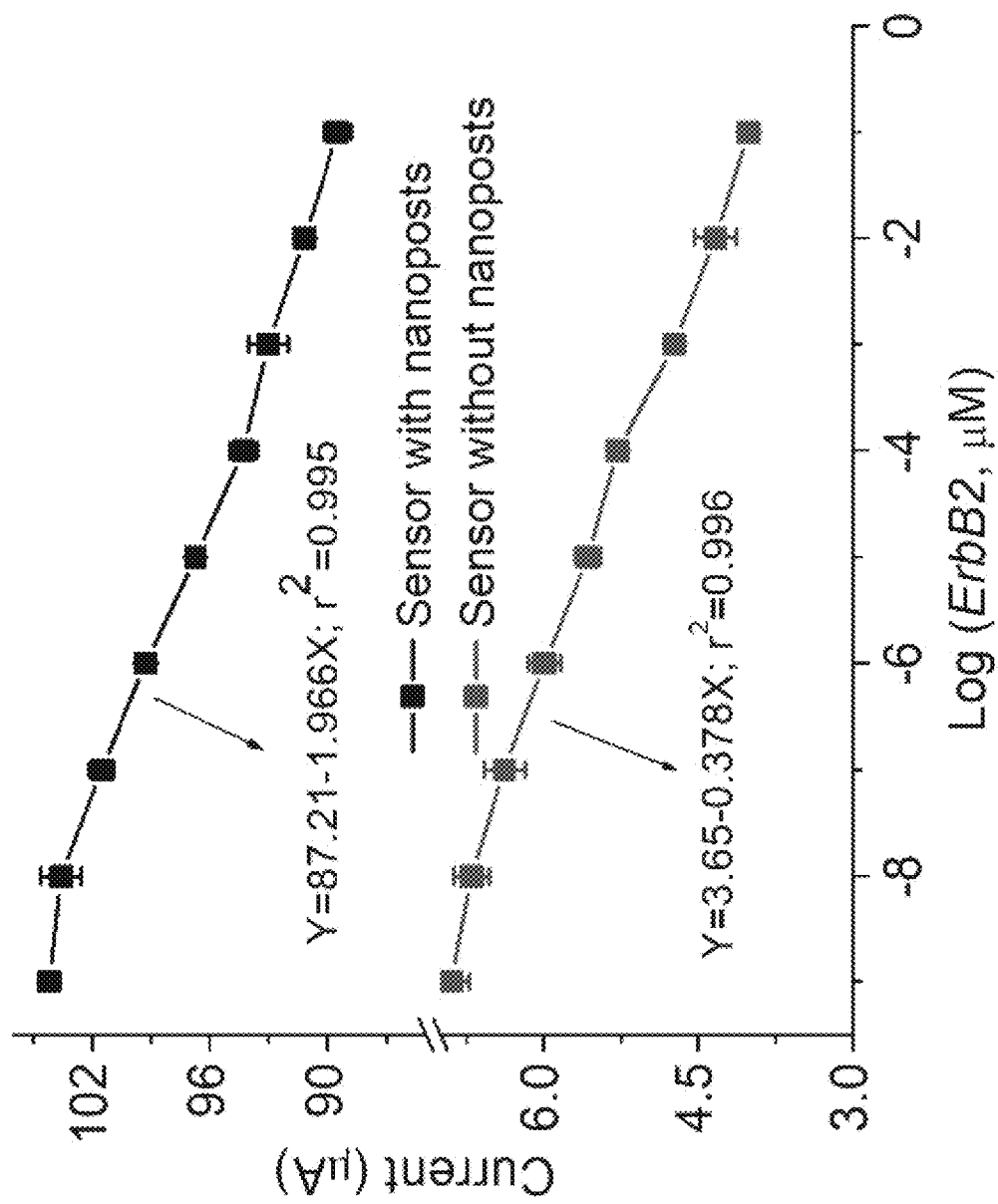

4.3. Electrochemical detection of biomarker. The sensor was exploited to detect specific concentrations of biomarker (ErbB2 antigen) using the CA measurement method. The GO-Au nanoposts functionalized with anti-ErbB2 were exposed to different concentrations of ErbB2 antigen ranging from 1.0 fM to 0.1 μM by injecting corresponding analyte solutions into the microfluidic channel. Figure 5a and b show the CA responses to different ErbB2 concentrations for a sensing potential of 0.01 V with and without the nanoposts, respectively. The CA responses are found to saturate at a constant current within 5 s (FIG. 5A). The transient responses (FIG. 5A) show a larger steady-state current owing to the radial diffusion occurring at the surface of nanoposts compared to the current at the planar electrode surface (FIG. 5B). In both the cases, the current decreases with increasing ErbB2 concentrations. This is due to the insulating layer of immunocomplex formation via binding of specific sites such as epitope at anti-ErbB2 and paratopes at ErbB2 antigen which can obstruct the acceleration of the electrons generated from redox reaction. As the number of ErbB2 antigen molecules bound to the sensor surface increases, the thickness of the resulting immunocomplex layer increases, leading to reduction in output currents. The calibration plots in FIG. 5C show that the sensor current is inversely proportional to the logarithmic concentration of ErbB2 antigen. Approximately, a five-fold enhancement was obtained for the sensitivity (20.47 µA/µM/cm$^2$) of the nanoposts-based sensor compared to that of the control sensor without using any nanoposts (3.94 µA/µM/cm$^2$), owing to the larger surface area and the radial diffusion of redox species. The larger surface area of the nanoposts enhances the loading capacity of GO nanosheets as well as antibody molecules, leading to an increased higher affinity towards ErbB2.

Figure 5D:
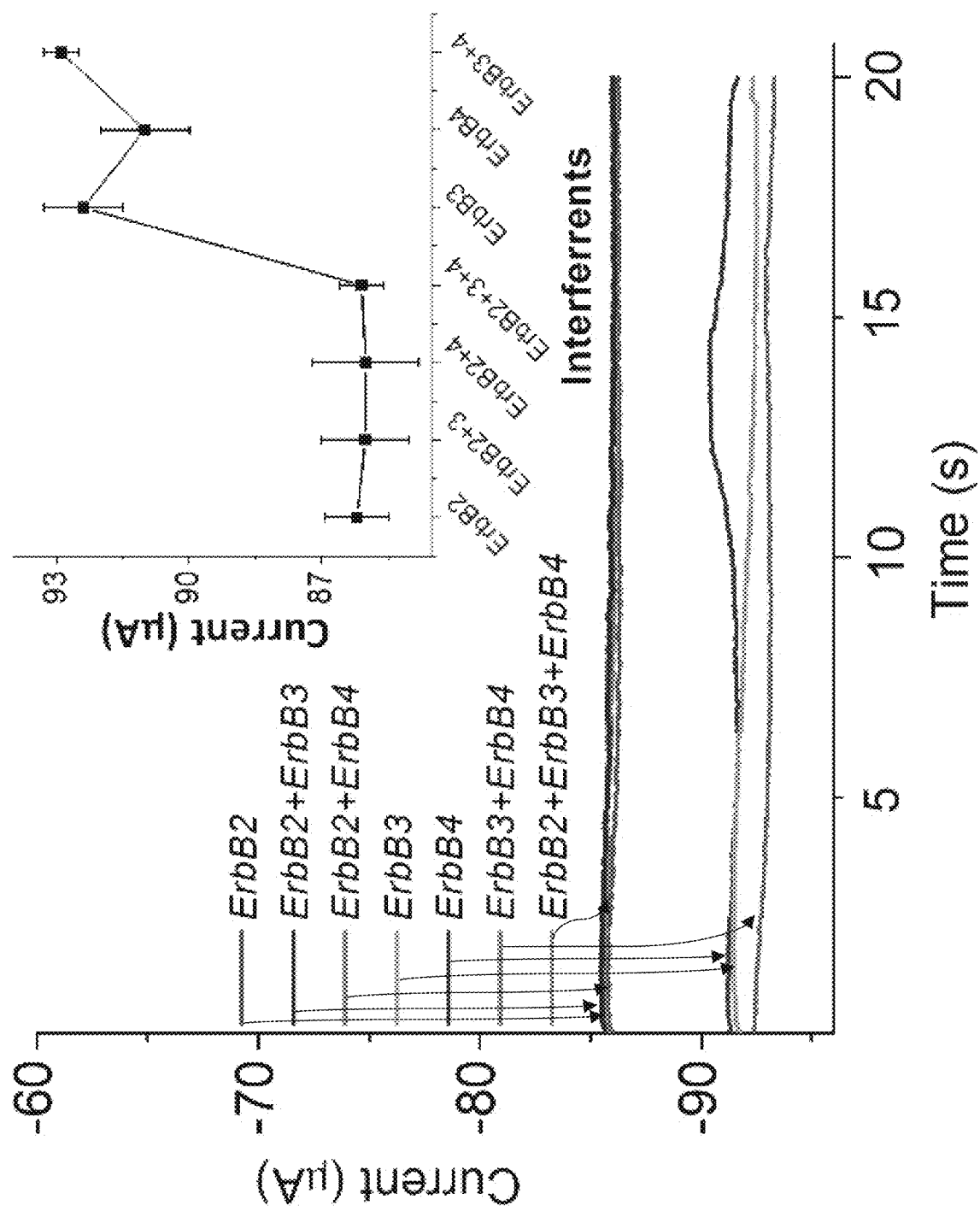

For the selectivity measurements, the sensor with the nanoposts was exposed to the non-specific interfering antigen species ErbB3 and ErbB4 in the ErbB receptor tyrosine kinase family. Similarly, the CA method was employed to measure the response of the sensor (FIG. 5D). When ErbB2 antigen (0.1 µM) was added to nonspecific ErbB3 (0.1 µM) alone, ErbB4 (0.1 µM) alone, and a mixture of ErbB3 (0.1 µM) and ErbB4 (0.1 µM), the sensor response did not change significantly as is evident from its low relative standard deviation (RSD; ±1.1%) from the initial response with ErbB2 (0.1 µM) only, indicating a good selectivity due to incorporating anti-ErbB2 on the sensor surface.

Figure 5E:
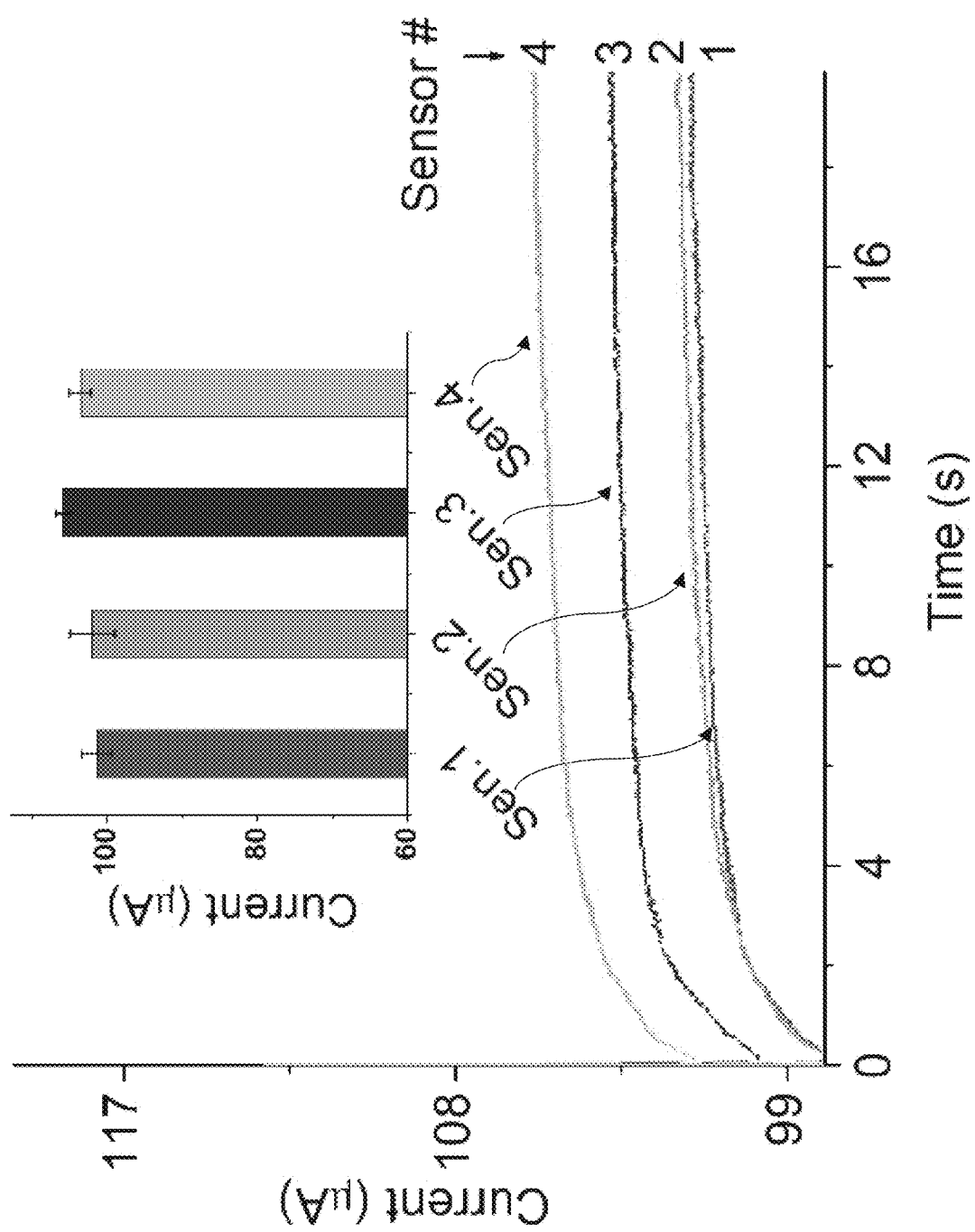
Figure 5F:
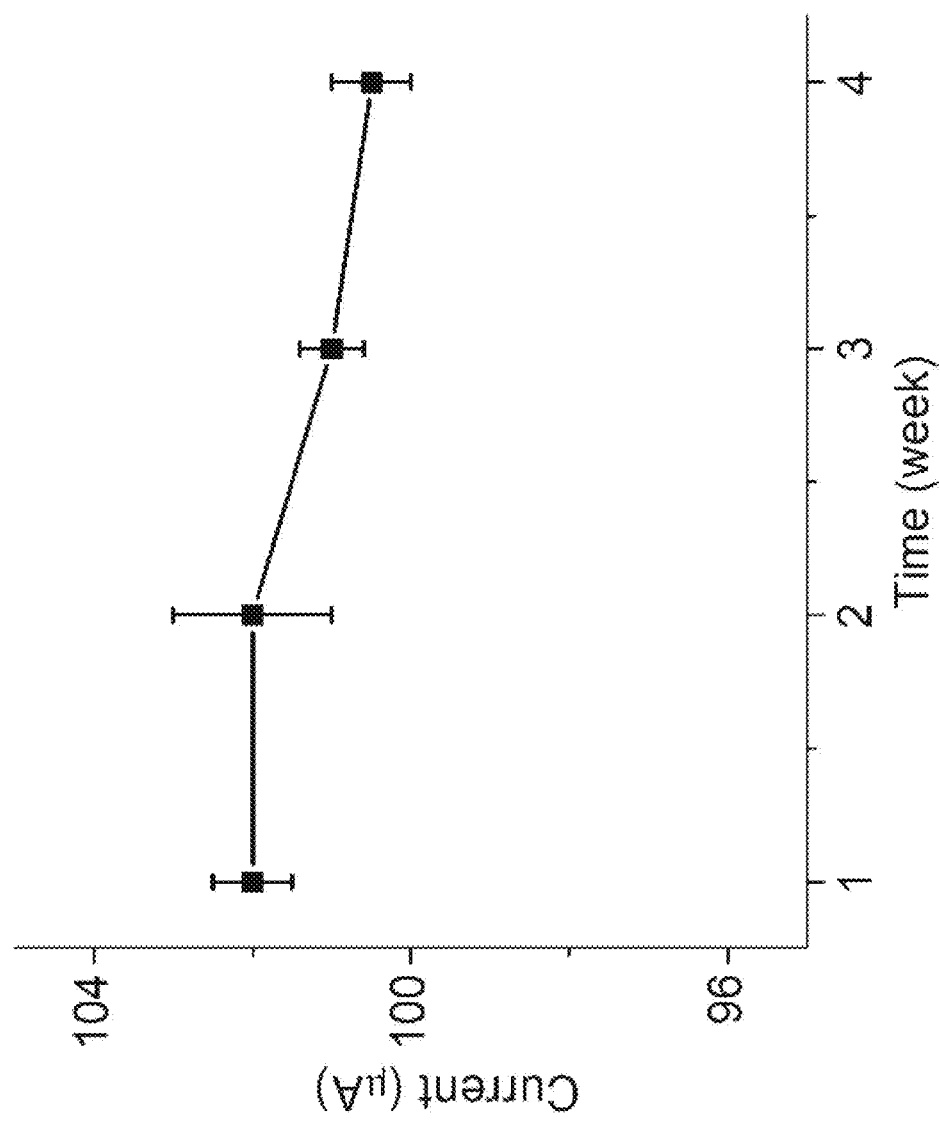

The sensor was further examined for reproducibility with four identical sensors using the CA technique in presence of 1.0 fM concentration of ErbB2. This sensor shows a high reproducibility with a minute deviation (RSD: ±1.95%) (FIG. 5E). The obtained high reproducibility of the sensor may be due to the high periodicity and uniform assembly of the Au nanoposts. In addition, the stability test for the nanoposts-based sensor was conducted once a week over a four-week period. For each measurement, the sensor was washed with the PBS solution to remove unbound molecules from the sensor surface. When not in use, the sensor was stored at 4° C. to avoid denature of antibody on the sensor surface. Overall, this sensor exhibited a stable amperometric signature (FIG. 5F), although after three weeks, a 1.2±0.3% reduction in output current was found.

Figure 6A:
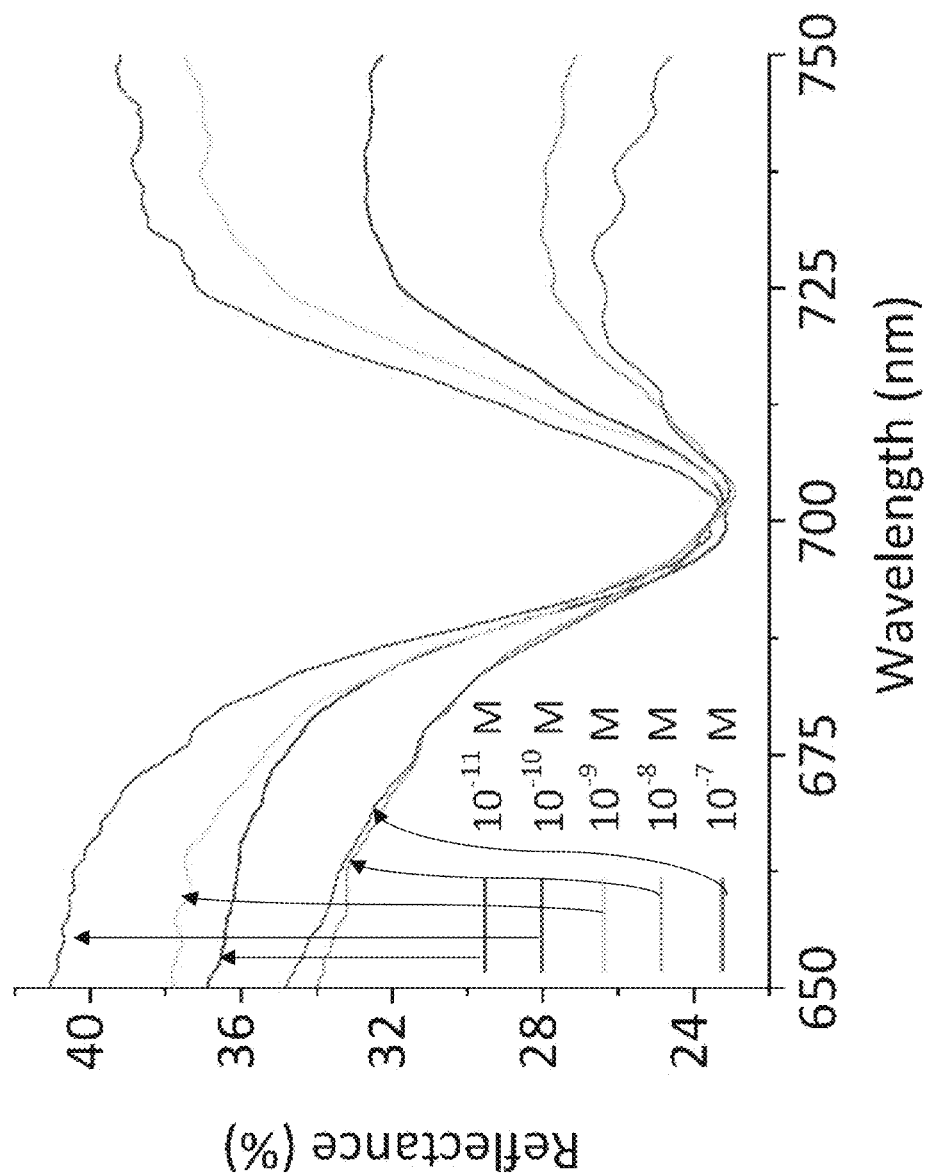

4.4. SPR detection of biomarker. In addition to the electrochemical sensing, the microfluidic sensor was used to conduct the SPR-based detection of ErbB2 antigen biomarker. It was found that when the ErbB2 concentrations were lower than 10 pM, the resonance wavelength of the sensor was almost insensitive to changes in ErbB2 concentration. This is because the resulting refractive index variation was too small to be detected by this plasmonic sensor. At plasmonic resonances, optical energy dissipations in Au result in a low Q-factor of resonances that restricts the sensitivity of the sensor. FIG. 6A shows the SPR spectra of this sensor as a function of ErbB2 concentration ranging from 10 pM to 0.1 µM in the PBS solution (pH=7.4). A reflection dip was found at the resonance wavelength of 701.6 nm with 10 pM ErbB2 concentration when the anti-ErbB2 conjugated nanoposts array was excited by the normal incident light. As the ErbB2 concentration increased from 10 pM to 0.1 nM, 1 nM, 10 nM and 0.1 µM, the resonance wavelength of the sensor redshifted from 701.6 nm to 703.1 nm, 704.3 nm, 705.2 nm and 705.9 nm, respectively.

Figure 6B:
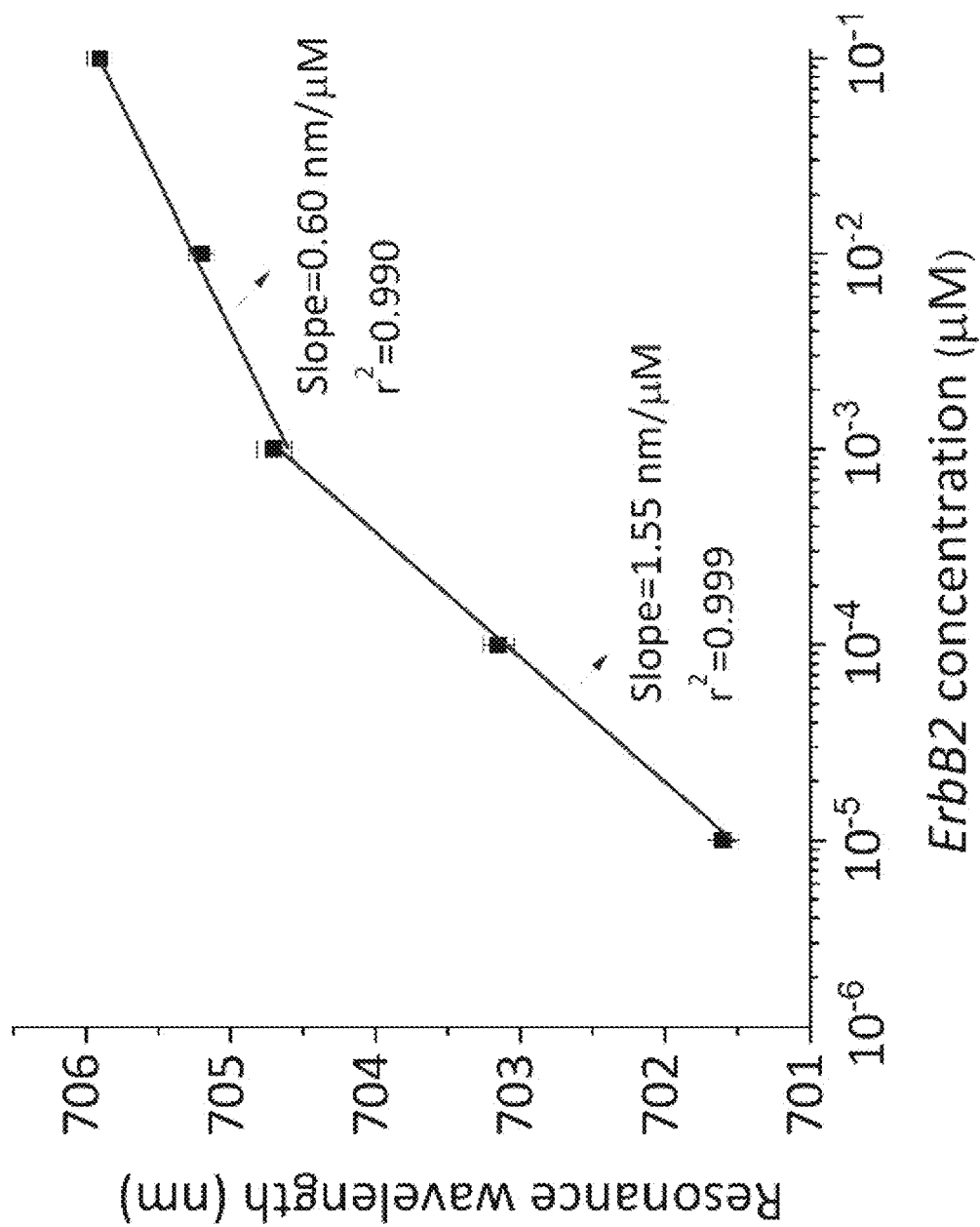

The sensor surface was cleaned with the PBS solution before introducing a new analyte solution on the sensor surface. FIG. 6B shows the calibration plot of the sensor between the logarithmic ErbB2 concentrations and the SPR resonance wavelengths. The resonance shifted towards higher wavelengths with increasing concentration, resulting from the specific binding of ErbB2 molecules increasing the refractive index at the sensor surface. This sensor shows a sensitivity of 1.35 nm/µM within the concentration range of ErbB2 from 10 pM to 1 nM and a sensitivity of 0.80 nm/µM within the concentration range of ErbB2 from 1 nM to 0.1 µM.

Figure 6C:
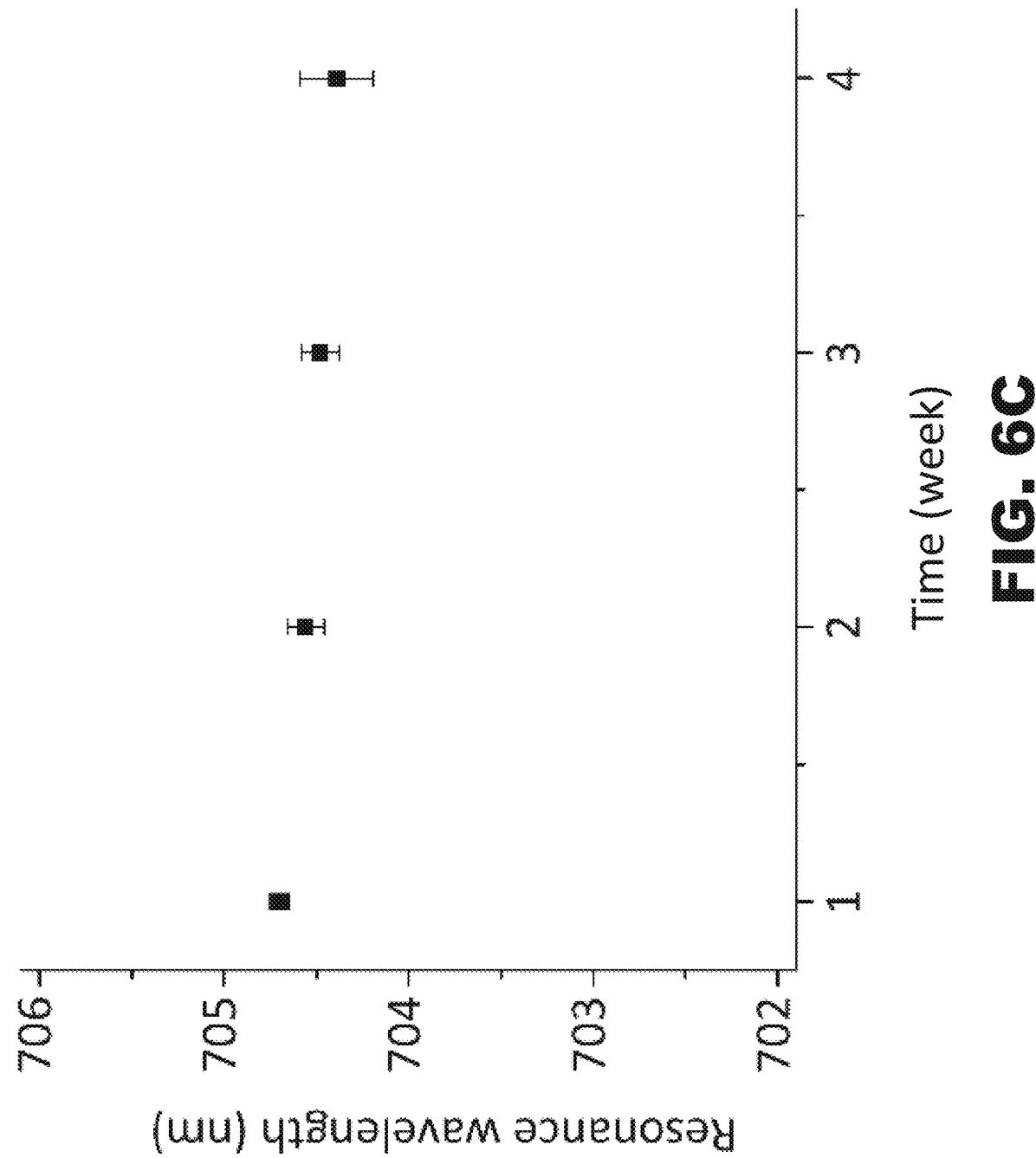

The stability test for the SPR measurement was conducted once every week over a four-week period (FIG. 6C). During each measurement, the sensor was exposed to 1 nM ErbB2 concentration and the obtained resonance wavelength was recorded. After the test, the sensor surface was washed by flowing the PBS solution (pH=7.4) into the channel and then was stored at 4° C. until next test. The result shows that after four weeks, the resonance wavelength for 1 nM ErbB2 concentration exhibited a minor shift of about 0.35 nm towards shorter wavelengths, compared to that obtained initially (704.7 nm resonance wavelength), which may be caused by denaturation of immobilized anti-ErbB2 molecules.

Figure 6D:
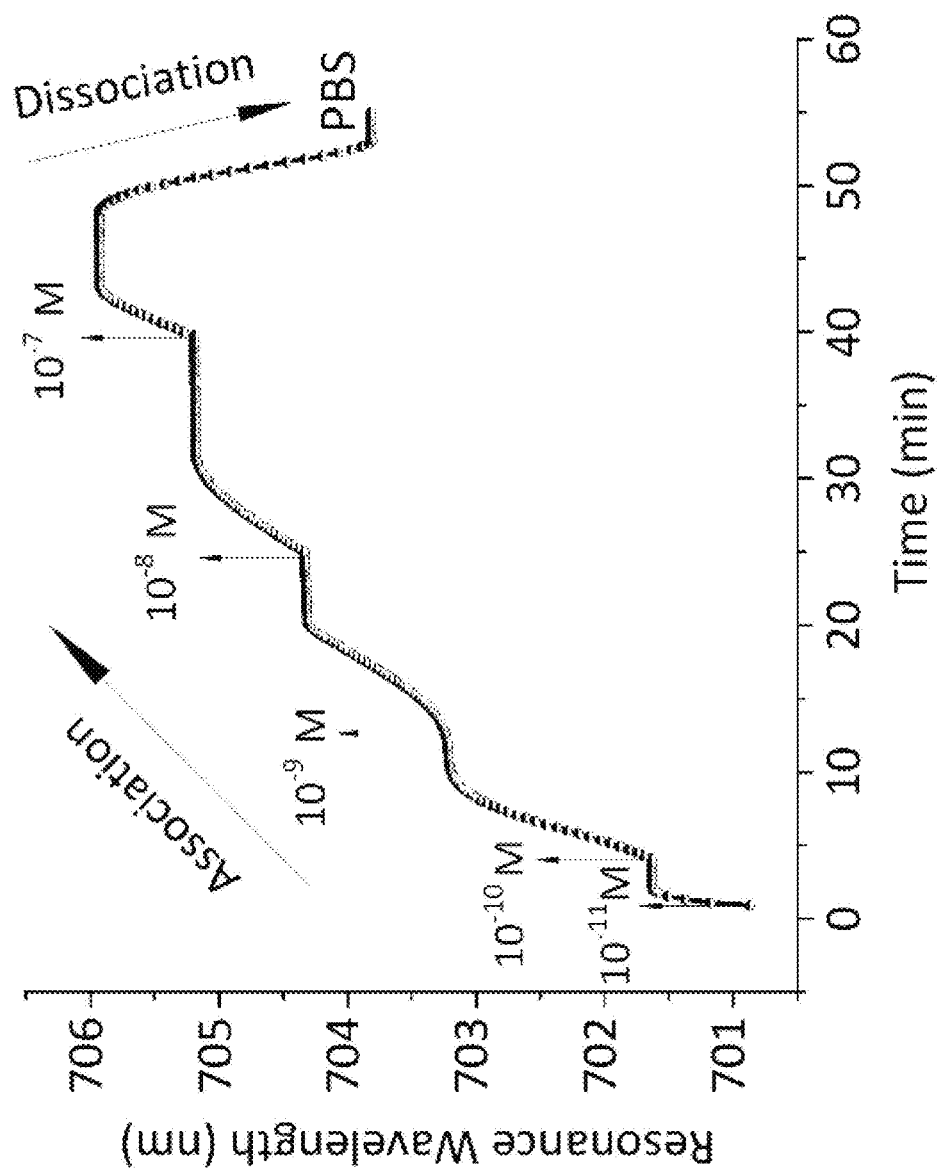

FIG. 6D demonstrates the ability of the sensor to optically track binding kinetics of antigen-antibody interactions at the sensor surface as the ErbB2 concentration increased from 10 pM to 0.1 nM, 1 nM, 10 nM and 0.1 µM in the PBS solution (pH=7.4) with the same redox mediator. The sensor surface was first covered by the PBS solution, and then, the ErbB2 (10 pM) solution flowed into the channel. This association phase induced a redshift of 0.7 nm. As the ErbB2 concentration increased from 10 pM to 0.1 nM, this sensor provided a redshift of 1.5 nm in the association phase. When the ErbB2 concentration further increased to 1 nM, 10 nM and 0.1 µM, the resonance redshifted by 1.15 nm, 0.9 nm, and 0.7 nm respectively. In the dissociation phase, the sensor was washed with the PBS solution to remove the loosely bound ErbB2 molecules from the surface of the nanoposts, resulting in shifting the resonance wavelength to 703.8 nm.

Using the Hill equation[54], the association ($K_a$) and dissociation ($K_d$) constants for the ErbB2 antigen and anti-ErbB2 immunocomplex have been calculated. The $K_a$ and $K_d$ of antibody and antigen can be expressed as $$nAg + Ab \frac{K_a}{K_d} Ag_n Ab,$$

where n is known as the Hill coefficient, Ag is ErbB2 captured by the sensor and Ab is ant-ErbB2 immobilized on nanoposts surface. The equilibrium constant $K_d$ is given by $K_d=[Ag]^n[Ab]/[Ag_n Ab]$, where $K_d$ is the reciprocal of $K_a$, and n can be estimated using the Hill plot. The Hill plot is the curve between log θ and log (ErbB2) and θ is given by ∝=Y/(1−Y), a ratio of the amount of bound ErbB2 to the amount of immobilized anti-ErbB2 and Y is the ratio of the change of wavelength and maximum wavelength. The values of $K_d$, $K_a$ and n are found as 0.472×10$^{-6}$ M, 2.11 ×10$^6$ M, and 0.207, respectively. With n (0.207)<1, i.e. the cooperativity is negative. When the ErbB2 molecule binds to specific anti-ErbB2, the affinity of this anti-ErbB2 to non-specific species declines. The higher association constant of anti-ErbB2 conjugated nanoposts indicates a higher affinity towards specific ErbB2 antigen.

Figure 7B:
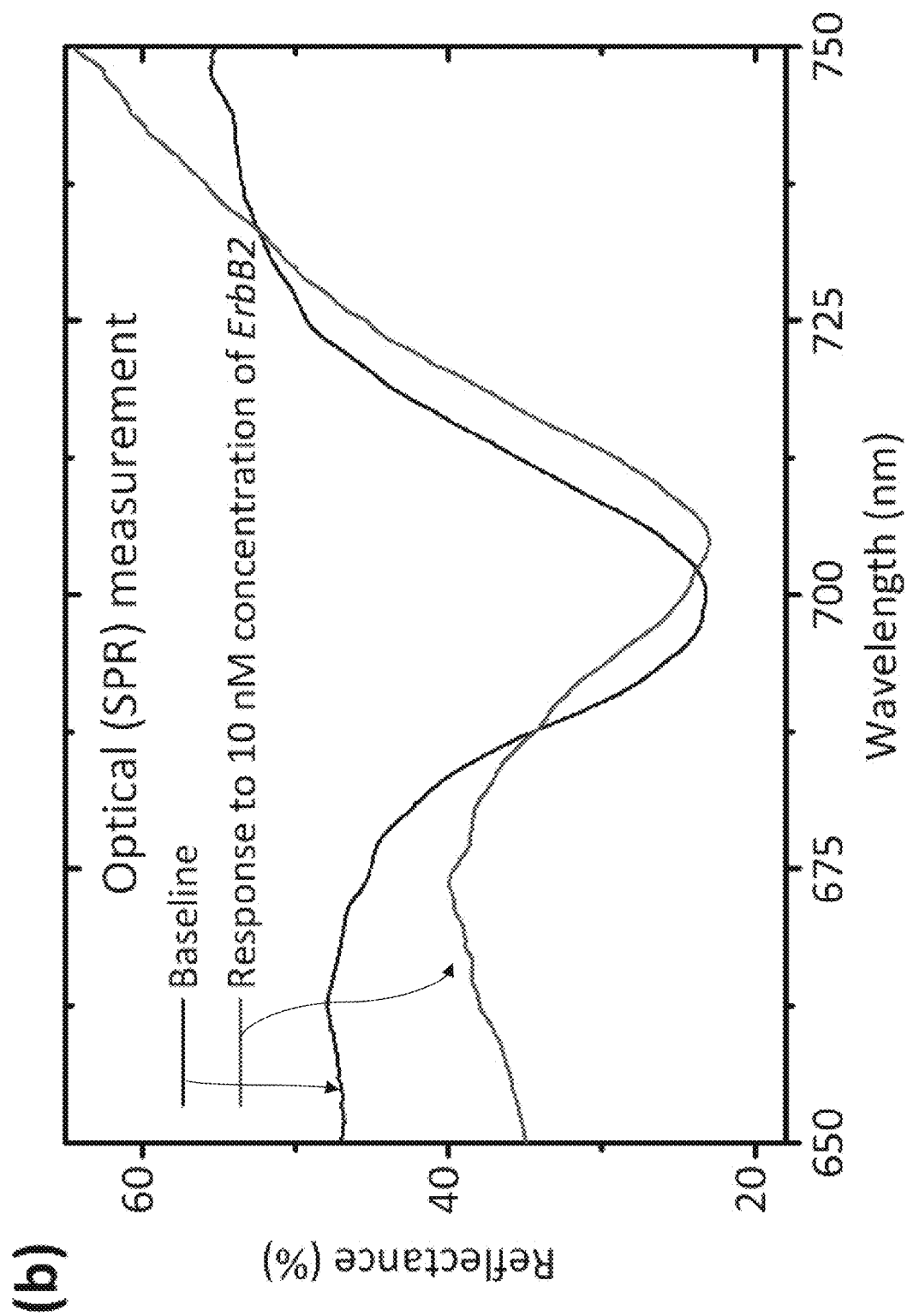
Figure 8A:
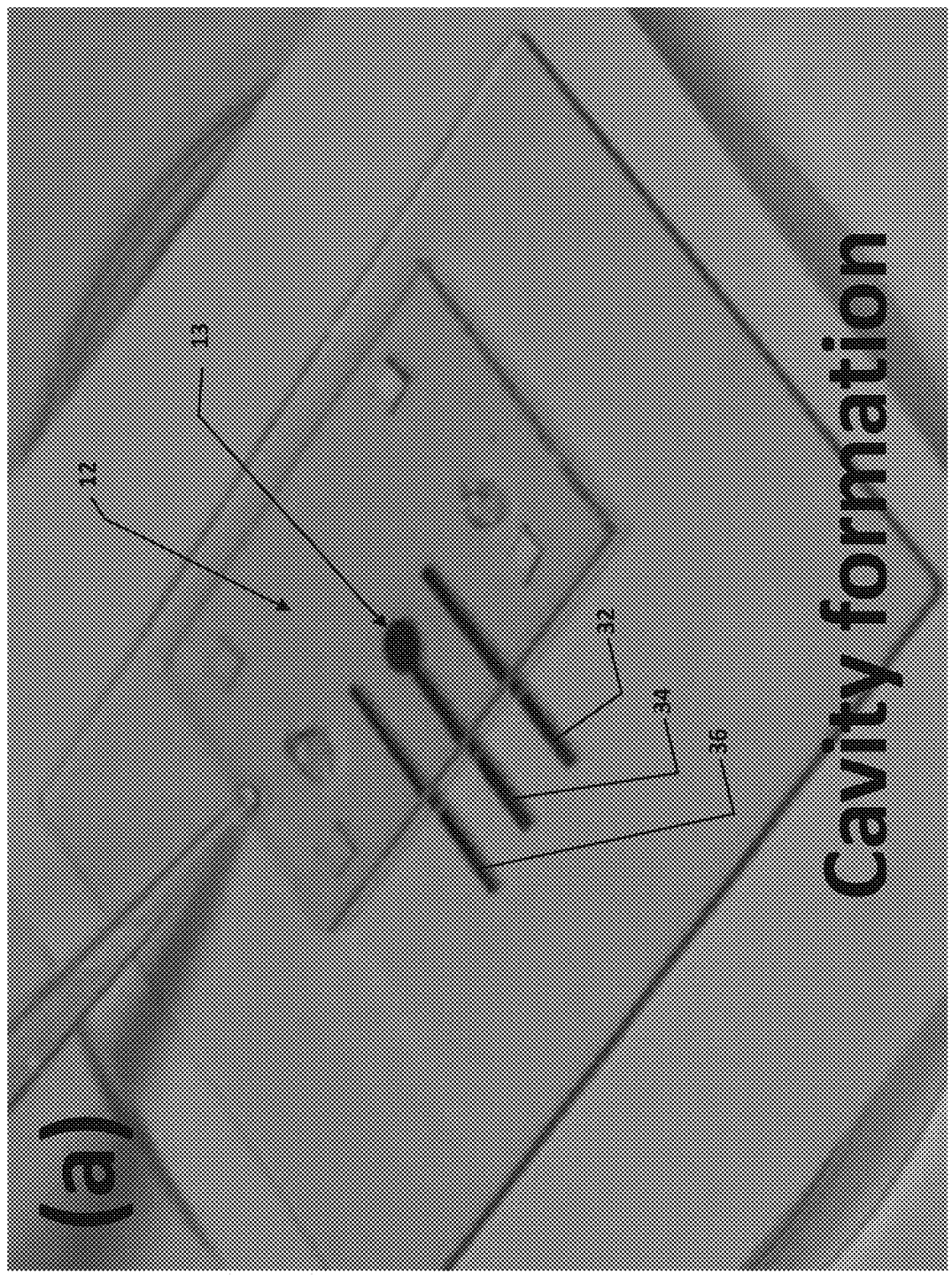
Figure 8B:
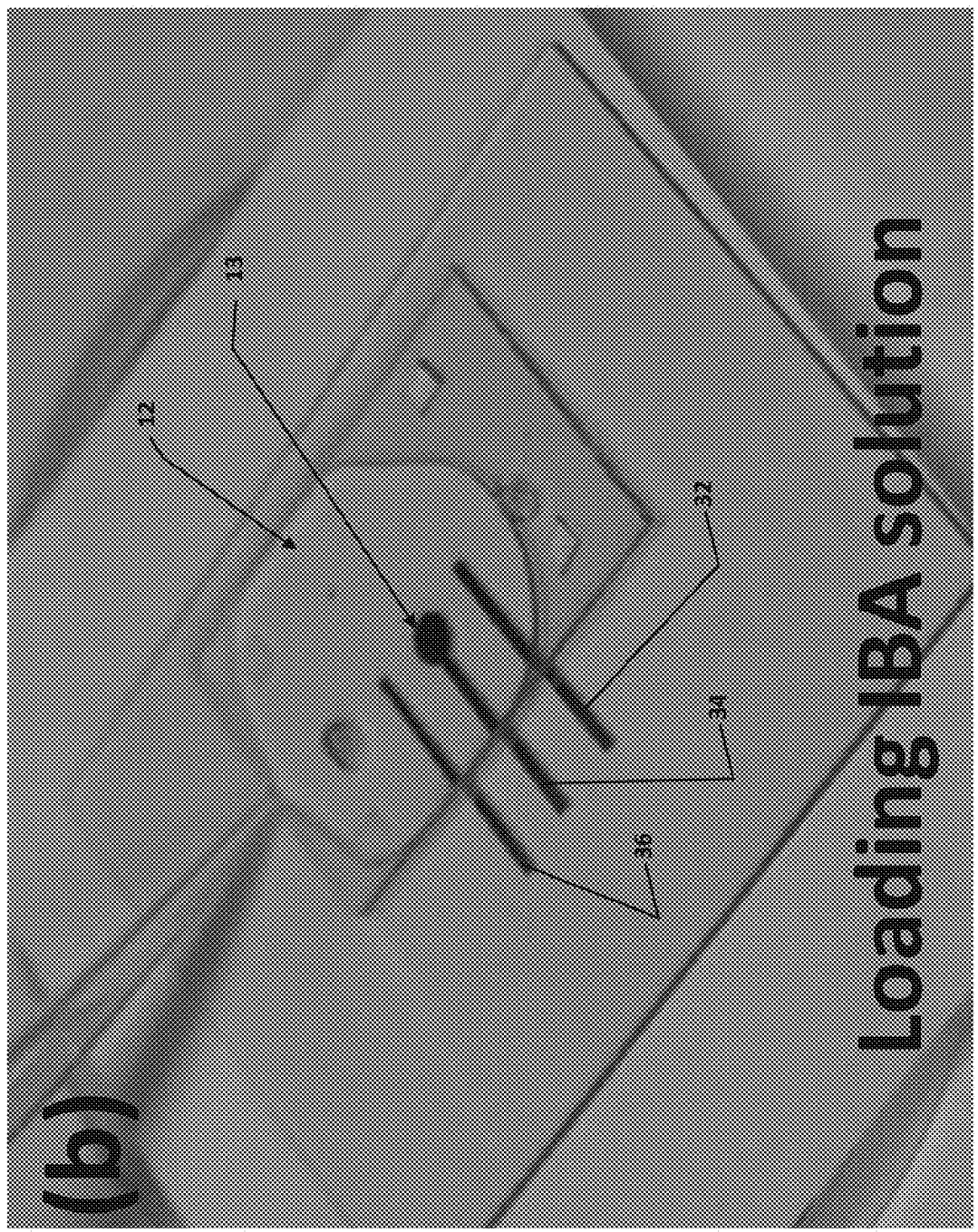
Figure 8C:
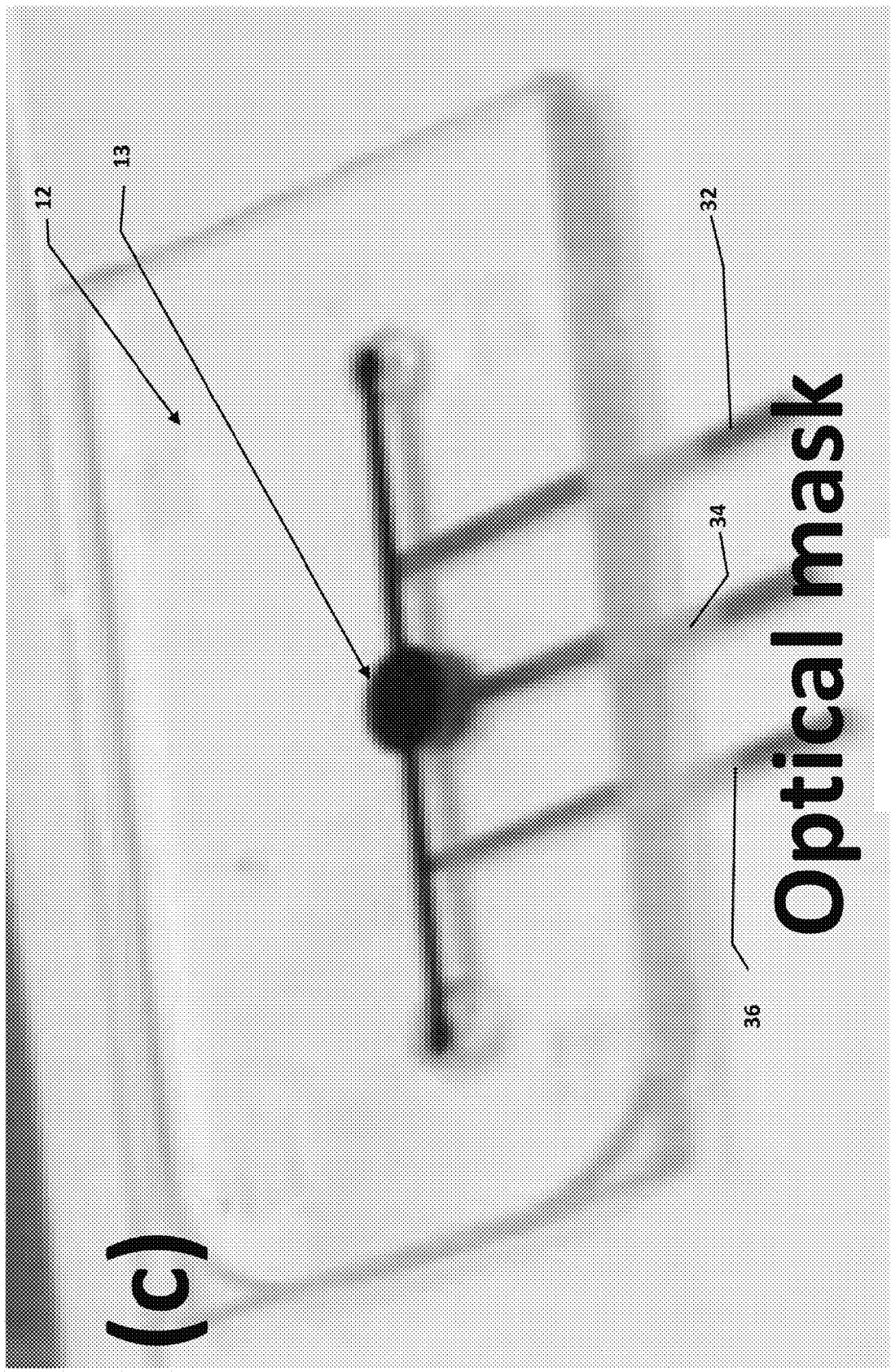
Figure 8D:
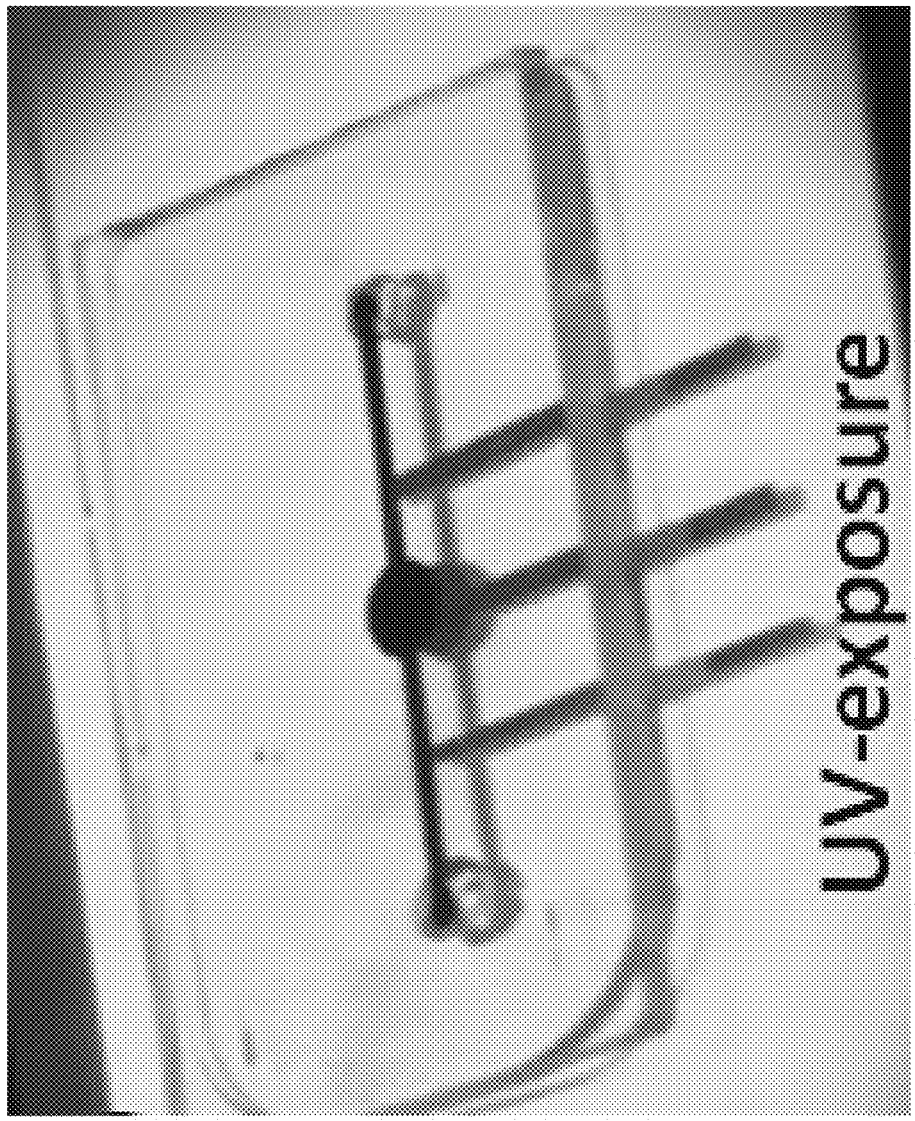
Figure 8E:
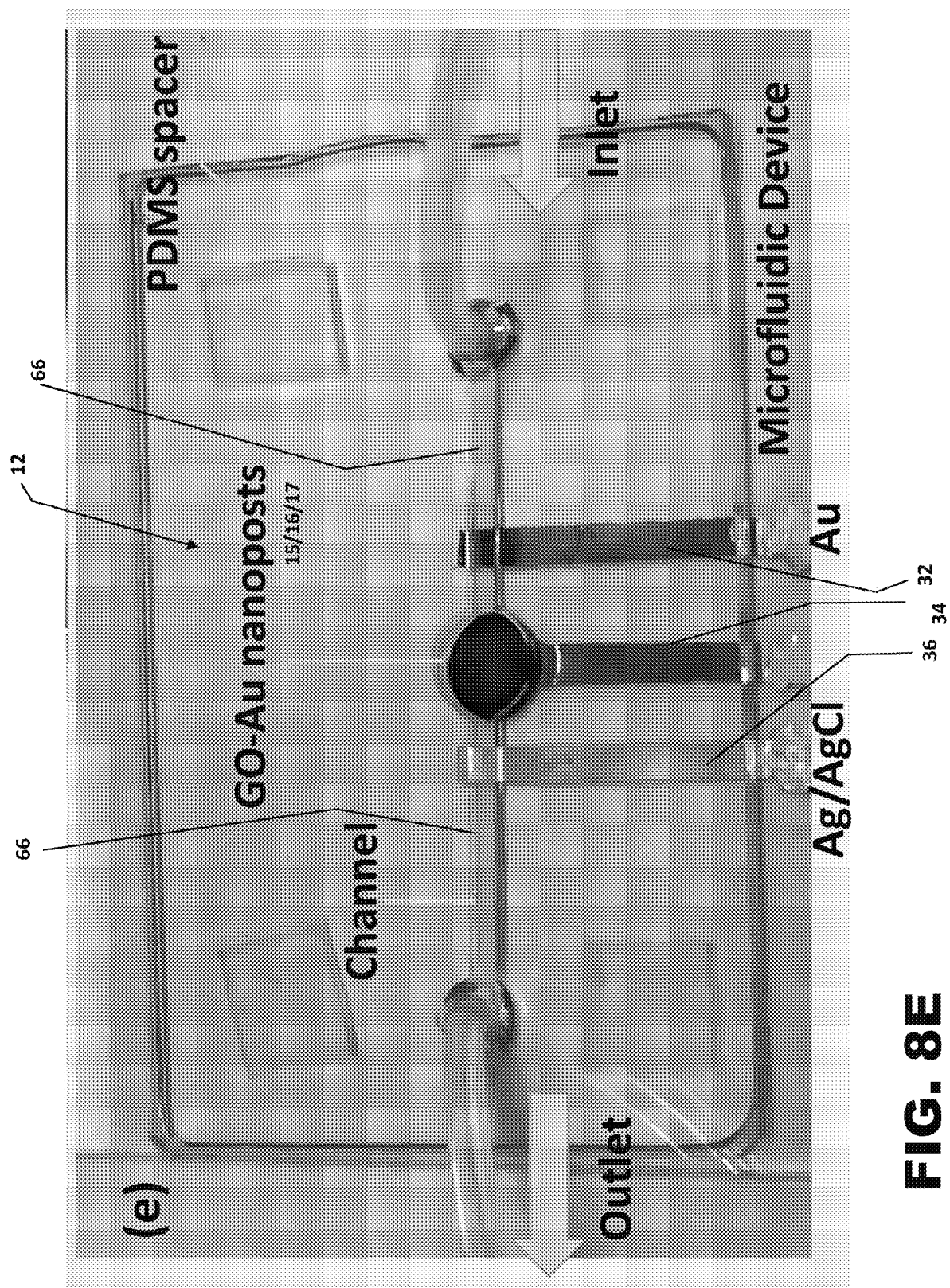

4.5. Simultaneous measurements using dual modalities. We conducted both the electrochemical and SPR measurements simultaneously using the dual-modality sensor in the presence of 10 nM concentration of ErbB2 molecules. As shown in FIGS. 7A-B, the electrochemical measurement shows a reduction in chronoamperometric current from 105 µA (i.e., the baseline current) to 88.5 µA. Based on the electrochemical calibration curve (FIG. 5C), the ErbB2 concentration obtained using the electrochemical measurement is 10.1±0.4 nM (mean±standard deviation for 5 measurements), which agrees well with the known concentration of 10 nM. At the same time, the SPR measurement shows that the resonance wavelength of the sensor redshifis from 699 nm (i.e., the baseline wavelength) to 705.2 nm. Correspondingly, based on the SPR calibration curve (FIG. 6B), the obtained ErbB2 concentration is 10.2±0.3 nM (mean±standard deviation for 5 measurements). Therefore, the electrochemical and SPR measurements using the single sensor provide almost consistent results for the detection of ErbB2 molecules when the ErbB2 concentration under measurement falls in the common dynamic range of both the methods.

4.6. Comparison with state-of-art sensors. Tables 2 and 3 compare the performance of this sensor with many reported sensors for the detection of ErbB2 biomarker. Compared to the electrochemical sensors using graphene foam-$TiO_2$[51], Au nanoparticles[55], and $GO$-$SiO_2$ nanoparticles[17], and the optical sensors using microrings[56], 1D distributed feedback grating[57] the present integrated dual-modality sensor offers a competitive detection range of 1.0 fM-0.1 μM, and a high sensitivity of 20.47 μA μM$^{-1}$ cm$^{-2}$ for the electrochemical detection (Table 2), and a sensitivity of 1.35 nm μM$^{-1}$ in the concentration range of 10 pM-1 nM, a sensitivity of 0.80 nm μM$^{-1}$ in the concentration range of 1 nM-0.1 μM for the SPR detection (Table 3) of ErbB2.

The present integrated dual-modality sensor incorporates both electrochemical and SPR detection methods on a single nanopattemed substrate for recognizing and quantifying ErbB2 breast cancer biomarker, offering many novelties:

(a) The integrated dual-modality design potentially will help increase detection reliability, due to the ability of the sensor to generate two readouts for a specific antigen-antibody reaction at the sensor surface.

(b) The electrochemical detection mode of the sensor benefits from the presence of the lithographically formed nanoposts on the surface of the working electrode, enabling efficient radial diffusion of redox species. This provides a fM-level limit of detection (LOD) for quantifying ErBb2 biomarker using the electrochemical mode, which will be clinically important to early-stage cancer diagnosis.

(c) While the SPR detection mode has a higher LOD (on the order of 10 pM for ErBb2), it enables dynamic tracking of antigen-antibody interactions at the same surface where the electrochemical detection takes place. The ability to track association and dissociation processes will potentially help scientists to better understand molecular recognition behaviors for optimizing a target antibody for a specific antigen.

(d) Further, from a sample consumption perspective, the required sample volume used in the presented integrated dual-modality sensor is less than that used in two spatially separated electrochemical and SPR sensors.

TABLE 2

Comparison of the performance of our electrochemical sensor with that of other electrochemical immunosensors for the detection of ErbB2 biomarker.

| Electrochemical working electrodes | Measurement methods | Sensitivity | Dynamic range (pM) | Limit of detection (pM) | Ref. |
| --- | --- | --- | --- | --- | --- |
| Au nanoparticles | Electrochemical (voltammetry) | 2.2 μA pM$^{-1}$ cm$^{-2}$ | $7.25 \times 10^{-4}$-72.5 | $2.68 \times 10^{-4}$ | 55 |
| Graphene foam-$TiO_2$ | Electrochemical (voltammetry) | 0.585 μA μM$^{-1}$ cm$^{-2}$ | $0.001$-$1.0 \times 10^5$ | 0.001 | 51 |
| Graphene oxide-$SiO_2$ nanoparticles | Electrochemical (Impedance) | NA | $1$-$1 \times 10^6$ | 1.0 | 17 |
| Functionalized ZnO nanofibers | Electrochemical (Impedance) | 7.76 kΩ μM$^{-1}$ cm$^{-2}$ | $0.001$-$5.0 \times 10^5$ | 0.001 | 58 |
| Cysteamine-AuNPs | Electrochemical (Impedance) | 3.83 kΩ pM$^{-1}$ | $0.0072$-$7.2 \times 10^3$ | 0.0024 | 59 |
| Au—GO nanoposts | Electrochemical (Amperometry) | 20.47 μA μM$^{-1}$ cm$^{-2}$ | $0.001$-$1 \times 10^5$ | 0.001 | This work |

TABLE 3

Comparison of the performance of our SPR sensor with that of other optical immunosensors for the detection of ErbB2 biomarker.

| Optical resonators | Measurement methods | Sensitivity (nm μM$^{-1}$) | Dynamic range (pM) | Limit of detection (PM). | Ref. |
| --- | --- | --- | --- | --- | --- |
| Optofluidic ring resonator | Whispering gallery mode | 74.2 27.4 | 94-240 362-725 | 72 | 56 |
| ID distributed feedback grating | First-order diffraction mode | 4.6 | $75$-$5.4 \times 10^4$ | 75 | 57 |
| Au—GO nanoposts | SPR mode | 1.35 0.8 | $10$-$1 \times 10^3$ $1 \times 10^3$-$1 \times 10^5$ | 10 | This work |

5. Conclusions

To summarize, an integrated dual-modality sensor integrating electrochemical and SPR measurements was developed for the detection of a breast cancer biomarker. The substrate for SPR detection consists of an array of periodically arranged Au nanoposts functionalized with GO nanosheets and antibody (anti-ErbB2), while the same Au nanoposts also serve as a working electrode of the integrated electrochemical sensor. In addition to increasing the surface area and loading capability for the immobilized anti-ErbB2 molecules, these nanoposts enable SPR, and also serve as the vertical nanoelectrodes enabling the radial diffusion of redox species onto the sensor surface. The sensor with the nanoposts exhibits 5.4-fold enhancement in output current and a 3-fold reduction in response time, compared to the counterpart device with the planar electrode. The SPR detection mode allows a dynamic tracking of the associations and dissociations of biomarker molecules, which is generally a limitation of an electrochemical sensor. Unlike the nanoparticles, nanotubes, and nanowires-based sensors, this integrated dual-modality sensor offers an excellent reproducibility due to the ordered and uniform nanostructures.

NOTES AND REFERENCES (EACH OF WHICH IS INCORPORATED BY REFERENCE HEREIN IN ITS ENTIRETY)

(1) Hu, Y.; Fine, D. H.; Tasciotti, E.; Bouamrani, A.; Ferrari, M.; Nanodevices in diagnostics. *Wiley Interdiscip. Rev. Nanomed Nanobiotechnol.* 2011,3,11-32.

(2) Jemal, A.; Siegel. R.; Ward, E.; Hao, Y.; Xu, J.; Murray, T.; Thun, M. J. Cancer statistics, *CA Cancer J. Clin.* 2008,58,71-96.

(3) Powers, A.; Palecek, S. Protein analytical assays for diagnosing, monitoring, and choosing treatment for cancer patients. *J. Healthc. Eng.* 2012, 3, 503-34.

(4) Gauchez, A. S.; Ravanel, N.; Villemain, D.; Brand, F. X.; Pasquier, D.; Payan, R.; Mousseau, M. Evaluation of a manual ELISA kit for determination of HER2/neu in serum of breast cancer patients. *Anticancer Res.* 2008, 28, 3067-73.

(5) Malhotra, R.; Patel, V.; Chikkaveeraiah, B. V.; Munge, B. S.; Cheong, S. C.; Zain, R. B.; Abraham, M. T.; Dey, D. K.; Gutkind, J. S.; Rusling, J. F.; Ultrasensitive detection of cancer biomarkers in the clinic by use of a nanostructured microfluidic array. *Anal. Chem.* 2012, 84, 6249-55.

(6) Hu, M.; Yan, J.; He, Y.; Lu, H.; Weng, L.; Song, S.; Fan, C.; Wang, L. Ultrasensitive, multiplexed detection of cancer biomarkers directly in serum by using a quantum dot-based microfluidic protein chip. *ACS Nano* 2009, 4, 488-94.

(7) Richard, J.; Sainsbury, C.; Needham, G.; Famdon, J.; Malcolm, A.; Harris, A. Epidermal-growth-factor receptor status as predictor of early recurrence of and death from breast cancer. *The Lancet* 1987, 329, 1398-402.

(8) Sainsbury, J. R.; Sherbet, G. V.; Famdon, J. R.; Harris, A. L. Epidermal-growth-factor receptors and oestrogen receptors in human breast cancer. *The Lancet* 1985, 325, 364-6.

(9) Zhang, H.; Berezov, A.; Wang, Q.; Zhang, G.; Drebin, J.; Murali, R.; Greene, M. I.; ErbB receptors: from oncogenes to targeted cancer therapies. *J. Clin. Invest.* 2007, 117, 2051-8.

(10) Iqbal, N.; Iqbal, N.; Human epidermal growth factor receptor 2 (HER2) in cancers: overexpression and therapeutic implications. *Mol. Biol. Int.* 2014, 2014, 490308.

(11) Venkatesan, B. M.; Bashir, R. Nanopore sensors for nucleic acid analysis. Nat. *Nanotechnol.* 2011, 6, 615-24.

(12) Stem, E.; Vacic, A.; Rajan, N. K.; Criscione, J. M.; Park, J.; Hie, B. R.; Mooney, D. J.; Reed, M. A.; Fahmy, T. M. Label-free biomarker detection from whole blood. *Nat. Nanotechnol.* 2010, 5, 138-42.

(13) Eftekhari, F.; Escobedo, C.; Ferreira, J.; Duan, X.; Girotto, E. M.; Brolo, A. G.; Gordon, R.; Sinton, D. Nanoholes as nanochannels: flow-through plasmonic sensing. *Anal. Chem.* 2009, 57, 4308-11.

(14) Stewart, M. E.; Anderton, C. R.; Thompson, L. B.; Maria, J.; Gray, S. K.; Rogers, J. A.; Nuzzo, R. G. Nanostructured plasmonic sensors. *Chem. Rev.* 2008, 108, 494-521.

(15) Heller, D. A.; Jin, H.; Martinez, B. M.; Patel, D.; Miller, B. M.; Yeung, T. K.; Jena, P. V.; Httbartner, C.; Ha, T.; Silverman, S. K.; Strano, M. S. Multimodal optical sensing and analyte specificity using single-walled carbon nanotubes. *Nat. Nanotechnol.* 2009, 4, 114-20.

(16) Kondrashina, A. V.; Dmitriev, R. I.; Borisov, S. M.; Klimant, I.; O'Brien, I.; Nolan, Y. M.; Zhdanov, A. V.; Papkovsky, D. B. A phosphorescent nanoparticle-based probe for sensing and imaging of (intra) cellular oxygen in multiple detection modalities. *Adv. Funct. Mater.* 2012, 22, 4931-9.

(17) Myung, S.; Solanki, A.; Kim, C.; Paric, J.; Kim, K. S.; Lee, K. B. Graphene-encapsulated nanoparticle-based biosensor for the selective detection of cancer biomarkers. *Adv. Mater.* 2011, 23, 2221-5.

(18) Zheng, G.; Patolsky, F.; Cui, Y.; Wang, W. U.; Lieber, C. M. Multiplexed electrical detection of cancer markers with nanowire sensor arrays. *Nat. Biotechnol.* 2005, 23, 1294-301.

(19) Heinze, J. Ultramicroelectrodes in electrochemistry. *Angew. Chem. Int. Ed Engl.* 1993, 32, 1268-88.

(20) Forster, R. J. Microelectrodes: new dimensions in electrochemistry. *Chem. Soc. Rev.* 1994, 23, 289-97.

(21) Sandison, M. E.; Cooper, J. M. Nanofabrication of electrode arrays by electron-beam and nanoimprint lithographies. *Lab Chip* 2006, 6, 1020-5.

(22) Lu, L. M.; Li, H. B.; Qu, F.; Zhang, X. B.; Shen, G. L.; Yu, R. Q. In situ synthesis of palladium nanoparticle-graphene nanohybrids and their application in nonenzymatic glucose biosensors. *Biosens. Bioelectron.* 2011, 26, 3500-4.

(23) Li, X.; Zhao, C.; Liu, X. A paper-based microfluidic biosensor integrating zinc oxide nanowires for electrochemical glucose detection. *Microsystems & Nanoengineering* 2015,9,1-7.

(24) Vilela, D.; Garoz, J.; Colina, A.; Gonzdlez, M. C.; Escarpa, A. Carbon nanotubes press-transferred on PMMA substrates as exclusive transducers for electrochemical microfluidic sensing. *Anal. Chem.* 2012, 84, 10838-44.

(25) Mondal, K.; Ali, Md. A.; Agrawal, V. V.; Malhotra, B. D.; Sharma, A. Highly sensitive biofunctionalized mesoporous electrospun $TiO_2$ nanofiber based interface for biosensing. *ACS Appl. Mater. Interfaces* 2014, 6, 2516-27.

(26) Yang, L. and Dong, L., Selective nanofiber deposition using a microfluidic confinement approach, *Langmuir* 2010, 26, 1539-43.

(27) Law, W. C.; Yong, K. T.; Baev, A.; Prasad, P. N. Sensitivity improved surface plasmon resonance biosensor for cancer biomarker detection based on plasmonic enhancement. *ACS Nano* 2011, 5, 4858-64.

(28) Brigham-Burke, M.; Edwards, J. R.; O'Shannessy, D. J. Detection of receptor-ligand interactions using surface plasmon resonance: model studies employing the HIV-1 gp120/CD4 interaction. *Anal. Biochem.* 1992, 205, 125-31.

(29) Stewart, M. E.; Mack, N. H.; Malyarchuk, V.; Soares, J. A.; Lee, T. W.; Gray, S. K.; Nuzzo, R. G.; Rogers, J. A. Quantitative multispectral biosensing and 1D imaging using quasi-3D plasmonic crystals. *Proc. Natl. Acad. Sci.* 2006, 103, 17143-8.

(30) Brockman, J. M.; Frutos, A. G.; Corn, R. M. A multistep chemical modification procedure to create DNA arrays on gold surfaces for the study of protein-DNA interactions with surface plasmon resonance imaging. *J. Am. Chem. Soc.* 1999, 121, 8044-51.

(31) Karlsson, R.; Ffilt, A. Experimental design for kinetic analysis of protein-protein interactions with surface plasmon resonance biosensors. *J. Immunol. Methods* 1997, 200, 121-33.

(32) Marinakos, S. M.; Chen, S.; Chilkoti, A. Plasmonic detection of a model analyte in serum by a gold nanorod sensor. *Anal. Chem.* 2007, 79, 5278-83.

(33) Yu, C.; Irudayaraj, J. Multiplex biosensor using gold nanorods. *Anal. Chem.* 2007, 79, 572-9.

(34) Cinel, N. A.; Bütün, S.; Özbay, E. Electron beam lithography designed silver nano-disks used as label free nano-biosensors based on localized surface plasmon resonance. *Opt. Express* 2012, 20, 2587-97.

(35) Scholder, O.; Jefimovs, K.; Shorubalko, I.; Hafner, C.; Sennhauser, U.; Bona, G. L. Helium Focused Ion Beam Fabricated Plasmonic Antennas with Sub-5 Nm Gaps. *Nanotechnology* 2013, 24, 395301.

(36) Truong, T. T.; Maria, J.; Yao, J.; Stewart, M. E.; Lee, T. W.; Gray, S. K.; Nuzzo, R. G.; Rogers, J. A. Nanopost plasmonic crystals. *Nanotechnology* 2009, 20, 434011.

(37) Haske, W.; Chen, V. W.; Hales, J. M.; Dong, W.; Barlow, S.; Marder, S. R.; Perry, J. W. 65 nm feature sizes using visible wavelength 3-D multiphoton lithography. *Opt. Express* 2007, 15, 3426-36.

(38) Fredriksson, H.; Alaverdyan, Y.; Dmitriev, A.; Langhammer, C.; Sutherland, D. S.; Zäch, M.; Kasemo, B. Hole-mask colloidal lithography. *Adv. Mater.* 2007, 19, 4297-302.

(39) Kim, K.; Kim, D. J.; Moon, S.; Kim, D.; Byun, K. M. Localized surface plasmon resonance detection of layered biointeractions on metallic subwavelength nanogratings. Nanotechnology 2009, 20, 315501.

(40) Escobedo, C. On-chip nanohole array based sensing: a review. *Lab Chip* 2013, 13, 2445-63.

(41) Das, G.; Battista, E.; Manzo, G.; Causa, F.; Netti, P. A.; Di Fabrizio, E. Large-scale plasmonic nanocones array for spectroscopy detection. *ACS Appl. Mater. Interfaces* 2015, 7, 23597-604.

(42) Tabassum, S.; Kumar, R.; Dong, L. Plasmonic crystal-based gas sensor toward an optical nose design, *IEEE Sensors Journal* 2017, 17, 6210-23.

(43) Im, H.; Sutherland, J. N.; Maynard, J. A.; Oh, S. H. Nanohole-based surface plasmon resonance instruments with improved spectral resolution quantify a broad range of antibody-ligand binding kinetics. *Anal. Chem.* 2012, 84, 1941-7.

(44) Johne, B.; Gadnell, M.; Hansen, K. Epitope mapping and binding kinetics of monoclonal antibodies studied by real time biospecific interaction analysis using surface plasmon resonance. *J. Immunol. Methods* 1993, 160, 191-8.

(45) Joe, S.-F.; Hsieh, L.-Z.; Chang, L.-B.; Hsu, C.-M.; Wu, C.-M. Kinetic analysis of antibody-antigen interactions using phase-detection-based surface plasmon resonance sensor system. *Jpn. J. Appl. Phys.* 2007, 46, 3114.

(46) Ali, Md. A.; Tabassum, S.; Wang, Q.; Wang, Y.; Kumar, R.; Dong, L. Plasmonic-electrochemical dual modality microfluidic sensor for cancer biomarker detection, in *Proc. IEEE 30$^{th}$ Int. Conf. Micro Electro Mech. Syst. (MEMS)*, Las Vegas, Nev., USA, 2017, 390-393.

(47) Wang, Q.; Han, W.; Liu, P.; Dong, L. Electrically tunable quasi-3-d mushroom plasmonic crystal. *J. Lightwave Technol.* 2016, 34, 2175-81.

(48) Beebe, D. J.; Moore, J. S.; Yu, Q.; Liu, R. H.; Kraft, M. L.; Jo, B. H.; Devadoss, C. Microfluidic tectonics: A comprehensive construction platform for microfluidic system. *Proc. Natl. Acad Set*, 2000, 97, 13488-93.

(49) Dong, L.; Agarwal, A. K.; Beebe, D. J.; Jiang, H. Adaptive liquid microlenses activated by stimuli-responsive hydrogels. *Nature* 2006, 442, 551-554.

(50) Ali, Md. A.; Mondal, K.; Wang, Y.; Jiang, H.; Mahal, N. K.; Castellano, M. J.; Sharma, A.; Dong, L.; In situ integration of graphene foam-titanium nitride based bio-scaffolds and microfluidic structures for soil nutrient sensors. *Lab Chip,* 2017, 17, 274-285.

(51) Ali, Md. A.; Mondal, K.; Jiao, Y.; Oren, S.; Xu, Z.; Sharma, A.; Dong, L. Microfluidic immuno-biochip for detection of breast cancer biomarkers using hierarchical composite of porous graphene and titanium dioxide nanofibers. *ACS Appl. Mater Interfaces* 2016, 8, 20570-82.

(52) Godino, N.; Borrise, X.; Munoz, F. X.; Del Campo, F. J.; Compton, R. G. Mass transport to nanoelectrode arrays and limitations of the diffusion domain approach: theory and experiment. *J. Phys. Chem. C* 2009, 113, 11119-25.

(53) Sharma, R.; Ali, Md. A.; Selvi, N. R.; Singh, V. N.; Sinha, R. K.; Agrawal, V. V. Electrochemically assembled gold nanostructures platform: electrochemistry, kinetic analysis, and biomedical application. *J. Phys. Chem. C* 2014, 118, 6261-71.

(54) Tajima, N.; Takai, M.; Ishihara, K. Significance of antibody orientation unraveled: well-oriented antibodies recorded high binding affinity. *Anal. Chem.* 2011, 83, 1969-76.

(55) Zhu, Y.; Chandra, P.; Shim, Y.-B. Ultrasensitive and selective electrochemical diagnosis of breast cancer based on a hydrazine-Au nanoparticle-aptamer bioconjugate. *Anal. Chem.* 2013, 85, 1058-1064.

(56) Gohring, J. T.; Dale, P. S.; Fan, X. Detection of HER2 breast cancer biomarker using the opto-fluidic ring resonator biosensor. *Sens. Actuators* B 2010, 146, 226-230.

(57) Retolaza, A.; Perdiguero, J. M.; Merino, S.; Vidal, M. M.; Boj, P. G.; Quintana, J. A.; Villalvilla, J. M.; Garcia, M. A. D. Organic distributed feedback laser for label-free biosensing of ErbB2 protein biomarker. *Sens. Actuators* B 2016, 223, 261-265.

(58) Ali, Md. A.; Mondal, K.; Singh, C.; Dhar Malhotra, B. D.; Sharma, A. anti-epidermal growth factor receptor conjugated mesoporous zinc oxide nanofibers for breast cancer diagnostics. Nanoscale 2015, 7, 7234-7245.

(59) Elshafey, R.; Tavares, A. C.; Siaj, M.; Zourob, M. Electrochemical impedance immunosensor based on gold nanoparticles-protein G for the detection of cancer marker epidermal growth factor receptor in human plasma and brain tissue. *Biosens. Bioelectron.* 2013, 50, 143-149.

Supporting Information

Also found at www.rsc.org/suppdata/c7/1c/c71c01211j/c71c012j1.pdf (both incorporated by reference in their entireties), incorporated by reference herein.

FIGS. 8A-E and 9 supplement the foregoing example and are discussed above.

D. Specific Example 2

Another example of aspects of the invention are set forth below. This example is similar to Specific Example 1, supra, but includes supplementing information.

Plasmonic-Electrochemical Dual Modality Microfluidic Sensor for Cancer Biomarker Detection Overview A dual-modality microfluidic immunosensor is reported for the detection of cancer biomarker proteins using graphene oxide assembled periodic gold nanoposts array. The sensor uniquely provides both electrochemical and surface plasmon resonance (SPR) signatures on a single platform. Sensitivities for both electrochemical and SPR detection schemes are found to be 3.94 $\mu A/\mu M/cm^2$ in a range of $1\times10^{-6}$ M to $0.1\times10^{-6}$ M, and 2.9 $nm/\mu M/cm^2$ in a range of $1\times10^{-15}$ M to $1\times10^{*-9}$ M, respectively, for the detection of epidermal growth factor receptor 2 (ErbB2) breast biomarker. The present dual-modality sensor approach enables improved detection reliability and precision and reduced false reads.

Introduction Early diagnostics of cancer biomarker requires a sensor to provide high sensitivity, specificity and reproducibility, as well as easy operation with minute sample consumptions [1]. Overexpression (~30%) of several receptor tyrosine kinases in ErbB2 is associated with increasing breast cancer metastasis [2]. Magnetic resonance and ultrasound imaging, X-ray mammography, computed tomography, ELISA, and immunohistochemistiy are the common methods to detect and quantify cancerous cells and tissues [3]. However, 80% of most breast cancers may not be detected by mammography due to the highly dense and proliferative cells. Moreover, large volume of samples and tagging molecules are required in ELISA and immunohistochemistry methods. Recently, numerous low-cost microfluidic sensors have been reported for cancer biomarker detection, demonstrating a great potential to realize rapid early-stage cancer diagnostics using only ultra-small sample consumptions without any complex and expensive procedures [4]. However, most of these sensors provide only a single modality of electrical, mechanical, electrochemical, or optical signal. With the continuing trend of minimizing sample consumptions, there will be an issue with the reliability and accuracy of biomarker detections associated with using low sample volumes available. Simultaneous generation of different sensing modalities from a single sensor may represent another method to improve reliability and reduce false (positive and negative) reads.

Label-free electrochemical sensors allow for rapid, and accurate detection and quantification of various chemical and biological species [5]. Micro/nanostructured materials have significant impacts on bio-recognition events and signal-transduction processes occurring at the electrochemical sensors, due to their large surface area, improved electron transport, and high electrochemical reactivity.[4] The electrochemical electrodes, modified by these micro/nanomaterials, can provide the radial or spherical diffusion of the redox species from the bulk solution to the surface of electrode, allowing for enhanced diffusion coefficient, as opposed to the slow, linear diffusion occurring at a planar or macroelectrode [6]. Therefore, the past two decades have witnessed a variety of high-performance electrochemical sensors modified by nanomaterials and nanostructures obtained using different synthesis methods, such as chemical vapor deposition, self-assembly, electrospinning hydrothermal, and phase separation [7]. However, owing to the generally evitable non-uniformity in size, geometry and spatial distribution of the chemically synthesized nanostructures, performance reproducibility of a number of nanostructured electrochemical sensors (even using the same type of nanomaterial) needs to be improved.

Label-free plasmonic biosensors, made of noble-metal nanostructures, can detect minute amounts of biomolecules via detecting subtle changes in refractive index induced by specific molecular binding or absorption at the surfaces of sensors [8]. The index variations can be translated into resonant spectral shifts or power changes. For example, various gold (Au) nanostructures are used to conjugate with different biomolecules for the sensitive detection of cancer biomarkers [8]. However, similar to the electrochemical sensors, many plasmonic nanostructures (e.g., nanoplates, nanoparticles, and nanorods) are obtained by non-lithographical fabrication methods. To attain spatial and structural uniformity of the plasmonic nanostructures [9], sophisticated nanofabrication techniques were adopted, such as electron-beam lithography, focused ion beam machining, nanoimprinting, and hole mask colloidal lithography.

Here, we present a dual-modality sensor 10' to detect and quantify cancer biomarkers with both electrochemical and plasmonic signals on a single microfluidic platform. The sensor 10' can provide not only high reproducibility of detection performances, but also a desirable new ability to quantify specific biomarkers in a small sample volume using two different sensing mechanisms, thus perceiving benefits to improve detection reliability and reduce false positives and negatives. The sensor (FIG. 11) was formed by a periodic array 13 of polymeric nanoposts 15 coated with Au (ref. no. 16). Graphene oxide (GO) 17 were assembled on the surfaces of the Au-coated nanoposts 15/16 to facilitate biofunctionalization with antibody molecules 18. The electrochemical detection of the device 10' provided several-fold enhancement of sensitivity for ErbB2 biomolecules, compared to a counterpart sensor using a planar electrode. The plasmonic detection of the sensor 10' provided detailed information related to binding kinetics occurring at the sensor surface 13, which complemented the relatively low ability of the electrochemical sensor to study molecular interactions between antigen 18 and antibody 19.

Sensor Principle and Structure

In both the electrochemical and plasmonic modes of operation, ErbB2 solutions were injected to the sensor through the inlet of a microfluidic channel. The detection principle relies on the specific immuno-interactions between target ErbB2 and anti-ErbB2 on the surface of nanoposts. The electrochemical measurement includes monitoring the generated current flow from the Au nanoposts array 13 (as a wording electrode 34) to the counter Au electrode 32 under an applied excitation potential between the Au nanoposts 15/16 and Ag/AgCl electrodes 36. In the SPR measurement, coupling of incident light to the Au nanoposts 15/16 provides a reflection dip owing to the excitation of (1, 0) surface plasmon polariton (SPP) at the air-Au nanoposts interface [10]. An increase in the concentration of ErbB2 antigen molecules 18 provides spectral shifts in SPR, as well as current changes in electrochemical measurement.

The sensor 10' was fabricated using soft lithography based replica molding technique. At first, an array of nanoholes 63 was formed in polydimethylsiloxane (PDMS) elastomer 62 from a silicon stamp 60 (which includes positives mold features 61 in the shapes of the ultimate nanoposts 15). Next, using a prepolymer solution (ZIPCONE™ UA or ZPUA 64), nanoposts 15 were printed on a glass substrate 66 from the PDMS mold 62. The obtained nanoposts 15 have a period of 500 nm, a diameter of 250 nm, and a height of 210 nm. Further, an 80 nm thick layer of Au 16 was deposited on the nanoposts 15 by e-beam evaporation. Step-wise illustrations for the formation of the Au nanoposts 15/16 (and a coating of GO 17) is shown in FIG. 12 (see steps a-f). To form an electrochemical sensor, an Au counter electrode 32 and a silver/silver chloride (Ag/AgCl) reference electrode 36 were formed on the two sides of the Au nanoposts area 13. Finally, the three-electrode sensor 10' was integrated with a microfluidic channel fabricated using an in-situ liquid phase polymerization ($LP^3$) process [11]. In this process, 0.4 mm thick PDMS spacers (see FIG. 11) were positioned between a 1 mm thick glass slide and the device substrate containing all electrodes to form an air cavity. A conventional milling machine with a 1-mm-diameter diamond drill bit was used to form the inlet and outlet holes through the top glass slide. Then, a photopattemable polymer consisting of isobornyl acrylate, tetraethylene glycol dimethacrylate, and 2,2-dimethoxy-2-phenylacetophenone were mixed at a weight ratio of 31.66:1.66:1.0 [11]. This solution was injected to fill the air cavity. A photomask was positioned on top of the glass slide and UV light (12 mW/cm$^2$) was used to expose the device for 60 s. The unpolymerized polymer was removed by rinsing the device in ethanol for 4 min, thus forming a microfluidic channel. FIG. 2 (steps g-h) show SEM images of the fabricated Au nanoposts 15/16.

The surface functionalization of Au nanoposts 15/16 was accomplished by self-assembling of GO nanosheets 17 that facilitated covalent immobilization of anti-ErbB2 due to the abundant functional groups (—CHO, —COOH, etc.) at GO nanosheets. The GO assembled Au nanoposts 15/16/17 were further functionalized with anti-ErbB2 18 via EDC-NHS coupling chemistry. For immobilization, a mixer solution of anti-ErbB2 (1 mg/mL) and EDC-NHS (EDC 0.2 M; NHS: 0.05 M) was prepared at 1:1 ratio. A 200 µL solution of this mixer was injected to the surface of the GO-Au nanoposts through the inlet of the channel.

RESULTS AND DISCUSSION

Figure 13A:
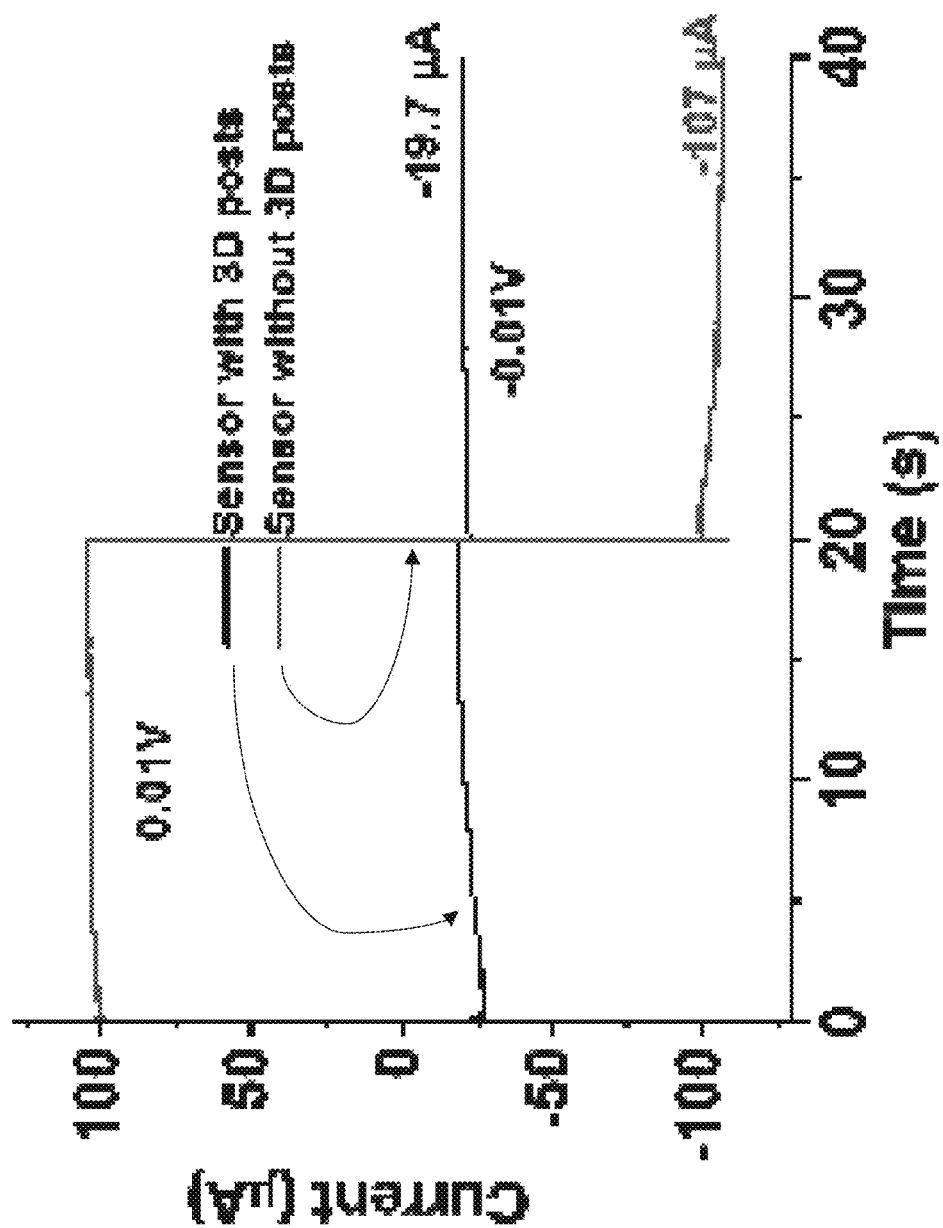
Figure 13B:
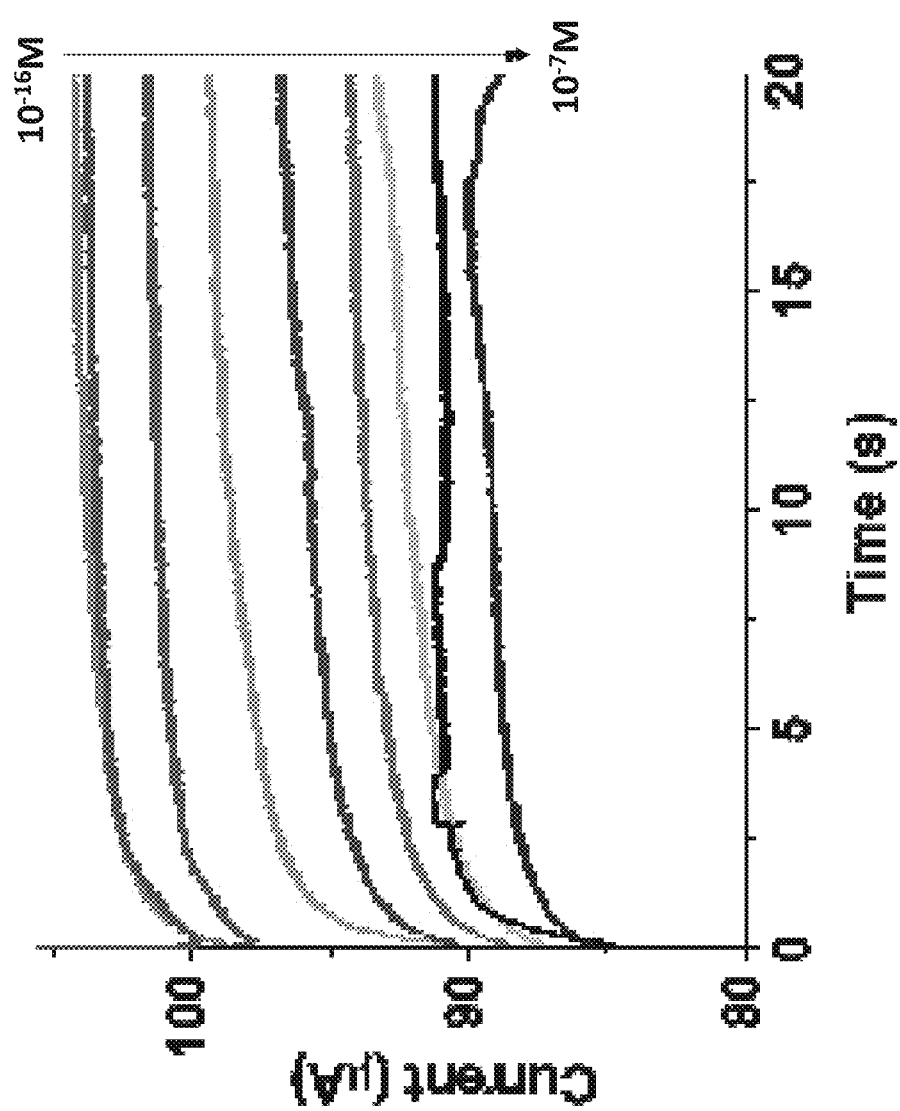
Figure 13C:
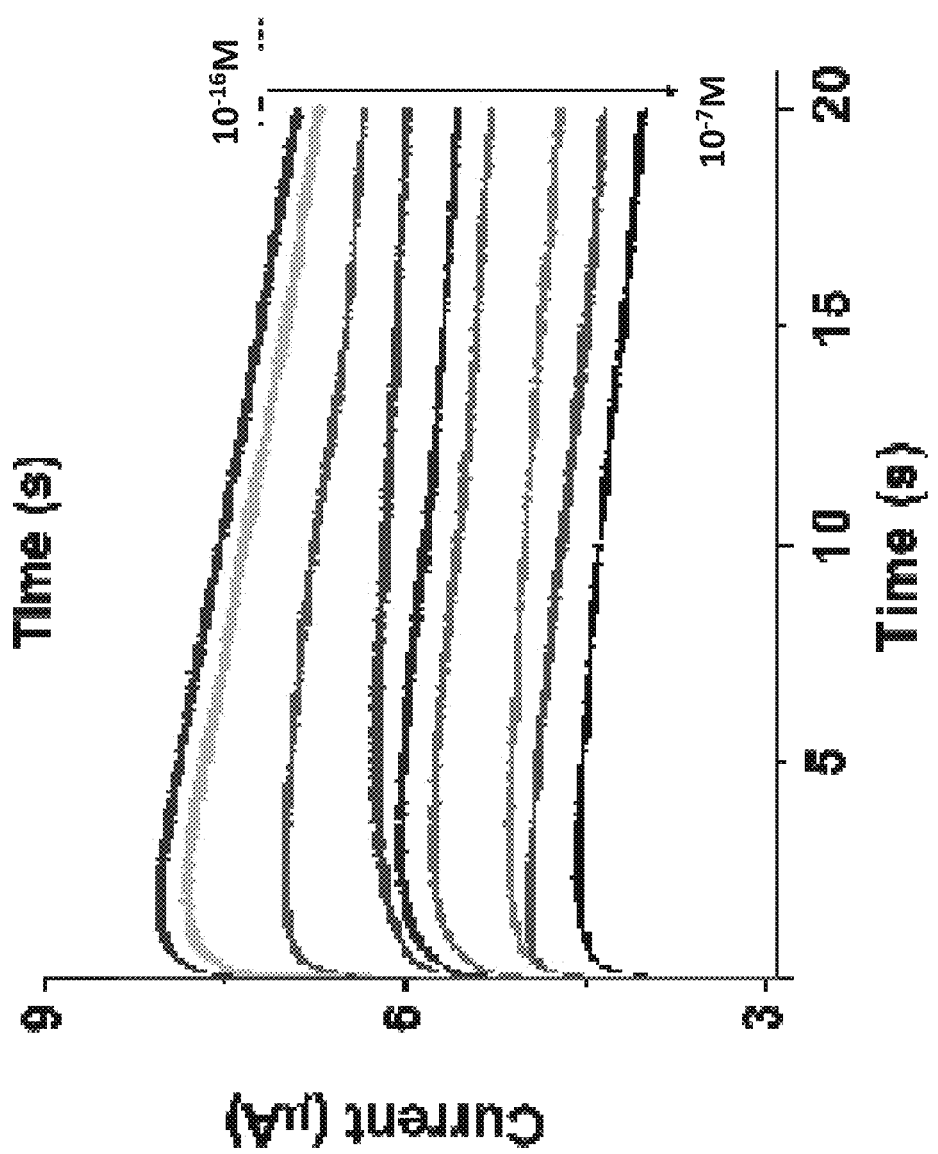

Chronoamperometric (CA) technique was employed to investigate the electrochemical redox reactivity that provided a transient current response of electrode with respect to time. FIG. 13A shows the CA responses for the sensors made by Au nanoposts 15/16/17 and planar Au (without nanoposts) wherein a five-fold enhancement of current is obtained with the Au nanoposts (~107 µA) compared to that of the planar electrode (~19.7 µA). This is because of the nanoposts 15/16/17 act as the nanoelectrodes enabling the radial or spherical diffusion of electrons [12]. However, the planar Au electrode enables linear diffusion resulting in a reduced redox current.

Figure 13D:
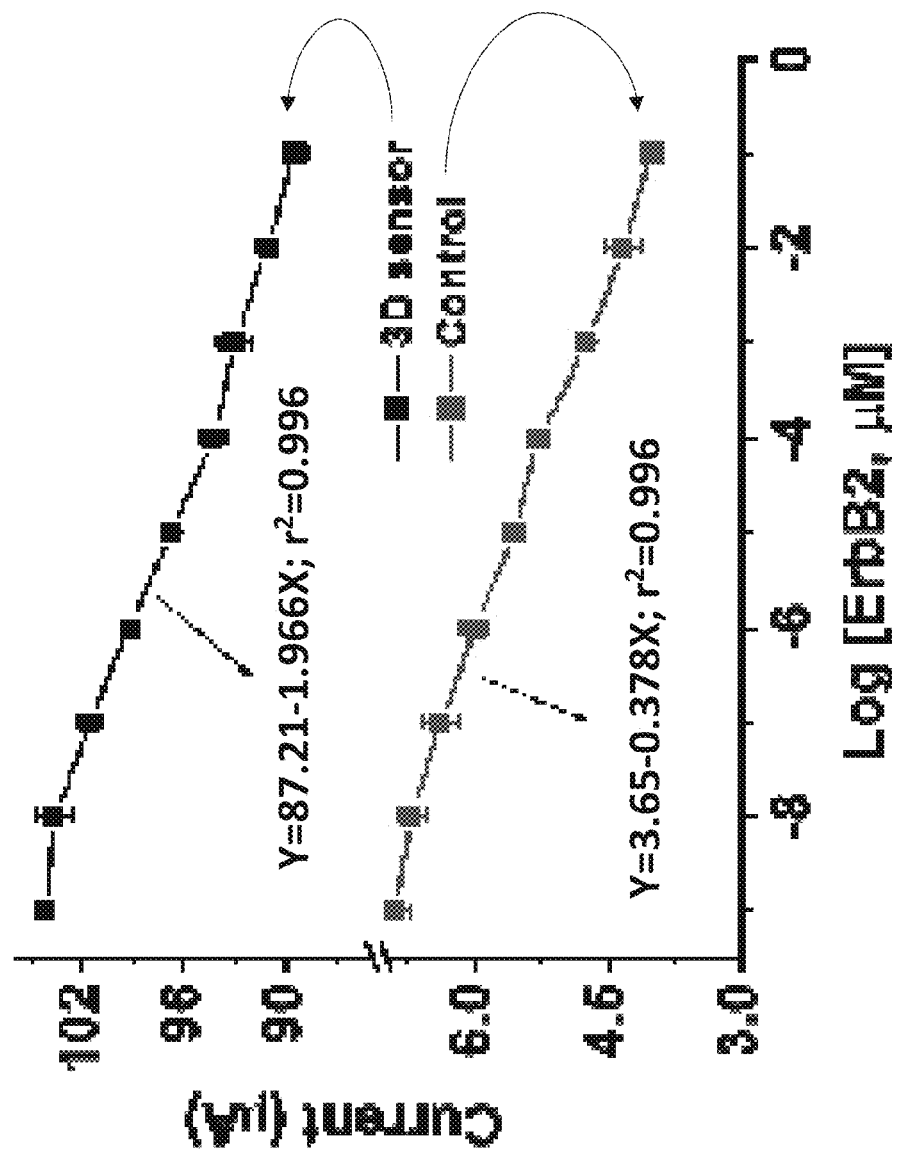

Next, this sensor 10' was exploited to detect specific concentrations of biomarker (ErbB2 antigen 19) using the CA technique. Several concentrations of ErbB2 (1.0 fM to 0.1 µM) were injected to nanoposts sensor 10'. FIGS. 13A-D show the CA responses as a function of ErbB2 concentrations at a potential of 0.01 V for sensors with and without incorporating the Au nanoposts. The sensor responses decrease with increasing ErbB2 concentrations, due to the formation of immunocomplex between anti-ErbB2 and ErbB2 antigen that obstructs the acceleration of generated electrons from redox conversion. With increasing ErbB2 concentration, the immunocomplex layer becomes thicker leading to a reduction in the output current. Calibration plots exhibited that the sensor current is inversely proportional to the logarithmic concentration of ErbB2 antigen (FIG. 13D). Approximately, a six-fold enhancement of sensitivity (20.5 µA/µM/cm$^2$) was obtained for the nanoposts-based sensor, compared to the control sensor without any nanoposts (3.9 µA/µM/cm$^2$). This is because of the larger surface area of the nanoposts and the radial diffusion of electrons towards the nanoposts. Abundant functional groups on the GO sheets also allowed an increased loading of antibody molecules, leading to the formation of more immunocomplex.

Figure 14A:
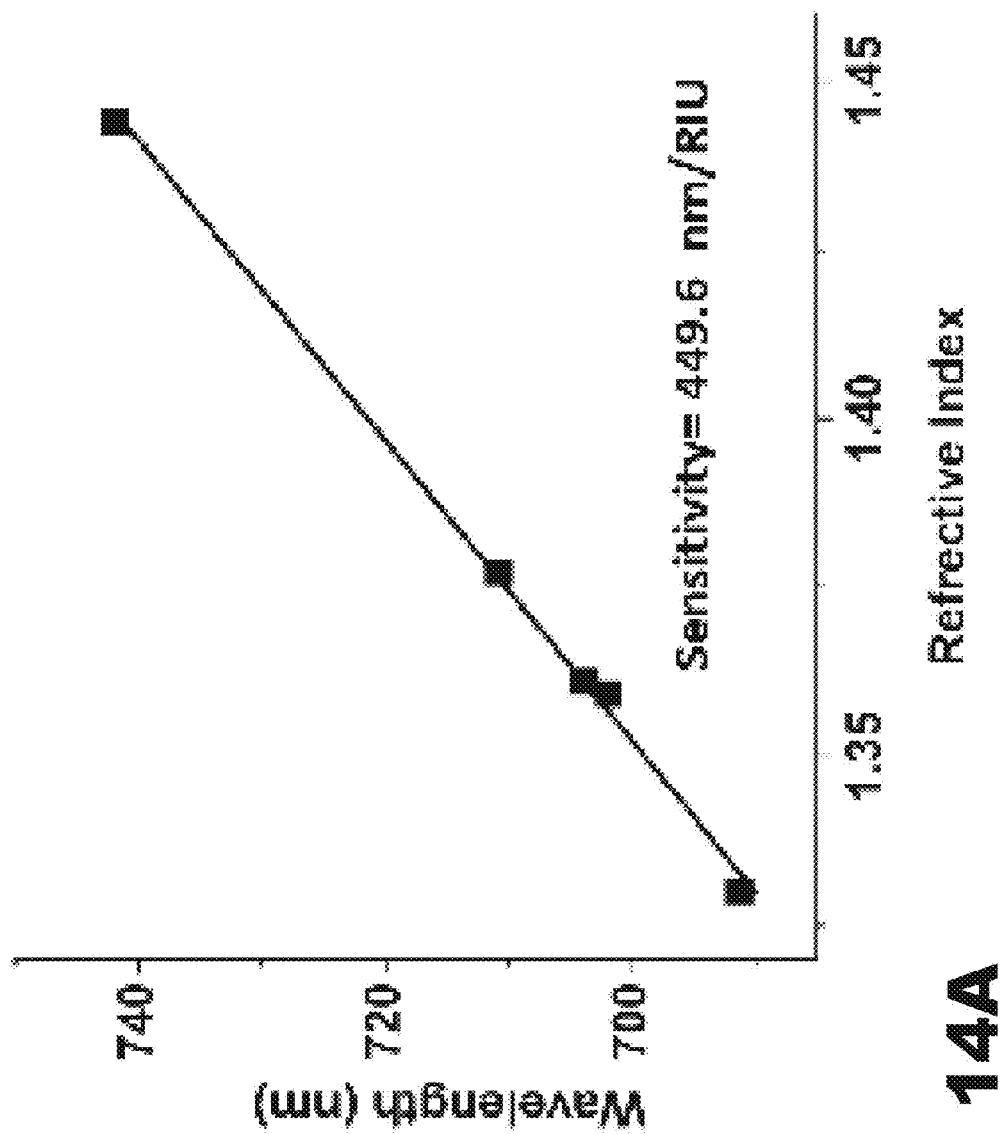
Figure 14B:
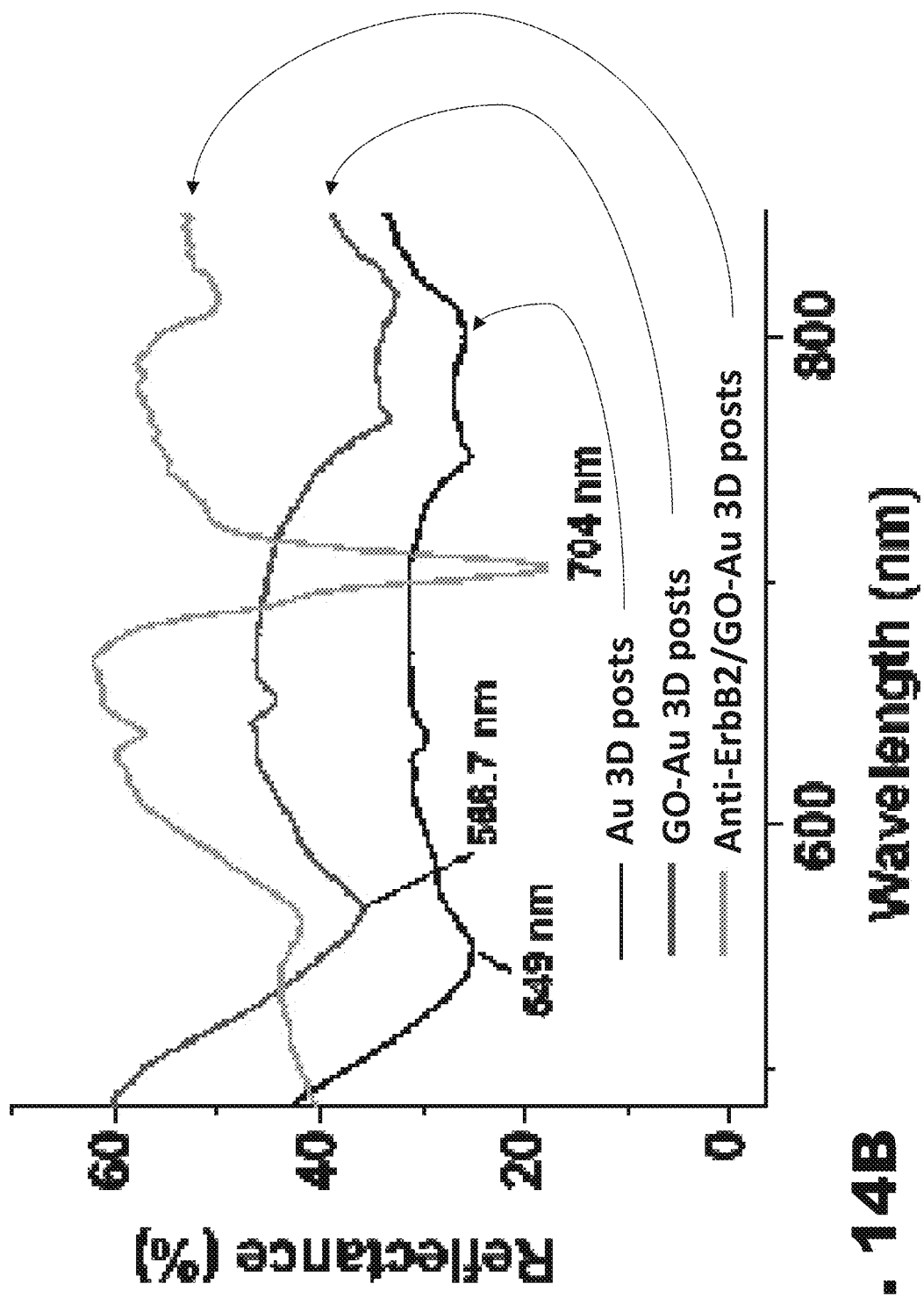
Figure 14C:
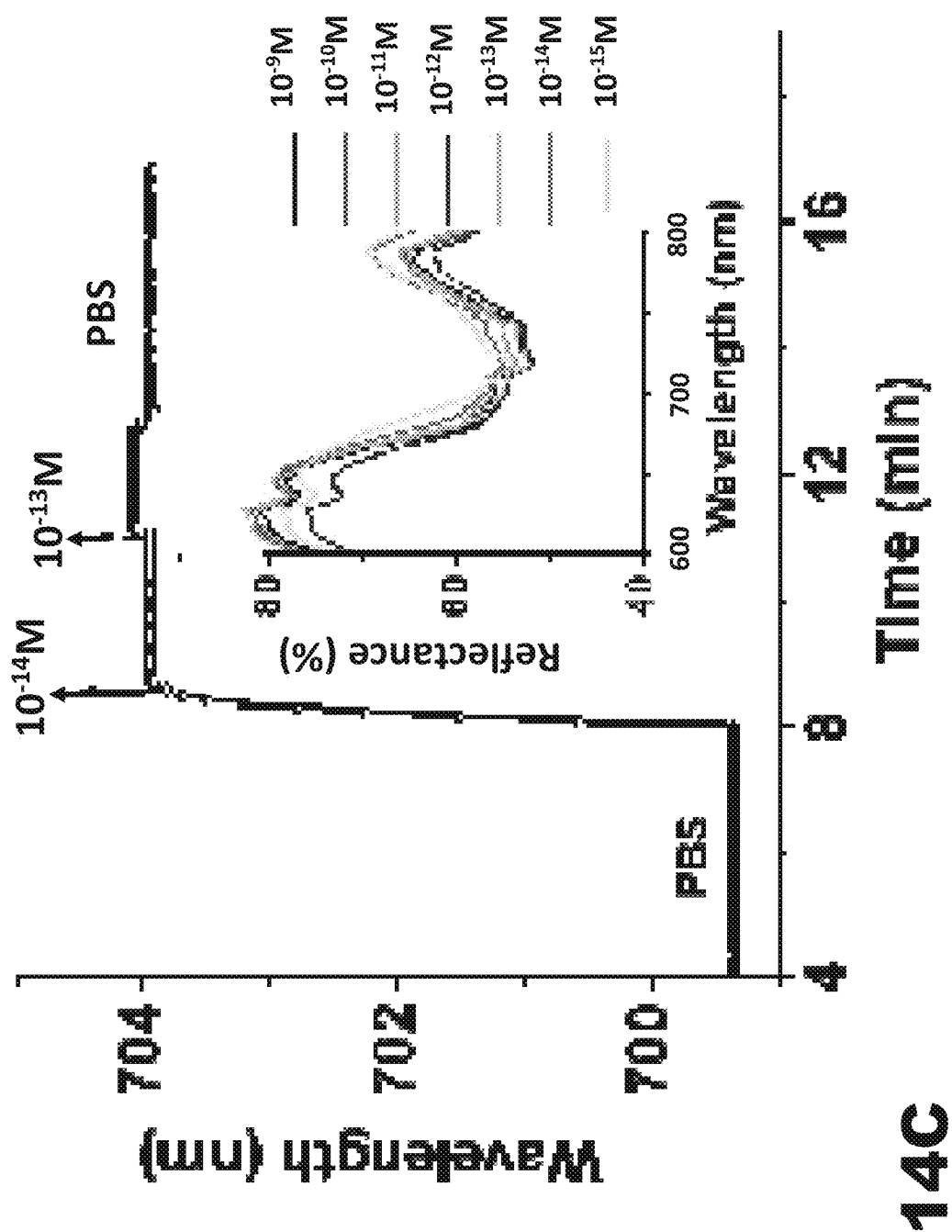
Figure 14D:
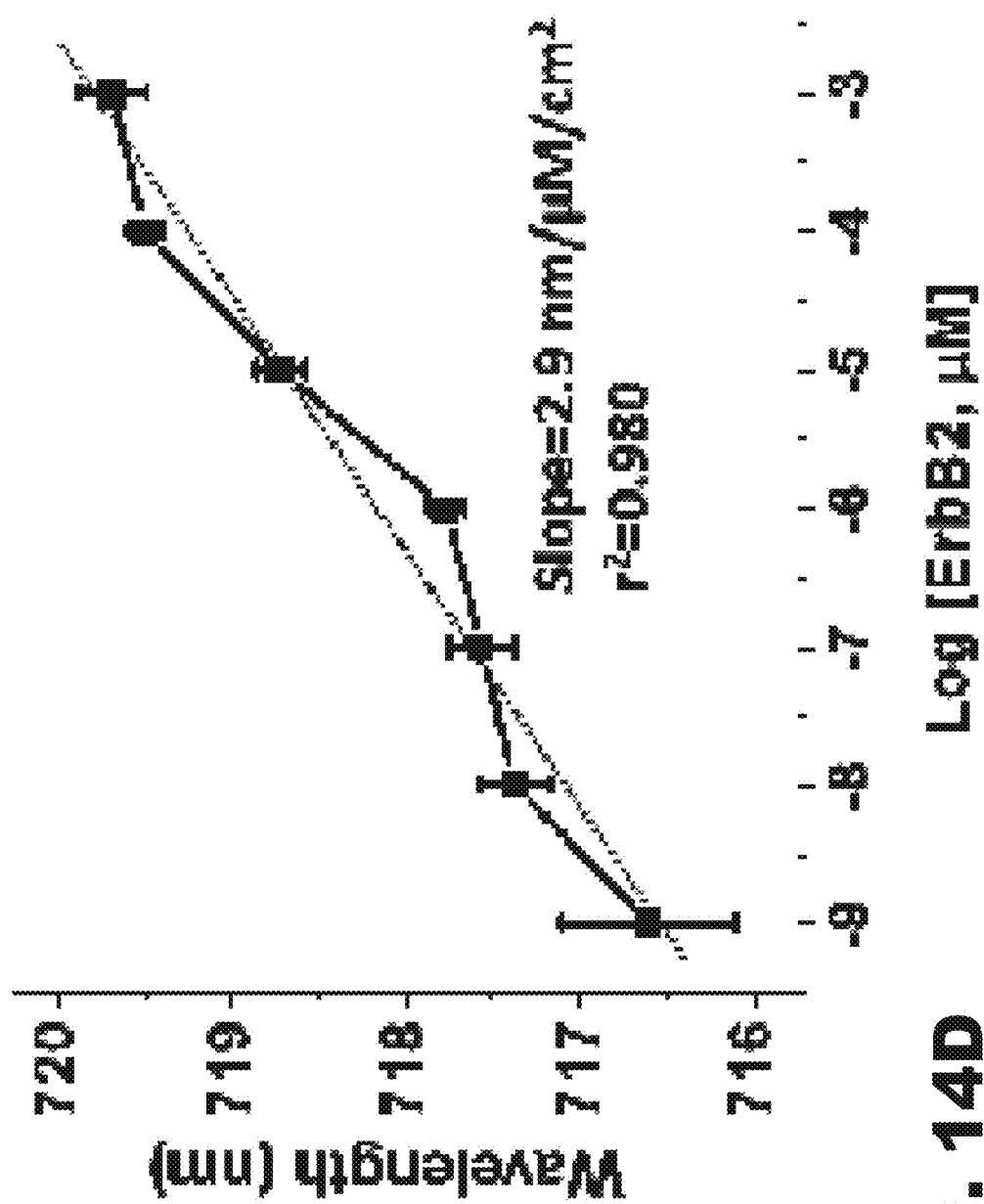

The same sensor was also used for the SPR-based detection of ErbB2 antigen. Coupling of incident light (from light source 42, see FIG. 11) with the Au nanoposts 15/16/17 introduced the SPR signal at the gold-air interface due to the vibration of free electrons at the Au surface [10]. The bulk refractive index sensitivity measurement of the sensor 10' was performed by introducing water, acetone, ethanol, IPA, and chloroform on the sensor surface 13 (FIG. 14A). The spectral shifts of the device in the presence of these chemicals is due to the changes in surrounding refractive index. The bulk index sensitivity of this sensor is found as 449.6 nm/RIU. The SPR spectra are shown for the Au nanoposts with and without GO coating 17, and after anti-ErbB2 18 immobilization (FIG. 14B). After coating the device with a 49 nm thick layer of GO, a 17.7 nm red-shift in resonance wavelength was observed with respect to the bare structure having a resonance at 549 nm. This spectral shift is due to the incorporated GO layer which changes the refractive index at the sensor surface. When the sensor was exposed to the anti-ErbB2 molecules, the wavelength of SPR resonance was further shifted to 704 nm, because of the increased dielectric constant of the environment resulting from the accumulation of polarization charges on the dielectric. FIG. 14C shows the SPR spectra for this sensor 10' as a function of ErbB2 concentrations ($1\times10^{-15}$ M to $1\times10^{-9}$ M) in PBS solution (pH=7.4). When the anti-ErbB2 conjugated nanoposts 15/16/17/18 array 13 was excited by the incident light, a reflection dip was found at a resonance wavelength of 716.5 nm for 1.0 fM concentration of ErbB2 19. This is due to the antigen-antibody interaction on the plasmonic surface that enhances the refractive index at the sensor surface. As the ErbB2 concentration increased from 1 fM to 1 nM, the resonance wavelengths were redshifted from 716.5 to 719.5 nm. FIG. 14D shows the sensor calibration plot between the logarithm concentrations of ErbB2 and the resonance wavelengths. This SPR sensor shows a sensitivity of 2.9 nm/RIU within the low concentration range of ErbB2 biomarker ($1\times10^{-15}$ M to $1\times10^{-9}$ M). A transient response to track dynamically the minute amount of ErbB2 molecules at concentrations of $1\times10^{-14}$ M and $1\times10^{-13}$ M is shown in FIG. 14C. When the sensor 10' was exposed to the PBS solution (baseline), it provided a stable resonance wavelength of 699.3 nm after which the sensor was exposed with ErbB2 ($1\times10^{-14}$ M) molecules 19. This is termed as association phase that provided a redshift of 4.9 nm. By varying the ErbB2 concentration from $1\times10^{-14}$ M to $1\times10^{-13}$ M, this sensor 10' further provided a redshift of 0.18 nm (association phase). In the dissociation phase, the sensor 10' was treated with the PBS solution and the signal decreased due to washing off the weekly bound ErbB2 molecules from the sensor surface.

Figure 15A:
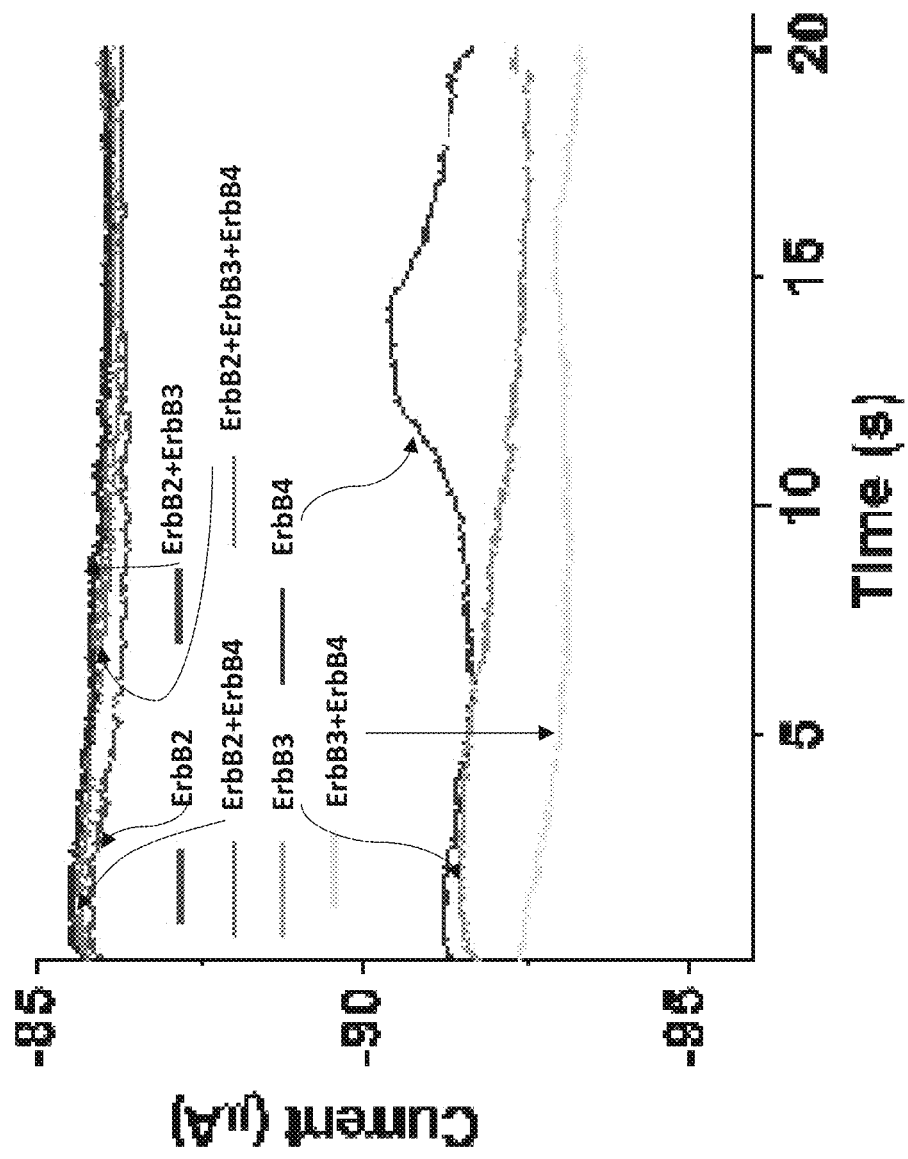
Figure 15B:
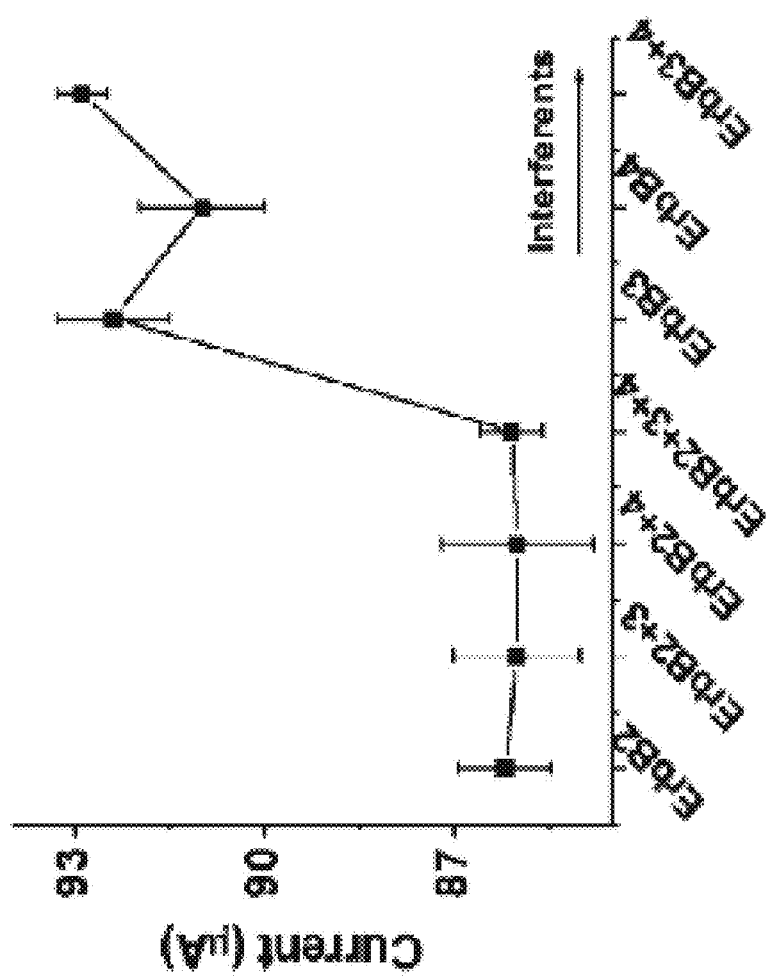
Figure 15C:
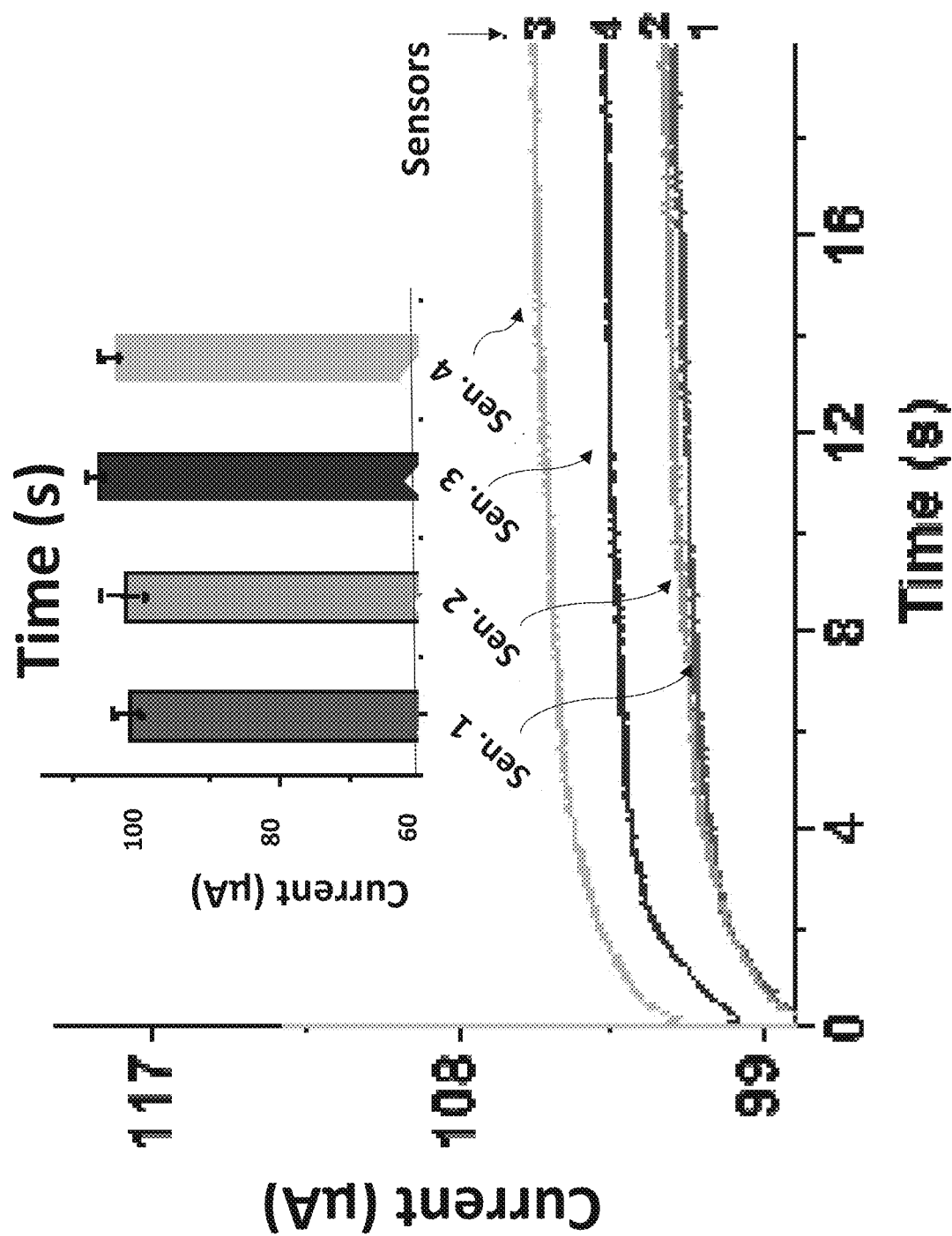
Figure 15D:
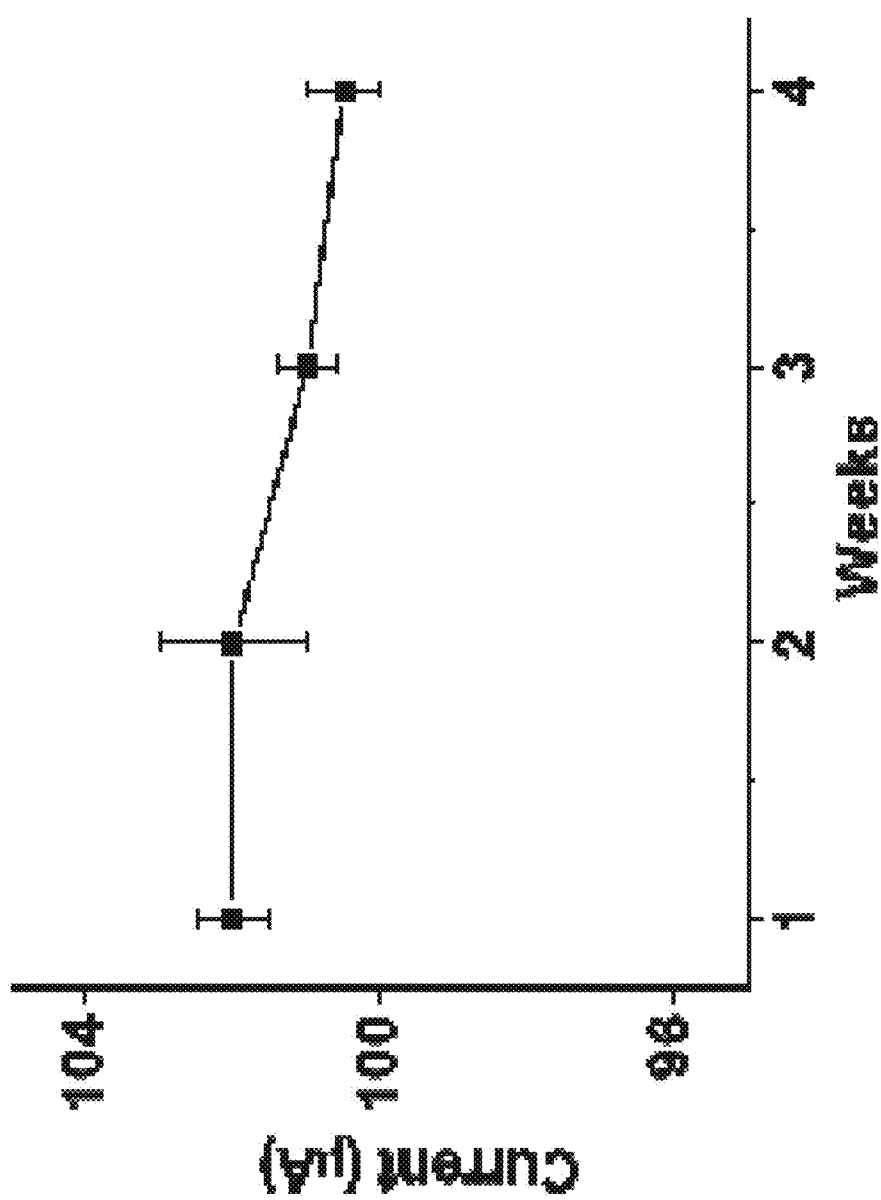

To estimate the selectivity, this sensor 10' was tested with similar species such as ErbB3 and ErbB4 (FIGS. 15A-B). When ErbB2 antigen (1.0 fM) was added to the nonspecific ErbB3, ErbB4, and a mixture of ErbB3 and ErbB4, the sensor response did not change significantly, as evident by its low relative standard deviation (RSD; ±0.11%). The sensor also shows a low RSD of ±1.07% without the ErbB2 antigen. Moreover, the reproducibility tests were conducted using four identical sensors 10'. The measurement revealed high reproducibility with a minute deviation from initial signal (RSD: ±1.95%, FIG. 15C). The high reproducibility of this sensor 10' is due to the periodic and uniform assembly of the Au nanoposts 15/16. Lastly, the sensor 10' exhibited a stable amperometric signature for a four-week measurement (FIG. 15D).

Table 4 compares the performances of this dual-modality sensor with other reported immunosensors. The electrochemical measurement of the sensor offered a higher sensitivity (20.5 µA µM$^{-1}$) than those using other nanostructured materials such as graphene foam-TiO$_2$ nanofibers (0.585 µA µM$^{-1}$)[3] and ZnO nanowires (6.36 nA µM$^{-1}$) [14]. The plasmonic measurement of the sensor provides a competitive detection range, compared to other reported sensors. In addition, the SPR mode allows tracking the associations and dissociations of biomarker molecules, which complements the weak ability of electrochemical detection mode in this regard.

TABLE 4

Comparisons of device performances.

| Electrodes | Biomarkers | Sensitivity | Test range |
|---|---|---|---|
| GF—nTiO$_2$[3] | ErbB2 | 0.585 µA µM$^{-1}$ | 1.0 fM-0.1 µM |
| Ring resonator[13] | HER2 | 30 nM/RIU | 189.5 pM-1.46 nM |
| ZnO nanowires[14] | BRCA1 | 6.36 nA µM$^{-1}$ | 10.0-100.0 µM |
| Graphene sheets[15] | Carcinoembryonic antigen | 0.1 µA pM$^{-1}$ | 2.7-333.3 pM |
| Au nanoposts (this work) | ErbB2 | 20.5 µA µM$^{-1}$ 2.9 nM/µM/cm$^2$ | 1.0 fM-0.1 µM 1.0 fM-1 nM |

Conclusions

A low-cost, highly efficient, and dual-modality sensor has been demonstrated for the detection of cancer biomarkers using both the electrochemical and SPR sensing mechanisms. The larger surface area of the Au nanoposts allows for the sufficient attachment of antibodies to the sensor surface. In the electrochemical mode, the nanoposts enables the radial diffusion of electrons resulting in a several-fold higher sensitivity compared to the bulk electrode without nanoposts. In the SPR mode, the sensor allows easy tracking of the associations and dissociations of biomarker molecules at the sensor surface. Compared to the sensors using synthesized nanomaterials, this sensor offers higher reproducibility due to using the ordered and uniform nanostructures. Therefore, the dual-modality performance of the sensor provides a new approach to improve detection reliability and false alarm immunity for breast cancer detection.

REFERENCES (EACH OF WHICH IS INCORPORATED BY REFERENCE HEREIN IN ITS ENTIRETY)

[1] J. Wang, "Electrochemical Biosensors: Towards Point-of-Care Cancer Diagnostics", *Biosens. Bioelectron.*, vol. 21, pp. 1887-1892, 2006.

[2] I. E. Tothill, "Biosensors for Cancer Markers Diagnosis", *Semin. Cell Dev. Biol.* 2009, 20, 55-62.

[3] Md. A. Ali, K. Mondal, Y. Jiao, S. Oren, Z. Xu, A. Sharma, L. Dong, "Microfluidic Immuno-Biochip for Detection of Breast Cancer Biomarkers Using Hierarchical Composite of Porous Graphene and Titanium Dioxide Nanofibers", *ACS Appl. Mater. Interfaces*, vol. 8, pp. 20570-20582, 2016.

[4] H. Li, J. He, S. Li, A. P. Turner, "Electrochemical Immunosensor with N-doped Graphene-Modified Electrode for Label-Free Detection of the Breast Cancer Biomarker CA 15-3", *Biosens. Bioelectron*, vol. 43, pp. 25-29, 2013.

[5] Z. Gao, H. Deng, W. Shen, Y. Ren "A Label-Free Biosensor for Electrochemical Detection of Femtomolar microRNAs" *Anal. Chem.*, vol. 85, pp. 1624-1630, 2013.

[6] J. Heinze, "Ultramicroelectrodes in Electrochemistry", *Angew. Chem. Int. Ed. Engl.*, vol. 32, pp. 1268-1288, 1993.

[7] M. Holzinger, A. Le Goff, S. Cosnier "Nanomaterials for Biosensing Applications: A Review", *Front. Chem.*, vol. 2, pp. 63, 2014.

[8] G. J. Nusz, A. C. Curry, S. M. Marinakos, A. Wax, A. Chilkoti, "Rational Selection of Gold Nanorod Geometry for Label-Free Plasmonic Biosensors", *ACS Nano*, vol. 3, pp. 795-806, 2009.

[9] M. E. Stewart, C. R. Anderton, L. B. Thompson, J. Maria, S. K. Gray, J. A. Rogers, R. G. Nuzzo, "Nanostructured Plasmonic Sensors", *Chem. Rev.*, vol. 108, pp. 494-521, 2008.

[10] Q. Wang, W. Han, P. Liu, and L. Dong, "Electrically Tunable Quasi-3D Mushroom Plasmonic Crystal", *J. Lightw. Technol.*, vol. 34, pp. 2175-2181, 2015.

[11] D. J. Beebe, J. S. Moore, Q. Yu, R. H. Liu, M. L. Kraft, B.-H. Jo, C. Devadoss, "Microfluidic tectonics: A comprehensive construction platform for microfluidic systems", *Proc. Natl. Acad Sci.*, vol. 97. pp. 13488-93, 2000.

[12] M. E. Sandison, J. M. Cooper, "Nanofabrication of Electrode Arrays by Electron-Beam and Nanoimprint Lithographies", Lab Chip, vol. 6, pp. 1020-5, 2006.

[13] J. T. Gohring, P. S. Dale, X. Fan, "Detection of HER2 Breast Cancer Biomarker Using the Opto-Fluidic Ring Resonator Biosensor", *Sens. Actuat. B*, vol. 146, pp. 226-30, 2010.

[14] N. A. Mansor, Z. M. Zain, H. H. Hamzah, et al., "Detection of Breast Cancer 1 (BRCA1) Gene Using an Electrochemical DNA Biosensor Based on Immobilized ZnO Nanowires", *Open J. Appl. Biosens.* vol. 3, pp. 9-17, 2014.

[15] X. Chen, X Jia, J. Han, J. Ma, Z. Ma "Electrochemical Immunosensor for Simultaneous Detection of Multiplex Cancer Biomarkers Based on Graphene Nanocomposites", *Biosens. Bioelectron.*, vol. 50, pp. 356-361, 2013.

E. Options and Alternatives

As previously stated, the invention can take many forms and embodiments. Variations obvious to those skilled in the art will be included with the invention. A few non-limiting examples are as follows:

1. Biomarkers

Biomarkers could include both disease related and drug-related biomarkers. As indicated, antigens for the relevant biomarker of interest must have characteristics to effectively attract and bind the relevant biomarker of interest from an analyte sample. Those skilled-in-the art would know which antigen to use for which biomarker.

Also, as indicated, the relatively small size of the sensor (micro-scale in perimeter dimension and nanoscale in form factor of the nanoposts) allows relatively small analyte samples to be measured. As is well-appreciated in this technical area, this can be extremely beneficial. Sometimes the overall volume of sample is limited. The invention therefore promotes accurate and precise measurements of such precious small samples. Sometimes the overall volume of sample is not extremely limited, but if only small portions of the overall sample are used for each measurement, plural portions can be measured either serially or in parallel for comparison and/or validation purposes.

2. Patterned Array

A periodic array of nanoposts is illustrated in the drawings. This is but one form the 3-D structures in the pattern can take. As will be appreciated, other shapes which are elongated along an axis from the floor 24 (see FIG. 10) to a distal end are possible. For purposes herein, the term nanopost includes any such structure when generally identical across the array in form factor and spacing. The nanopost does not have to be precisely cylindrical.

Additionally, the specific spacing between nanoposts and the ratio of nanopost diameter to space between nanoposts can vary according to need or desire. This can be a function of several factors including but not limited to overall size of the sensing area 13, the required volume of analyte samples, the nature and thickness of the noble metal and GO layers, and the wavelengths of excitation light for SPR measurements.

Soft lithography is one way to fabrication the pattern with sufficient precision, accuracy, and reproducibility. Other MEMs techniques that achieve similar results are possible.

3. Metal Layer

Gold(Au) of the specific examples could be replaced by other electrically conducting materials. Silver, titanium, or noble metals are examples. A noble metal is a metal or alloy characterized by its lack of chemical reactivity (e.g. resist oxidation and corrosion in any environment), as opposed to base metals, which more readily oxidize and corrode. Noble metals include gold, silver, mercury, and the platinum group, including palladium, iridium, rhodium, ruthenium, and osmium (metals of groups VIIB, VIII, and IB of the second and third transition series of the periodic table). As will be appreciated, any of the foregoing or alloys of the same are candidates, but typically gold or silver would be the most practical.

4. GO Layer

Graphene oxide is intended to include graphene derivatives.

Graphene oxide could be replaced by other chemical groups such as amino, carboxyl, azido, thiol, alkyne, vinyl, and epoxy, to allow bonding of anti-body molecules at the metal surface.

5. Microfluidic Sub-System

As will be appreciated by those skilled in this technical art, a variety of microfluidic techniques and configurations could be used to convey sample analyte to sensing area 13 (with nanoposts 15). This would include valves, pumps, and other components to accomplish the same. Various of the cited references herein give examples.

6. Electrochemical Sub-System

As will be appreciated by those skilled in this technical art, a variety of configurations and techniques are possible to utilize an electrode-based sensing at the sensing area 13. The Specific Examples describe several. Various of the cited references herein also give examples.

7. SPR Sub-System

As will be appreciated by those skilled in this technical art, a variety of configurations and techniques are possible to set up and acquire SPR-type measurements at the sensing area 13. The Specific Examples describe several. Various of the cited references herein also give examples.

8. Controller/Processor

As will be appreciated by those skilled in this technical art, a variety of configurations and techniques are possible to utilize and program a digital controller and/or processor to perform automatic or semi-automatic functions and sequences of functions with the microfluidic, electrochemical, and SPR sub-systems, as well as acquire, process, communicate, and/or store data related to such operations. The Specific Examples describe several. Various of the cited references herein also give examples.

9. System Scaling

As will further be appreciated by those skilled in this technical art, a single sensor 10 or 10' can be fabricated and utilized. But, of course, plural sensors 10 or 10' could be fabricated either as individual lab-on-chip assemblies each with a single sensing area or with several sensing areas 13 per chip, each with appropriate ways to microfluidically provide an analyte sample to each sensing area 13 and take the dual-modality measurements simultaneously at each sensing area.

Additionally, by MEMs techniques, fabrication could be scaled up to produce many sensing areas to process in parallel many analyte samples.

What is claimed is:

1. A method of biomarker detection in a flowable sample volume comprising:
   a. fabricating a sensing area of:
      i. a periodic array of nanostructures, each nanostructure comprising:
         1. a polymeric nanopost;
         2. a metal layer conformed to the shape of and over at least a portion of each nanopost;
         3. a binding layer that facilitates molecular binding conformed to the shape of and over at least a portion of the metal layer at each nanopost; and
         4. receptor molecules over at least a portion of the binding layer at each nanopost specifically functionalized for binding to a biomarker molecule of interest;
   b. presenting the flowable sample volume to the periodic array of nanostructures at the sensing area to provide a larger surface area, increased loading capacity, and radial or spherical diffusion paths for the flowable sample volume as compared to a planar surface;
   c. at the same sensing area and using the same sample volume:
      i. taking electrochemical measurements; and
      ii. taking surface plasmon resonance (SPR) measurements; and
   d. evaluating the electrochemical and SPR measurements relative to the biomarker molecule of interest.

2. The method of claim 1 wherein:
   a. the nanoposts comprise ZPUA;
   b. the metal comprises Au, Au and Ti, or Ag;
   c. the binding layer comprises GO or graphene-based material or other chemical groups such as amino, carboxyl, azido, thiol, alkyne, vinyl, and epoxy to allow binding of anti-body molecules to the metal surface;
   d. the sample volume is provided to the sensing area by microfluidics.

3. The method of claim 1 wherein:
   a. the nanostructures promote radial or spherical diffusions of redox species from bulk solutions relative to the periodic array of nanostructures.

4. The method of claim 1 wherein the nanostructures promote high reproducibility of sensor response to receptor molecules at femtomolar level.

5. The method of claim 1 wherein:
   a. the biomarker of interest comprises an antigen;
   b. the receptor molecules comprise anti-bodies to the antigen and are covalently immobilized on the nanoposts.

6. The method of claim 3 wherein:
   a. the electrochemical measurements are compared to calibration measurements to estimate concentration of the antigen at the sensing area; and
   b. SPR measurements are compared to calibration measurements to estimate concentration of the antigen at the sensing area.

7. The method of claim 6 wherein the comparisons are both used to estimate a final concentration of the antigen at the sensing area sufficient to represent a biomarker related to the antigen.

8. The method of claim 1 wherein the biomarker of interest relates to cancerous tissues or other disease-related biomarkers or drug-related biomarkers.

9. The method of claim 8 wherein the cancerous tissue comprises breast cancer and the antigen comprises ErbB.

10. The method of claim 1 wherein the nanoposts are fabricated using soft lithography.

11. A system for detecting a target biomarker from a sample, the system having a small footprint, low sample consumption, and improved detection reliability comprising:
   a. a sensing chip with a sensing area comprising:
      i. a periodic array of nanostructures comprising nanoposts covered in metal and a binding layer biofunctionalized with anti-target molecules that bind with target biomarker molecules related to the target biomarker:
   b. a microfluidic circuit to provide a volume of sample to the periodic array of nanostructures at the sensing area of the sensing chip;
   c. an electrochemical sensing modality comprising an electrode set and a source of electrical power adapted to obtain electrochemical measurements at the periodic array of nanostructures at the sensing area, the array of nanostructures presenting a larger surface area, increased loading capacity, and radial or spherical diffusion paths to a sample volume as compared to a planar surface;
   d. an SPR sensing modality comprising an illumination source and a spectrometer adapted to obtain SPR measurements at the periodic array of nanostructures at the sensing area, wherein the SPR sensor comprises: i. a light source and optics to couple light from the light source light to illuminate the sensing area, and ii. collection optics and a spectrometer to collect and measure reflectance from the sensing area;
   e. a control circuitry in operative connection to and adapted to:
      i. control the microfluidic subsystem to present a sample volume to the periodic array of nanostructures at the sensing area;
      ii. simultaneously collect signals from;
         1. operation of the source of electrical power and the electrode set in the electrochemical sensing modality; and
         2. operation of light source and spectrometer in the SPR sensing modality:
      iii. process the collected signals into one or more of (a) an estimate of presence and/or concentration of the biomarker of interest in a sample volume, and (b) another parameter relating to the biomarker of interest.

12. The system of claim 11 wherein the array of nanoposts is fabricated with soft lithography.

13. The system of claim 11 wherein the electrochemical sensing subsystem includes at the sensing area a working electrode comprising the array of nanoposts, a counter electrode on one side of the sensing area, a reference electrode on an opposite side of the sensing area, and electrical power source adapted to provide a constant potential at the working electrode with respect to the reference electrode.

14. The system of claim 11 wherein:
   a. the light source is a white light source and optics to couple the white light to illuminate the sensing area;
   b. the collection optics and a spectrometer collect and measure reflectance from the sensing area.

15. The system of claim 11 wherein the control subsystem is adapted to:
   a. characterize measurements from both of the electrochemical and SPR sensing modalities;
   b. derive specific concentration estimates of the biomarker by comparison to calibrations.

16. The system of claim 11 wherein:
   a. the nanoposts are on the order of:
      i. pitch of 500 nm;
      ii. diameter of 250 nm; and
      iii. depth of 210 nm;
   b. the metal is on the order of:
      i. 80 nm thick;
   c. the binding layer is GO and is on the order of:
      i. 20 nm thick;
   d. the sensing area is on the order of:
      i. 3.4 mm diameter;
   e. the microfluidic channels are on the order of:
      i. 400 μm deep; and
      ii. 1.5 mm wide.

17. The system of claim 11 wherein the target biomarker is ErbB.

18. The system of claim 17 wherein the anti-target molecules comprises ErbB2, ErbB3, or ErbB4 anti-bodies.

19. The system of claim 11 further comprising one or more additional said sensing chips for processing multiple samples in parallel.

20. A biomarker detector comprising:
   a. a microfluidic chip comprising a sensing area and a microfluidic network to supply a sample volume to the sensing area;
   b. the sensing area comprising:
      i. a periodic array of nanostructures, each nanostructure comprising:
         1. a metal layer over at least a portion of each nanostructure;
         2. a binding layer over at least a portion of the metal layer at each nanostructure; and
         3. receptor molecules over at least a portion of the binding layer at each nanostructure specifically functionalized for binding to a biomarker of interest;
   c. wherein both electrochemical measurements and surface plasmon resonance (SPR) measurements can be taken and evaluated for presence of the biomarker of interest at the same sensing area and using the same sample volume.

21. A method of fabricating the biomarker detector of claim 20 comprising:
   a. creating a nano stamp of nanoposts;
   b. pouring a polymeric solution onto the nano-stamp, curing the polymeric solution on the nano-stamp, and peeling the cured polymeric solution from the nano-stamp to create a nanohole mold;
   c. pouring a UV curable polymeric solution onto the mold, and exposing the polymeric solution to UV to produce an array of polymer nanoposts;
   d. depositing a metal layer onto the nanoposts;
   e. drop coating the metalized nanoposts with nanosheets of GO;
   f. biofunctionalizing the metalized and GO coated nanoposts with anti-molecules to a biomarker of interest to create the nanostructures; and
   g. creating microfluidic channels in a photo pattemable polymer substrate to create the microfluidic network.

22. A biosensor comprising:
a. a microfluidic channel to deliver an analyte sample;
b. a sensor chip operatively connected to the microfluidic channel, the sensor chip comprising a patterned periodic array of nanostructures comprising nanoposts coated with an electrical conductor and a graphene-based material, and functionalized with specific receptor molecules, the periodic array of nanostructures configured to detect biomarker molecules in a limited volume of an analyte sample with accuracy and precision via electrochemical and SPR signals from a single sensing area at the patterned periodic array of nanostructures by presenting:
   i. a spatially well-defined nanostructured working electrode for electrochemical sensing; and
   ii. a nanostructured plasmonic crystal for SPR sensing via excitation of surface plasmon polaritons.

* * * * *